US012562281B2

(12) United States Patent
Abu El Ata et al.

(10) Patent No.: US 12,562,281 B2
(45) Date of Patent: Feb. 24, 2026

(54) PREDICTIVE RISK ASSESSMENT IN PATIENT AND HEALTH MODELING

(71) Applicant: X-Act Science, Inc., Tortola (VG)

(72) Inventors: Nabil A. Abu El Ata, New York, NY (US); Annie Druebert, New York, NY (US); Tomy Abu El Ata, New York, NY (US)

(73) Assignee: X-Act Science, Inc., Tortola (VG)

( * ) Notice: Subject to any disclaimer, the term of this patent is extended or adjusted under 35 U.S.C. 154(b) by 776 days.

(21) Appl. No.: 17/447,252

(22) Filed: Sep. 9, 2021

(65) Prior Publication Data

US 2022/0076841 A1     Mar. 10, 2022

Related U.S. Application Data

(60) Provisional application No. 63/076,243, filed on Sep. 9, 2020.

(51) Int. Cl.
| | |
|---|---|
| *G16H 50/20* | (2018.01) |
| *G16H 10/60* | (2018.01) |
| *G16H 15/00* | (2018.01) |
| *G16H 50/30* | (2018.01) |
| *G16H 50/50* | (2018.01) |

(52) U.S. Cl.
CPC ............. *G16H 50/30* (2018.01); *G16H 10/60* (2018.01); *G16H 15/00* (2018.01); *G16H 50/20* (2018.01); *G16H 50/50* (2018.01)

(58) Field of Classification Search
CPC ........ G16H 50/30; G16H 50/50; G16H 10/60; G16H 15/00; G16H 50/20
See application file for complete search history.

(56) References Cited

U.S. PATENT DOCUMENTS

| | | |
|---|---|---|
| 5,146,591 A | 9/1992 | Bachman et al. |
| 5,193,183 A | 3/1993 | Bachman |

(Continued)

OTHER PUBLICATIONS

Kamel Boulos, M.,N., & Zhang, P. (2021). Digital twins: From personalised medicine to precision public health. Journal of Personalized Medicine, (Year: 2021).*

(Continued)

*Primary Examiner* — Matthew L Hamilton
(74) *Attorney, Agent, or Firm* — Hamilton, Brook, Smith & Reynolds, P.C.

(57)     ABSTRACT

A patient's health is modeled through multiple scenarios. A base model incorporates rules that govern a response by a human being to one or more diseases, as well as a relation between health metrics and the diseases. Health attributes of the patient are obtained. From the base model and the health attributes, a patient model is generated. The patient model is modeled under different parameters to generate health metrics. From an analysis of the parameters and the resulting health metrics, occurrence probabilities for each of the sets of parameters are determined. Risks are identified, which indicate a likelihood of the patient transitioning from the initial state to an adverse outcome such as a diseased state. A report provides a diagnosis of the patient and one or more remedies/interventions that are predicted, based on the plural sets of parameters and resulting health metrics, to avoid or prevent an adverse outcome.

18 Claims, 31 Drawing Sheets

(56) References Cited

U.S. PATENT DOCUMENTS

| | | | |
|---|---|---|---|
| 5,195,178 | A | 3/1993 | Krieger et al. |
| 5,208,765 | A | 5/1993 | Turnbull |
| 5,233,513 | A | 8/1993 | Doyle |
| 5,241,645 | A | 8/1993 | Cimral et al. |
| 5,276,877 | A | 1/1994 | Friedrich et al. |
| 5,297,279 | A | 3/1994 | Bannon et al. |
| 5,446,874 | A | 8/1995 | Waclawsky et al. |
| 5,486,995 | A | 1/1996 | Krist et al. |
| 5,522,014 | A | 5/1996 | Clark et al. |
| 5,539,652 | A | 7/1996 | Tegethoff |
| 5,680,590 | A | 10/1997 | Parti |
| 5,724,556 | A | 3/1998 | Souder et al. |
| 5,724,569 | A | 3/1998 | Andres |
| 5,726,914 | A | 3/1998 | Janovski et al. |
| 5,729,746 | A | 3/1998 | Leonard |
| 5,771,370 | A | 6/1998 | Klein |
| 5,790,789 | A | 8/1998 | Suarez |
| 5,801,958 | A | 9/1998 | Dangelo et al. |
| 5,809,282 | A | 9/1998 | Cooper et al. |
| 5,822,749 | A | 10/1998 | Agarwal |
| 5,881,268 | A | 3/1999 | McDonald et al. |
| 5,893,074 | A | 4/1999 | Hughes et al. |
| 5,937,165 | A | 8/1999 | Schwaller et al. |
| 5,953,707 | A | 9/1999 | Huang et al. |
| 5,958,009 | A | 9/1999 | Friedrich et al. |
| 5,984,511 | A | 11/1999 | Vasey-Glandon et al. |
| 5,999,734 | A | 12/1999 | Willis et al. |
| 6,003,079 | A | 12/1999 | Friedrich et al. |
| 6,009,256 | A | 12/1999 | Tseng et al. |
| 6,023,706 | A | 2/2000 | Schmuck et al. |
| RE36,602 | E | 3/2000 | Sebastian et al. |
| 6,038,540 | A | 3/2000 | Krist et al. |
| 6,067,412 | A | 5/2000 | Blake et al. |
| 6,115,718 | A | 9/2000 | Huberman et al. |
| 6,119,125 | A | 9/2000 | Glouderman et al. |
| 6,145,121 | A | 11/2000 | Levy et al. |
| 6,272,507 | B1 | 8/2001 | Pirolli et al. |
| 6,311,144 | B1 | 10/2001 | Abu El Ata |
| 6,327,551 | B1 | 12/2001 | Peterson et al. |
| 6,370,681 | B1 | 4/2002 | Dellarocas et al. |
| 6,393,386 | B1 | 5/2002 | Zager et al. |
| 6,532,465 | B2 | 3/2003 | Hartley et al. |
| 6,560,569 | B1 | 5/2003 | Abu El Ata |
| 6,662,355 | B1 | 12/2003 | Caswell et al. |
| 6,904,449 | B1 | 6/2005 | Quinones |
| 6,990,437 | B1 | 1/2006 | Abu El Ata |
| 7,031,901 | B2 | 4/2006 | Abu El Ata |
| 7,035,786 | B1 | 4/2006 | Abu El Ata et al. |
| 7,343,406 | B1 | 3/2008 | Buonanno et al. |
| 7,389,211 | B2 | 6/2008 | Abu El Ata et al. |
| 7,441,249 | B2 | 10/2008 | Adachi et al. |
| 7,783,468 | B2 | 8/2010 | Abu el Ata et al. |
| 7,881,920 | B2 | 2/2011 | Abu El Ata et al. |
| 8,103,456 | B2 | 1/2012 | Doniger et al. |
| 8,280,657 | B2 | 10/2012 | Van Gorp et al. |
| 8,364,519 | B1 | 1/2013 | Basu et al. |
| 8,577,775 | B1 | 11/2013 | Gerber |
| 10,726,362 | B2 | 7/2020 | Abu El Ata |
| 11,030,551 | B2 | 6/2021 | Abu El Ata |
| 11,334,831 | B2 | 5/2022 | Abu El Ata et al. |
| 11,392,875 | B2 | 7/2022 | Carstens |
| 11,631,480 | B1 | 4/2023 | Linetsky et al. |
| 11,862,304 | B1 | 1/2024 | Klein |
| 2001/0027527 | A1 | 10/2001 | Khidekel et al. |
| 2001/0041996 | A1 | 11/2001 | Eder |
| 2002/0069235 | A1 | 6/2002 | Chen |
| 2002/0077717 | A1 | 6/2002 | Harburda et al. |
| 2004/0128618 | A1 | 7/2004 | Datta |
| 2004/0138933 | A1 | 7/2004 | LaComb et al. |
| 2004/0167765 | A1 | 8/2004 | Abu El Ata |
| 2004/0249482 | A1 | 12/2004 | Abu El Ata et al. |
| 2005/0043977 | A1 | 2/2005 | Ahern et al. |
| 2005/0144150 | A1 | 6/2005 | Ramamurthy et al. |
| 2006/0241931 | A1 | 10/2006 | Abu el Ata et al. |
| 2007/0219816 | A1 | 9/2007 | Van Luchene et al. |
| 2007/0294121 | A1 | 12/2007 | Galt et al. |
| 2007/0294128 | A1 | 12/2007 | Wedemeyer |
| 2007/0299706 | A1 | 12/2007 | Galt et al. |
| 2007/0299720 | A1 | 12/2007 | Tafoya |
| 2008/0010082 | A1 | 1/2008 | Jiang et al. |
| 2008/0162232 | A1 | 7/2008 | Gamarnik et al. |
| 2008/0243543 | A1 | 10/2008 | Jung et al. |
| 2008/0312986 | A1 | 12/2008 | Braun et al. |
| 2009/0112668 | A1 | 4/2009 | Abu El Ata |
| 2009/0182593 | A1 | 7/2009 | Whitmore |
| 2009/0204234 | A1 | 8/2009 | Sustaeta et al. |
| 2009/0254411 | A1 | 10/2009 | Bhattacharya et al. |
| 2010/0004963 | A1 | 1/2010 | Ficery et al. |
| 2010/0004977 | A1 | 1/2010 | Marci et al. |
| 2010/0191472 | A1 | 7/2010 | Doniger et al. |
| 2011/0078411 | A1 | 3/2011 | Maclinovsky et al. |
| 2011/0295618 | A1 | 12/2011 | Naipaul et al. |
| 2011/0295621 | A1 | 12/2011 | Faroq et al. |
| 2012/0016714 | A1 | 1/2012 | Apte et al. |
| 2012/0022939 | A1 | 1/2012 | Tiwari et al. |
| 2012/0035962 | A1 | 2/2012 | Liff |
| 2012/0046999 | A1 | 2/2012 | Jayaraman et al. |
| 2012/0197686 | A1 | 8/2012 | Abu El Ata |
| 2012/0210292 | A1 | 8/2012 | Zhang et al. |
| 2012/0316930 | A1 | 12/2012 | Clemenson |
| 2013/0060603 | A1 | 3/2013 | Wagner |
| 2013/0282415 | A1 | 10/2013 | Salto et al. |
| 2015/0333992 | A1 | 11/2015 | Vasseur et al. |
| 2015/0339263 | A1 | 11/2015 | Abu El Ata et al. |
| 2017/0140306 | A1 | 5/2017 | Prabhu |
| 2017/0277841 | A1* | 9/2017 | Shankar .................. G16Z 99/00 |
| 2019/0005200 | A1* | 1/2019 | Zimmerman .......... G16H 50/30 |
| 2019/0188615 | A1 | 6/2019 | Liu |
| 2020/0387845 | A1 | 12/2020 | Aasoori et al. |
| 2021/0158897 | A1* | 5/2021 | Chatzou ................. G16B 40/30 |
| 2021/0294946 | A1* | 9/2021 | Hendriks ............... G16H 50/20 |
| 2022/0061745 | A1* | 3/2022 | Baldera ............. A61B 5/14546 |
| 2022/0375621 | A1* | 11/2022 | Cheng .................... G16H 50/50 |
| 2023/0024150 | A1* | 1/2023 | Malone ................... G16B 5/20 |
| 2023/0079951 | A1* | 3/2023 | Bulut ..................... G16H 50/20 600/300 |
| 2023/0215580 | A1* | 7/2023 | Sakata ................... G16H 50/80 705/2 |
| 2023/0360802 | A1* | 11/2023 | Jin ......................... G16H 50/70 |
| 2023/0394124 | A1* | 12/2023 | Cronie ................... G06F 21/32 |

OTHER PUBLICATIONS

L. Abirami and J. Karthikeyan, "Digital Twin-Based Healthcare System (DTHS) for Earlier Parkinson Disease Identification and Diagnosis Using Optimized Fuzzy Based k-Nearest Neighbor Classifier Model," in IEEE Access, vol. 11, pp. 96661-96672, 2023 (Year: 2023).*

Keshav, S., "Real User's Manual", Oct. 21, 1993, URL: http://minnie.cs.adfa.oz.au/REAL/user.asc.gz.

Lazowska, E., et al., "Quantitative System Performance: Computer System Analysis Using Queueing Network Models", Prentice-Hall, Inc., 1984, Table of Contents Only consisting of 8 pages.

Leymann, F., et al, "Production workflow: concepts and techniques", 2000, Table of Contents Only consisting of 14 pages.

Lorenz, "The Essence of Chaos," 1993, University of Washington Press, Chapter 2: a Journey Into Chaos, p. 69, 3rd-4th Paragraph.

Menasce, D., et al., "Capacity Planning and Performance Modeling", 1994, Prentice-Hall, ISBN 0- 13-035494-5.

Morrison, "The Art of Modeling Dynamic Systems: Forecasting for Chaos, Randomness, and Determinism," 1991, Turtle Hollow Associates, Inc.

"Model Driven Architecture (MDA) Document No. ormsc/2001-07-01", Architecture Board ORMSC1, pp. 1-31, Jul. 2001.

"Performance and Capacity Management, BEST/I-Visualizer for AS/400," http://www.bgs.com/as400/as4_home.htm (Printed: May 21, 1998), 2 pgs.

"Pyramid: Quantitative management: get a grip on software!" 100 pages, 1991.

Rechtin, E., "System Architecting", Creating and Building Complex Systems, Prentice Hall, 1991, Table of Contents only, consisting of 5 pages.

(56) References Cited

OTHER PUBLICATIONS

"Reengineering," from Wikipedia, the free encyclopedia, http://en.wikipedia.org/wiki/Reeingineering, downloaded Jan. 8, 2006, 2 pp.
Riolli, L., and Savicki, V. "Information System Organizational Resilience," Omega: The International Journal of Management Science (31 :3), 2003, pp. 227-233. (Year: 2003).
Rolia, J.A. and K.C. Sevcik, "The Method of Layers," IEEE Transactions on Software Engineering 21(8):689-700, Aug. 1995).
Sarris, D., et al., "The White Papers: Capacity Planning for e-Commerce Systems With Benchmark Factory™", http://www.guest.com/whitepapers/caP_plan_Ecomm.pdf, pp. 1-19. No date given.
"SES—Products and Services: Why Simulate?" http://www.ses.com/whysimulate.html (Updated: Apr. 2, 1998), 7 pgs. from Capacity Management Review, vol. 36, No. 2, Feb. 1998.
"SES in the Press," http://www.ses.com/news/html (Updated: Apr. 8, 1998), 3 pgs.
"SES Inc. Announces Release of Strategizer," http://www.ses.com/pr_archive/010297.html (Updated: Jul. 14, 1997, 2 pgs.
"SES Releases SES/Workbench 3.1," http://www.ses.com/pr_archive/022896.html (Updated Jul. 14, 1997), 3 pgs.
"SES/workbench: Workbench Overview," http://www.ses.com/workbench.html (Updated: Feb. 10, 1998), 3 pgs.
"SES/objectbench: Batch Execution," http://www.ses.com/Objectbench/sim_details_batch.html (Updated: Apr. 6, 1998), 2 pgs.
"SES/objectbench: The Objectbench Animated Simulator," http://www.ses.com/Objectbench/simulator.html (Updated: Apr. 15, 1998), 2 pgs.
"SES/objectbench," http://www.ses.com/Objectbench/index.html (Updated Apr. 6, 1998), 2 pgs.
Setzer, "Decision Support for Service Transition Management," 2008, In NOMS 2008-2008 IEEE Network Operations and Management Symposium, pp. 200-207 (Year. 2008).
Shaw, M., et al., "Software Architecture: Perspectives on an Emerging Discipline", Prentice Hall 1996, Table of Contents only consisting of 7 pages.
"Simulation modeling within workflow technology," Miller, et al., Proceedings of the 1995 Winter Simulation Conference, Dec. 3-6, 1995.
Soley, R., et al., "Model Driven Architecture" Object Management Group, pp. 1-12 (Nov. 27, 2000).
"The Portable Simulation Initiative and the Common Modeling Framework," http://www.ses.com/psi-cmf.html (Updated: Apr. 3, 1998), 3 pgs.
"UML Based Performance Modeling," Chapter 5, pp. 75-167; no date provided.
US. Trademark Electronic Search System, search result for Trademark U.S. Appl. No. 74/555,204, filed Nov. 27, 2001.
White, R.V., "An Introduction to Six Sigma with a Design Example," Applied Power Electronics Conference and Exposition, 1992. Conference Proceedings 1992, Seventh Annual, Fehr. 23-27, 1992, pp. 28-35.
Wickboldt, "Improving IT Change Management Processes with Automated Risk Assessment," 2009, In IEEE International Workshop on Distributed Systems: Operations and Management, pp. 71-84 (Year: 2009).
"About BEST/I," http://www.bgs.com/bgs.htm (Printed Out: May 21, 1998) 1 pg.
"Analyzing and re-engineering business process using simulation," Bhskar, et al., Proceeding of the 1994 Winter Simulation Conference, Dec. 11-14, 1994.
Abu El Ata, N., "How we Avoided Murphy's Law at the Italian Stock Exchange", CMG 1997, consisting of 7 pages.
Abu El Ata, N., "How Metrics and Models Made Architecture Real," presented at DCI Conference in Washington, D.C. in Feb. 2000 (slides 1-21).
Abu El Ata, N., "A Predictive Modeling Approach to Developing Complex Systems," presented at CSC Leading Edge Forum Conference on Mar. 6, 2001 (slides 1-32).

Abu El Ata, N., "System Performance Modeling", ITC Meeting Minutes, Dec. 2, 1999, URL: http://www.istis.unomaha.edu/itc/meetings/m991202.htm.
Abu El Ata, N., "CMG97 Session Descriptions by Subject Area", CMG97 Orlando, The Computer Measurement Group's 1997 Int'l Conference, Dec. 7-12, 1997, URL: http://www.cmg.org/cmg97/cmg97sessions.html and http://www.cmg.org/cmg97/97Workload.pdf.
Accretive/BT/Reuters, "Reuters, BT and Accretive Technologies Collaboration for Success," 2005, 1 p.
Agrawal, S., et al., "The aggregate server method for analyzing serialization delays in computer systems", ACM Transactions on Computer Systems, vol. 1, Issue 2, pp. 116-143, May 1983, ISSN: 0734-2071.
Altmann, M., "A list of software for computer simulations", Last updated, Nov. 11, 1996. URL: http://www.nmsr.labmed.umn.edu/~michael/dbase/outgoing/FAQ.html.
J. Barkley Rosser, Jr., "Computational and Dynamic Complexity in Economics" (Mar. 2007).
Bass, L., et al., "Software Architecture in Practice", SEI Series in Software Engineering, Addison-Wesley, 1998, Table of Contents only, consisting of 8 pages.
Beck, K., "Extreme Programming Explained", Addison-Wesley 2000, Table of Contents Only consisting-of 7 pages.
"BEST/I-Visualizer for AS/400, Product Description," http://www.bgs.com/as400/Slid_2.html (Printed Out: May 21, 1998), 2 pgs.
"BEST/I-Visualizer for AS/400, Bottleneck Detection and Analysis," http://www.bgs.com/as400/Slid_3.html (Updated: Nov. 22, 1996), 2 pgs.
"BEST/I-Visualizer for AS/400, Threshold Exception Reporting," http://www.bgs.com/as400/Slid_4.html (Updated: Jan. 23, 1997), 2 pgs.
"BEST/I-Visualizer for AS/400, Track and Trend Long-term Performance," http://www.bgs.com/as400/Slid_6.html (Printed Out: May 21, 1998) 2 pgs.
"BEST/I-Visualizer for AS/400, CPU/System Graphs," http://www.bgs.com/as400/Slid_8.html (Updated: Nov. 29, 1996, 2 pgs.
"BEST/I-Visualizer for AS/400, 1/0 Subsystem Graphs," http://www.bgs.com/as400/Slid_9.html (Updated: Nov. 30, 1996), 2 pgs.
"BEST/I-Visualizer for AS/400, Storage Pool Graphs," http://www.bgs.com/as400/Slid_11.html (Updated: Nov. 22, 1996), 2 pgs.
"BEST/I-Visualizer for AS/400, Communication Line Graphs," http://www.bgs.com/as400/Slid_12.html (Updated: Nov. 30, 1996), 2 pgs.
"BEST/I-Visualizer for AS/400, Job Graphs," http://www.bgs.com/as400/Slid_13.html (Updated: Jan. 22, 1997) 2 pgs.
"BEST/I-Visualizer for AS/400, Workload Analysis," http://www.bgs.com/as400/Slid_5.html (Updated: Jan. 23, 1997), 2 pgs.
"BMC Software BEST/I," http://www.bgs.com (Updated: Apr. 10, 1998), 1 pg.
"BMC Software to Acquire BGS Systems," http://www.bgs.com/bmcbgs.htm (Printed Out: May 21, 1998), 3 pgs.
Boehm, B., "Software Engineering Economics", Prentice Hall, 1981, Table of Contents only, consisting of 14 pages.
Bontempo, et al., "Database Management Principles and Products", Prentice Hall, Inc., 1995, Table of Contents only consisting of 10 pages.
Booch, G., et al., "The Unified Modeling Language User Guide", Addison Wesley Longman, Inc. 1999, Table of Contents only, consisting of 9 pages.
Chappell, D., "SOA: Is everyone talking the same language?", Issue 15.3, Nov. 2005, pp. 1-4 http://www.ibspublishing.com/index.cfm?section=features&action=view&id=987.
Choukri, T., "Curriculum Vitae", 1999. URL: http://www.global-coms.com/consultants/cv_choukri.htm. (With translation).
Compaq Open VMS Documentation, "TCP/IP Networking on Open VMS Systems", Nov. 1996, URL: http://www.openvms.compaq.com:8000/ssb71/6436p.htm.
EETimes: Intel, Others Eye Performance Modeling Standard, http://www.techweb.com/se/directlink.cgi? EET19971103S0105 (Nov. 3, 1997), 2 pgs.

(56) References Cited

OTHER PUBLICATIONS

Eureka Project E!636. URL: http://www3.eureka.be/Home/projectdb/PrjFormFrame.asp?pr_id=636; retrieved from the Internet on Nov. 27, 2001.

"Euroexpert: GATE™," Euroexpert SA, Antony, France (Sep. 1, 1997), 2 pgs.

"EuroExpert GATE™ Model Product Description: a predictive approach to efficient information systems", pp. 1-21, 1994.

"Euroexpert: Best Practices: Milan Stock Exchange," Euroexpert SA, Antony, Fanece (Sep. 1, 1997), 2 pgs.

"Euroexpert: Best Practices: France Telecom," Euroexpert SA, Antony, France (Sep. 1, 1997), 2 pgs.

"Euroexpert-Best Practices: French Social Security—UNEDIC", http://www.accretivetechnologies.com/documents/UNEDIC,PDF,EUROEXPERT and GATE (TM), 1992 Best Practices.

Grady, R., et al., "Software Metrics: Establishing a Company-Wide Program", Prentice-Hall, Inc., Table of Contents only, consisting of 5 pgs., 1987.

Gunther, N., "The Practical Performance Analyst", Performance-by-Design Techniques for Distributed Systems, McGraw-Hill, Table of Contents only consisting of9 pages, 1998.

Humphrey, W., "Managing the Software Process", SEI Series in Software Engineering, Addison-Wesley, 1990, Table of Contents only, consisting of 7 pages.

Hutchins, G., "ISO 9000, a Comprehensive Guide to Registration, Audit Guidelines, and Successful Certification" (Oliver Wight Publications, Inc.) 1993, Table of Contents Only consisting of 5 pages.

Jacobson, I., et al., "Software Reuse", Architecture Process and Organization for Business Success, ACM Press, Table of Contents only, consisting of9 pages, Addison-Wesley, 1997.

Kahkipuro, P., "Performance Modeling Framework for CORBA Based Distributed Systems," Department of Computer Science Series of Publications a Report A-2000-3, Finland, University of Helsinki (2000).

Kellert, "In the Wake of Chaos: Unpredictable Order in Dynamical Systems," 1993, University of Chicago Press.

Keshav, S., "Real 5.0 Overview", Aug. 13, 1997, URL: http://www.cs.comell.edu/skeshav/real/overview.html.

Keshav, S., "Real 5.0 User Manuals", Aug. 13, 1997, URL: http://www.cs.comell.edu/skeshav/real/user.html.

Keshav, S., "Real 5.0 Programmer's Manual", Aug. 13, 1997, URL: http://www.cs.cornell.edu/skeshav/real/prog.html.

Keshav, S., "Real 5.0 Changes", Aug. 13, 1997, URL: http://www.cs.comell.edu/skeshav/real/changes.html.

Keshav, S., "Real Programmer's Manual", Oct. 21, 1993, URL: http://minnie.cs.adfa.oz.au/REAL/prog.asc.gz.

* cited by examiner

OBTAIN BASE MODEL
205

OBTAIN HEALTH ATTRIBUTES
210

GENERATE PATIENT MODEL
215

GENERATE PLURAL SETS OF
PARAMETERS
220

MODEL HEALTH METRICS
UNDER PLURAL SETS OF
PARAMETERS
225

DETERMINE OCCURRENCE
PROBABILITY OF
SUCCESSIVE STATES
230

DETERMINE AND REPORT
RISK(S) OF DISEASE
235

200

400

| SYSTEM STATE 510 | RISK(S) 520 | REMEDIES 530 |
|---|---|---|
| STATE A | RISK METRICS A | REMEDY A |
| STATE B | RISK METRICS B | REMEDY B |
| STATE C | RISK METRICS C | REMEDY C |
| STATE D | RISK METRICS D | REMEDY D |
| STATE E | RISK METRICS E | REMEDY E |

500

IDENTIFY INTRODUCED
CHANGE(S) TO SET OF
PARAMETERS
905

IDENTIFY HEALTH/EXTERNAL
ATTRIBUTES MOST PROXIMATE
TO ADVERSE OUTCOME
910

TRACE PATH FROM INTRODUCED
CHANGE(S) TO ATTRIBUTES
915

IDENTIFY SERIES OF
ATTRIBUTES IN PATH
920

DIAGNOSE EACH OF SERIES OF
ATTRIBUTES FOR FAILURE,
DEGRADATION, CHANGES IN
BEHAVIOR
930

REPORT ATTRIBUTES CAUSING
ADVERSE OUTCOME
940

900

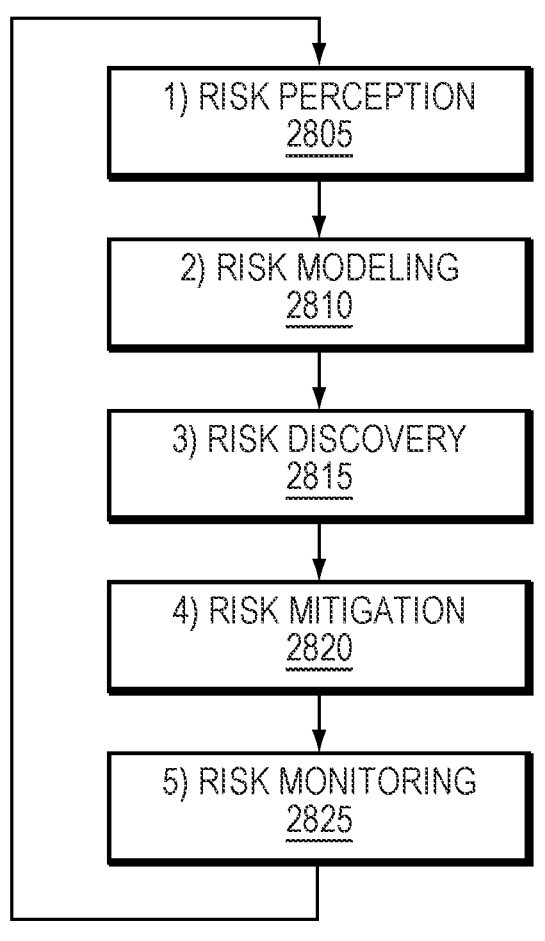
1) RISK PERCEPTION
2805
2) RISK MODELING
2810
3) RISK DISCOVERY
2815
4) RISK MITIGATION
2820
5) RISK MONITORING
2825
1000
FIG. 10

50, 60

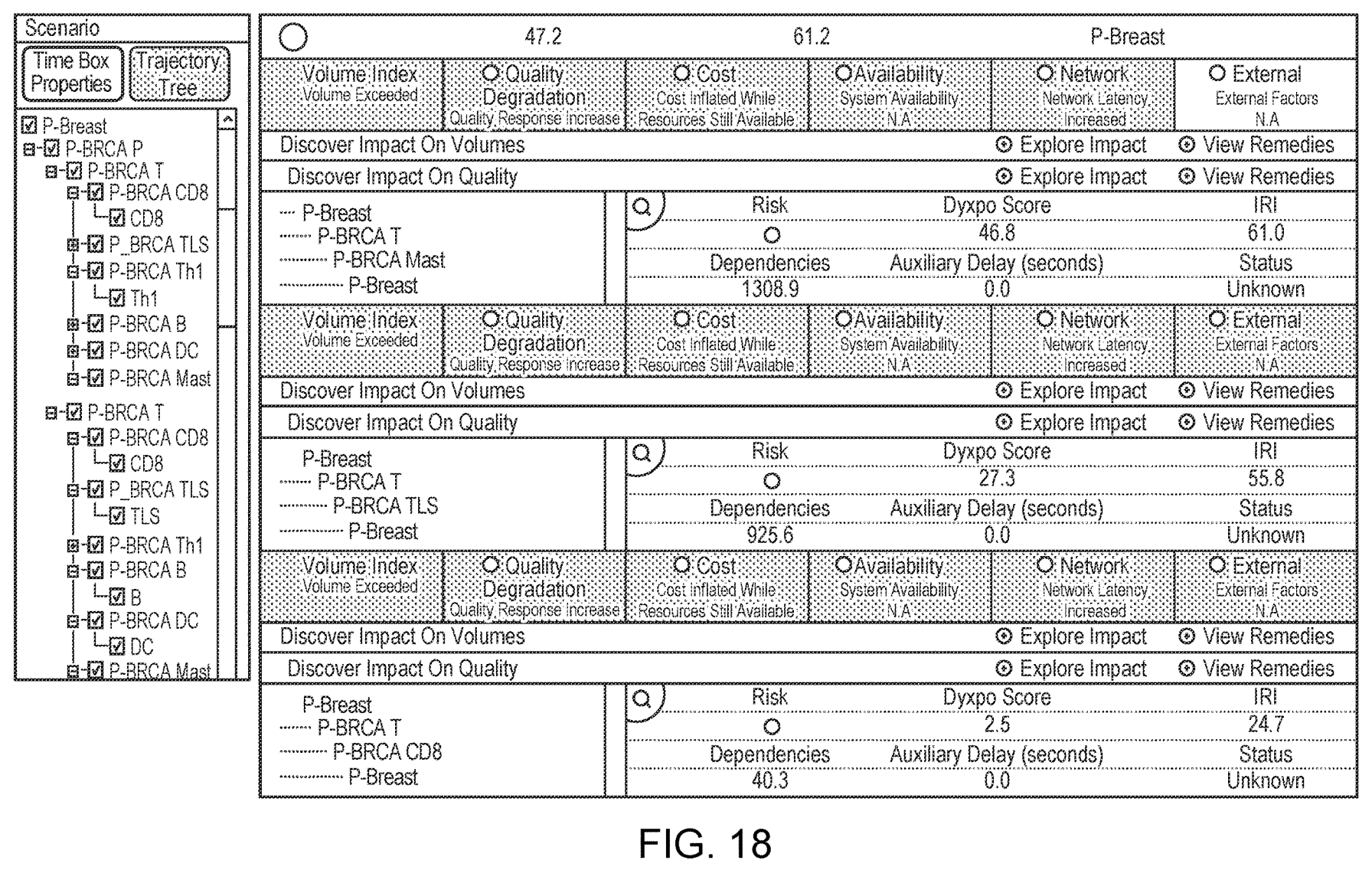

Scenario

Time Box Properties | Trajectory Tree

☑ P-Breast
⊞ ☑ P-BRCA P
⊞ ☑ P-BRCA T
⊞ ☑ P-BRCA CD8
    └ ☑ CD8
⊞ ☑ P_BRCA TLS
⊞ ☑ P-BRCA Th1
    └ ☑ Th1
⊞ ☑ P-BRCA B
⊞ ☑ P-BRCA DC
⊞ ☑ P-BRCA Mast ⊞ ☑ P-BRCA T
⊞ ☑ P-BRCA CD8
    └ ☑ CD8
⊞ ☑ P_BRCA TLS
    └ ☑ TLS
⊞ ☑ P-BRCA Th1
⊞ ☑ P-BRCA B
    └ ☑ B
⊞ ☑ P-BRCA DC
    └ ☑ DC
⊞ ☑ P-BRCA Mast P-Breast    47.2    61.2    P-Breast ○ Volume Index — Volume Exceeded
○ Quality Degradation — Quality Response Increase
○ Cost — Cost Inflated While Resources Still Available
○ Availability — System Availability N.A.
○ Network — Network Latency Increased
○ External — External Factors N.A.

Discover Impact On Volumes    ⊙ Explore Impact    ⊙ View Remedies
Discover Impact On Quality    ⊙ Explore Impact    ⊙ View Remedies

| | Risk | Dyxpo Score | IRI |
|---|---|---|---|
| --- P-Breast | ○ | 46.8 | 61.0 |
| ------ P-BRCA T | | | |
| --------- P-BRCA Mast | Dependencies | Auxiliary Delay (seconds) | Status |
| ------------ P-Breast | 1308.9 | 0.0 | Unknown |

○ Volume Index — Volume Exceeded
○ Quality Degradation — Quality Response Increase
○ Cost — Cost Inflated While Resources Still Available
○ Availability — System Availability N.A.
○ Network — Network Latency Increased
○ External — External Factors N.A.

Discover Impact On Volumes    ⊙ Explore Impact    ⊙ View Remedies
Discover Impact On Quality    ⊙ Explore Impact    ⊙ View Remedies

| | Risk | Dyxpo Score | IRI |
|---|---|---|---|
| P-Breast | ○ | 27.3 | 55.8 |
| --- P-BRCA T | | | |
| ------ P-BRCA TLS | Dependencies | Auxiliary Delay (seconds) | Status |
| --------- P-Breast | 925.6 | 0.0 | Unknown |

○ Volume Index — Volume Exceeded
○ Quality Degradation — Quality Response Increase
○ Cost — Cost Inflated While Resources Still Available
○ Availability — System Availability N.A.
○ Network — Network Latency Increased
○ External — External Factors N.A.

Discover Impact On Volumes    ⊙ Explore Impact    ⊙ View Remedies
Discover Impact On Quality    ⊙ Explore Impact    ⊙ View Remedies

| | Risk | Dyxpo Score | IRI |
|---|---|---|---|
| P-Breast | ○ | 2.5 | 24.7 |
| --- P-BRCA T | | | |
| ------ P-BRCA CD8 | Dependencies | Auxiliary Delay (seconds) | Status |
| --------- P-Breast | 40.3 | 0.0 | Unknown |

FIG. 18

| Risk | Dyxpo Score | IRI | Business trajectory | |
|------|-------------|-----|---------------------|---|
| ○ | 3.9 | 31.5 | Age | ∨ |
| ○ | 3.8 | 31.3 | N-Breast | ∨ |
| ○ | 3.8 | 31.3 | N-Hepatocellular | ∨ |
| ○ | 3.8 | 31.3 | N-Pancreatic | ∨ |
| ○ | 3.2 | 28.7 | P-Colorectal | ∨ |
| ○ | 3.1 | 28.5 | P-Prostate | ∨ |
| ○ | 3.1 | 28.5 | P-Head And Neck | ∨ |
| ○ | 3.1 | 28.5 | N-Head And Neck | ∨ |
| ○ | 3.1 | 28.5 | P-Biliary Tract | ∨ |
| ○ | 3.1 | 28.5 | P-Lung | ∨ |
| ○ | 3.1 | 28.5 | P-Breast | ∨ |
| ○ | 3.1 | 28.5 | P-Ovarian | ∨ |

FIG. 21

| Comorbidity Risk | Survivor/ non-Survivor | Arrival Rate 0 | Arrival Rate 1 | Arrival Rate 2 | Arrival Rate 3 | Arrival Rate 4 | Arrival Rate 5 | Arrival Rate 10 | Arrival Rate 20 |
|---|---|---|---|---|---|---|---|---|---|
| Exp_Hist | Survivor_Exp_Hist | 59.1 | 88.7 | 118.3 | 147.8 | 177.4 | 207.0 | 354.8 | 650.5 |
| BioMale | Non-Survivor_Male | 37.4 | 56.2 | 74.9 | 93.6 | 112.3 | 131.0 | 224.6 | 411.8 |
| BioFemale | Non-Survivor_Female | 16.0 | 24.1 | 32.1 | 40.1 | 48.1 | 56.2 | 96.3 | 176.5 |
| Hypertention | Non-Survivor_Hypertention | 35.8 | 53.7 | 71.7 | 89.6 | 107.5 | 125.4 | 215.0 | 394.1 |
| Diabetes | Non-Survivor_Diabetes | 25.7 | 38.5 | 51.3 | 64.2 | 77.0 | 89.8 | 154.0 | 282.4 |
| pulse125 | Infected_Pulse125 | 1.9 | 2.9 | 3.8 | 4.8 | 5.7 | 6.7 | 11.5 | 21.0 |
| chronicLung | Non-Survivor_Chronic_Lung | 12.8 | 19.3 | 25.7 | 32.1 | 38.5 | 44.9 | 77.0 | 141.2 |
| coronary_heart | Non-Survivor_Coronary_Heart | 16.6 | 24.9 | 33.2 | 41.4 | 49.7 | 58.0 | 99.5 | 182.4 |
| coronary_heart | Survivor_Coronary_Heart | 1.4 | 2.1 | 2.8 | 3.4 | 4.1 | 4.8 | 8.3 | 15.1 |
| chronicLung | Survivor_Chronic_Lung | 1.4 | 2.1 | 2.8 | 3.4 | 4.1 | 4.8 | 8.3 | 15.1 |
| chronicLung | Infected_chronicLung | 5.7 | 8.6 | 11.5 | 14.3 | 17.2 | 20.1 | 34.4 | 63.0 |
| Diabetes | Survivor_Diabetes | 19.3 | 28.9 | 38.5 | 48.1 | 57.8 | 67.4 | 115.5 | 211.8 |
| chronicKidney | Infected_chronic_Kidney | 1.9 | 2.9 | 3.8 | 4.8 | 5.7 | 6.7 | 11.5 | 21.0 |
| coronaryHeart | Infected_Coronary_Heart | 15.3 | 22.9 | 30.6 | 38.2 | 45.8 | 53.5 | 91.7 | 168.1 |
| smoker | Infected_smoker | 11.5 | 17.2 | 22.9 | 28.7 | 34.4 | 40.1 | 68.8 | 126.1 |
| smoker | Survivor_smoker | 5.5 | 8.3 | 11.0 | 13.8 | 16.5 | 19.3 | 33.0 | 60.5 |
| Hypertention | Survivor_Hypertention | 31.6 | 47.4 | 63.3 | 79.1 | 94.9 | 110.7 | 189.8 | 347.9 |
| pulse125 | Survivor_Pulse125 | 1.4 | 2.1 | 2.8 | 3.4 | 4.1 | 4.8 | 8.3 | 15.1 |
| Exp_Hist | Infected_Exp_Hist | 72.6 | 108.9 | 145.2 | 181.5 | 217.7 | 254.0 | 435.5 | 798.4 |
| pulse125 | Non-Survivor_Pulse125 | 2.1 | 3.2 | 4.3 | 5.3 | 6.4 | 7.5 | 12.8 | 23.5 |
| BioMale | Survivor_Male | 81.1 | 121.7 | 162.3 | 202.8 | 243.4 | 284.0 | 486.8 | 892.5 |
| respRate | Infected_respRate | 55.4 | 83.1 | 110.8 | 138.5 | 166.2 | 193.9 | 332.3 | 609.3 |
| Chronic_Kidney | Non-Survivor_Chronic_Kidney | 3.7 | 5.6 | 7.5 | 9.4 | 11.2 | 13.1 | 22.5 | 41.2 |
| BioFemale | Infected_Female | 72.6 | 108.9 | 145.2 | 181.5 | 217.7 | 254.0 | 435.5 | 798.4 |
| Diabetes | Infected_Diabetes | 36.3 | 54.4 | 72.6 | 90.7 | 108.9 | 127.0 | 217.7 | 399.2 |
| Exp_Hist | Non-Survivor_Exp_Hist | 13.9 | 20.9 | 27.8 | 34.8 | 41.7 | 48.7 | 83.4 | 153.0 |

FIG. 27

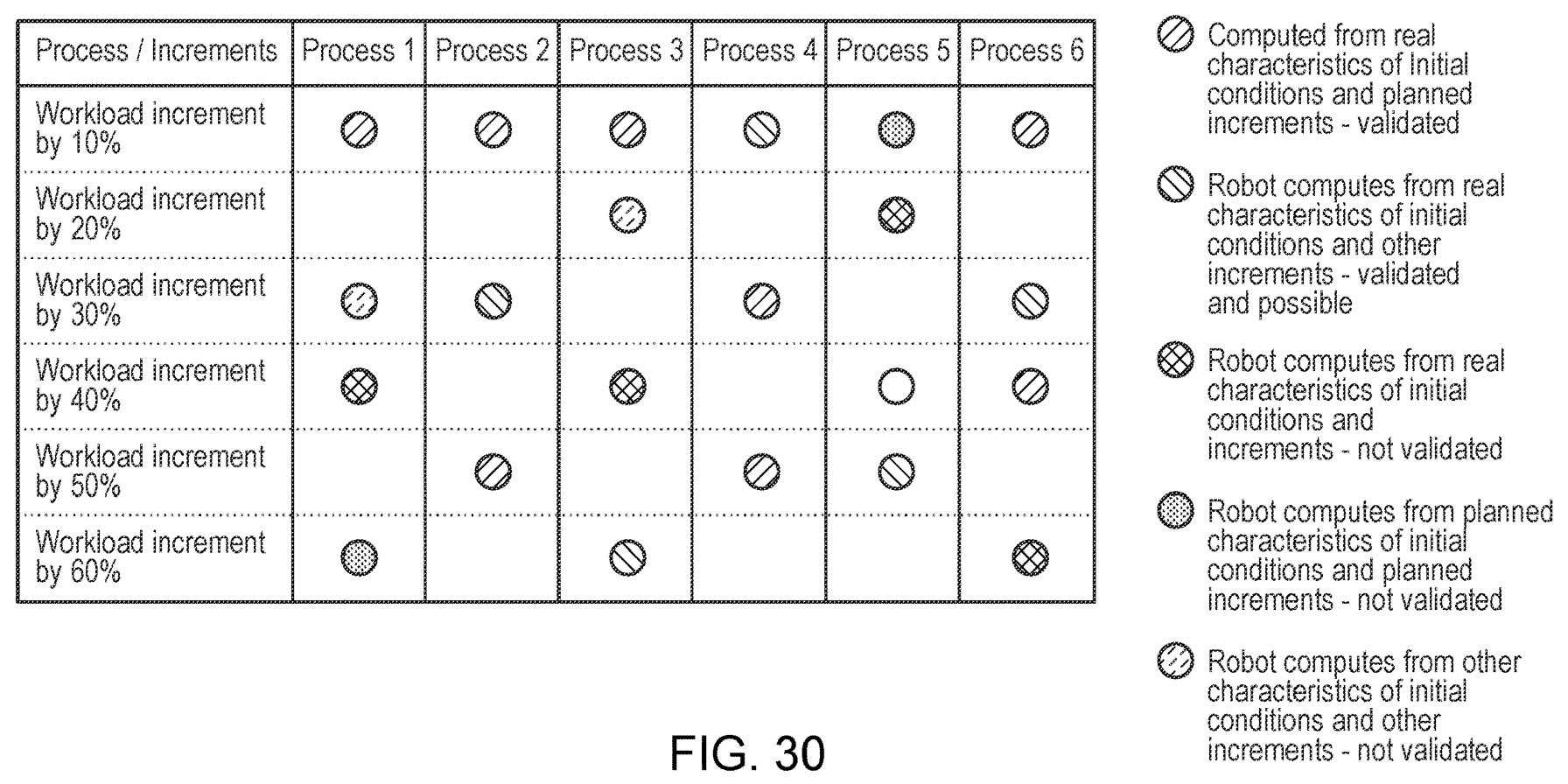

Legend:
- Computed from real characteristics of initial conditions and planned increments - validated
- Robot computes from real characteristics of initial conditions and other increments - validated and possible
- Robot computes from real characteristics of initial conditions and increments - not validated
- Robot computes from planned characteristics of initial conditions and planned increments - not validated
- Robot computes from other characteristics of initial conditions and other increments - not validated

| Process / Increments | Process 1 | Process 2 | Process 3 | Process 4 | Process 5 | Process 6 |
|---|---|---|---|---|---|---|
| Workload increment by 10% | ⊘ | ⊘ | ⊘ | ⊘ | ● | ⊘ |
| Workload increment by 20% | ⊘ | | ⊘ | | ⊗ | |
| Workload increment by 30% | ⊗ | ⊘ | ⊗ | ⊘ | | ⊘ |
| Workload increment by 40% | | ⊘ | | | ○ | ⊘ |
| Workload increment by 50% | ● | | ⊘ | ⊘ | ⊘ | |
| Workload increment by 60% | | | | | | ⊗ |

FIG. 30

PREDICTIVE RISK ASSESSMENT IN PATIENT AND HEALTH MODELING

RELATED APPLICATION

This application claims the benefit of U.S. Provisional Application No. 63/076,243, filed on Sep. 9, 2020. The entire teachings of the above application are incorporated herein by reference.

BACKGROUND

Foundationally, the nonlinearity of human health makes the pursuit of precision medicine particularly problematic. Current diagnostic and treatment analysis methods are based on analogy, statistics and mono-morbid approaches that ignore the complex topology of multimorbidity (i.e., the presence of multiple medical conditions). This introduces a high level of uncertainty into clinical practices, which translates into potential diagnosis errors and insufficient control over patient morbidity risks.

Developing technological solutions that enable clinicians to diagnosis and prescribe therapeutics with higher certainty and more optimal patient outcomes is important to satisfy the goals of precision medicine. Traditional medicine has focused on population averages and analogies to define common diagnosis and therapeutics, which in many cases may not be the optimal solution under different patient circumstances. To solve this dilemma, precision medicine strives to maximize efficacy and minimize toxicity of therapies for an individual patient. However, a high level of uncertainty is an inescapable outcome when experience or static data is used to infer a patient outcome based on the averages of a sample population. Because human health is dynamically complex, any analysis based on population averages will always be missing some circumstantial data that may be important to correctly diagnose and treat a particular patient case, especially in complex and ambiguous cases.

SUMMARY

Example embodiments include a computer-implemented methods and computer-readable mediums that provide for the modeling of a patient's health through multiple scenarios. Initially, a base model is obtained. The base model may be a mathematical model incorporating rules that govern a response by the human being to one or more diseases, as well as a relation between health metrics and the diseases. The health metrics may include one or more health metrics as described herein, including a resistance metric that indicates a measure of the patient's resistance to one or more diseases. A further health metric described below is human health dependability (HHD), which is a measure of an integrity of the patient's immune system to counteract the disease.

Health attributes of the patient may then be obtained. The health attributes may include a range of data, test results, evaluation and analysis of the patient, including genetic traits, a blood lipid profile, medical imaging reports, medical records detailing the patient's medical history, and the patient's environment (e.g., climate, location, and related external factors that may affect the patient's health). From the base model and the health attributes, a patient model (also referred to as a "digital twin") may be generated. The patient model may incorporate some or all of the base model and a representation of the health attributes into the health dependency graph.

Once the patient model is complete, it may be modeled (simulated) under plural sets of parameters. The plural sets of parameters may be previously generated as detailed with reference to the example embodiments described below, and each of the plural sets of parameters may indicate respective variables having a causal relation to the health metrics. For example, one set of parameters may represent exposure of the patient to a disease, a change in the patient's health attributes based on known trends within the population of the patient's environment, an injury suffered by the patient, and other changes relating to the patient or the patient's environment that may affect the patient's health. Further sets of parameters may represent a control scenario (i.e., a continuation of the patient's experience without introduction of health-affecting variables), as well as one or more interventions (e.g., scenarios in which a patient makes positive changes to his/her health attributes, such as quitting smoking, changing a diet or exercise routine, engaging in physical therapy, or taking a medication). The health metrics of the patient model are then modeled under the plural sets of parameters to generate respective health metrics (e.g., resistance metric, HDD).

From an analysis of the plural sets of parameters and the resulting health metrics, occurrence probabilities for each of the sets of parameters can be determined. The occurrence probabilities may indicate predicted probabilities of the patient model transitioning from an initial state to each of a plurality of successive states, each of the successive states corresponding to a respective one of the plural sets of parameters. Some of those successive states may be identified to relate to an adverse outcome, such as a diseased state representing the patient being afflicted by a disease, or an outcome wherein the patient's health metrics decrease below a given threshold. Accordingly, one or more risks may also be identified, wherein the risks indicate a likelihood of the patient transitioning from the initial state (corresponding to the initial health attributes) to an adverse outcome such as a diseased state. Based on those findings, a report may be generated for the patient. The report may indicate the identified risks, and may also provide a diagnosis of the patient and one or more remedies/interventions that are predicted, based on the plural sets of parameters and resulting health metrics, to avoid or prevent an adverse outcome.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 10 is a state diagram illustrating a process for patient risk management in one embodiment.

FIG. 18 illustrates an example of parameter selection and computations based on immune cells and cancer types.

FIG. 21 illustrates an example model computation result.

FIG. 27 is a table providing an example of a sensitivity analysis.

FIG. 30 illustrates an example of scenario computations.

DETAILED DESCRIPTION

Figure 1:
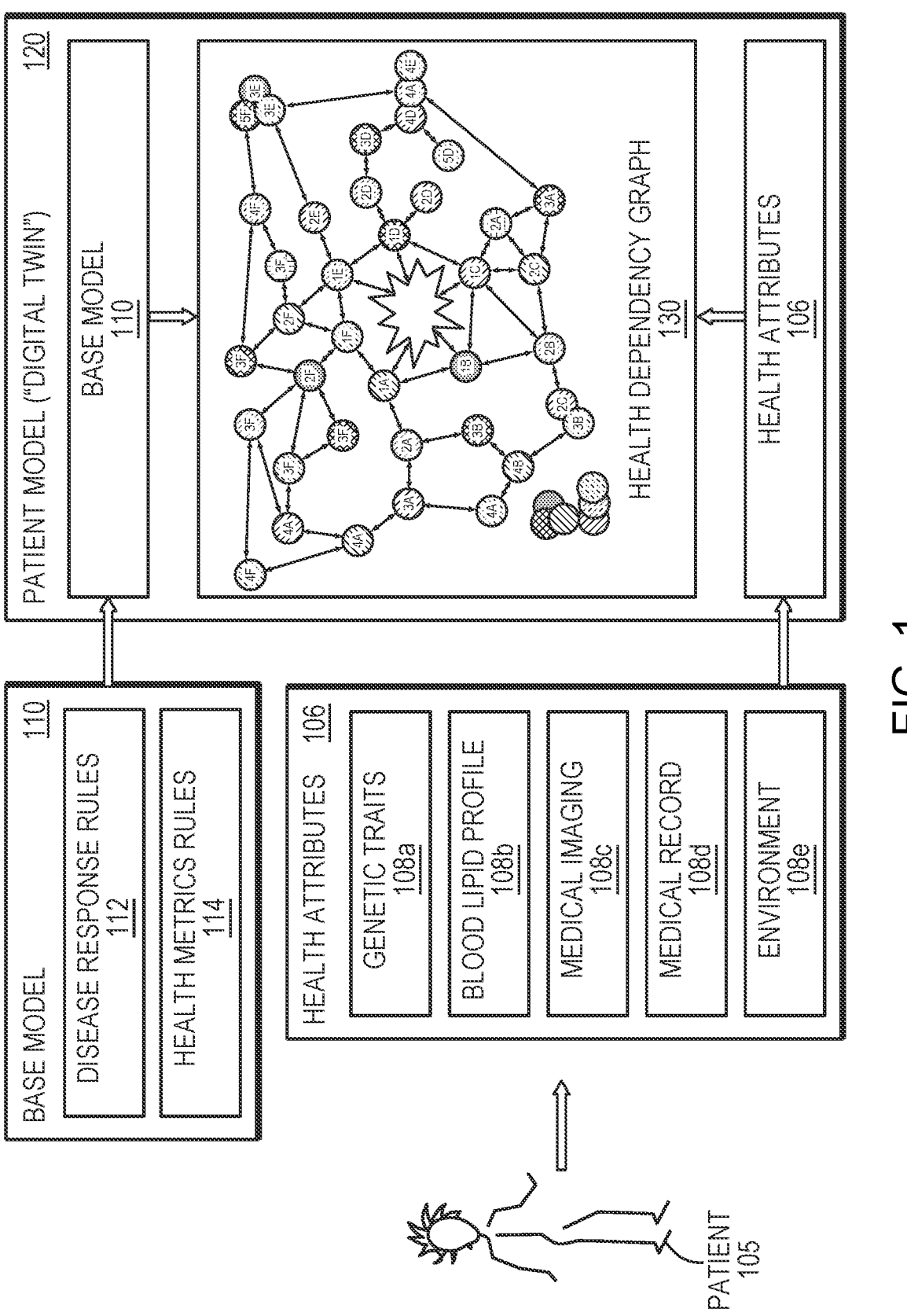
FIG. 1 is a block diagram illustrating generation of a patient model in one embodiment.

A description of example embodiments follows.

Developing artificial intelligence (AI) solutions that enable clinicians to diagnosis and prescribe therapeutics with higher certainty and more optimal patient outcomes is critically important to satisfy the goals of precision medicine. Traditional medicine has focused on population averages and analogies to define common diagnosis and therapeutics, which in many cases may not be the optimal solution under different patient circumstances. To solve this dilemma, precision medicine strives to maximize efficacy and minimize toxicity of therapies for an individual patient.

Unfortunately, a high level of uncertainty is an inescapable outcome when experience or static data is used to infer a patient outcome based on the averages of a sample population. Because human health is dynamically complex, any analysis based on population averages is likely to miss some circumstantial data that may be important to correctly diagnose and treat a particular patient case, especially in complex and ambiguous cases.

Collecting more data does not necessarily improve the analysis. This is because errors in the data itself or incorrect assumptions can throw a model widely off course. Also, the data analysis is static, and therefore cannot account for factors that define how multimorbidity may evolve over time. Introducing machine learning (ML) to deal with data-mining and predictive analysis cannot in and of itself solve these shortcomings. The layering of ML under such circumstances can further amplify uncertainties derived from probabilistic methods. These uncertainties support a perception that the use of AI in clinical decision-making is highly risky and therefore unattractive/unreliable.

In order to move precision medicine from concept to value in clinical applications, it is necessary to gain better control of diagnostic and therapeutic risks. If it were possible to reliably expose the circumstances that lead to an undesirable patient outcome, then clinicians could monitor and prescribe treatments to avoid these high-risk scenarios. Example embodiments, described herein, provide a patient model, also referred to as a Human Digital Twin (HDT), for such solutions. A digital twin is commonly defined as a software model of a physical asset, system or process designed to detect, prevent, predict, and optimize through real time analytics. HDT extends the concept of digital twin to cover the mathematical replication of human health process dynamics.

To be effective for clinical practice, HDT should be proven to reliably predict morbidity risks and therapeutic efficacy for an individual patient. Predicting outcomes for an individual instead of average populations necessitates the development and applied use of deterministic models, like those used in mathematically oriented scientific fields, such as physics and engineering, as the preferred way to analyze and predict the behavior of multidimensional nonlinear systems.

Currently, stochastic models are often used instead of deterministic models in healthcare applications because it can be difficult to predict the outcome (dependent variable) for a particular input due to a lack of understanding and/or historical knowledge. This lack of knowledge makes the model imperfect and introduces uncertainty because a given value of the independent variable can generate a different value of the dependent variable each time the model is computed. As such, it is difficult for users to maintain confidence in the predictive results for critical decision making.

Using a deterministic model could potentially limit uncertainty in clinical use cases because it provides a mathematical representation in which every variable alters according to a mathematical formula versus random fluctuations. So, unlike stochastic models, a deterministic model will always produce the same output from a given starting condition or initial state. For this reason, a deterministic approach can help build the requisite trust in HDT analysis, which in turn would support its adoption in clinical AI applications.

Traditionally, medical researchers and clinicians have sought to understand and diagnose morbidity using statistics, categorization and recognition of repeating patterns. While these methods have evolved from simple analogies to complex computer run Bayesian models (that use a statistical interpretation of probability), clinical diagnoses today are still made by drawing probabilistic inferences based on incomplete, and often out of date, patient information compared to mono-morbid population-based data.

Diagnostic uncertainty is common in clinical practice and affects both healthcare providers and patients. Diagnostic uncertainty is defined as, "subjective perception of an inability to provide an accurate explanation of the patient's health problem." Diagnostic uncertainty has clinical consequences. It has been associated with a reluctance to withdraw intensive therapy and a propensity to order more tests and refer to specialists more often, unnecessary surgeries, more hospitalizations and referrals, thus increasing health care costs and resulting in a bias toward overuse of high-technology medicine. Inappropriate management of diagnostic uncertainty contributes to diagnostic errors or excess health care utilization and can impact both system and patient outcomes.

If clinicians want to factor in how genes, autoimmune responses, environment, and lifestyle choices may influence multimorbidity for an individual patient, then they need new ways to simplify and improve their confidence in choosing the right patient diagnosis. To accomplish this goal, clinicians will need access to AI technologies and robust modeling approaches that are suited to deal with the high degree of complexity arising from the presence of multiple diseases, their biological and non-biological determinants as well as the consequences, and multiple internal and external interactions in time and space.

Deterministic modeling methods already used in mathematically oriented scientific fields, such as physics and engineering, may be usefully applied to emulate human health as it continuously changes over time due to the influence of interdependent systems. Example embodiments, described herein, provide the HDT and deterministic modeling approaches in medical diagnosis applications, and can support the goals of precision medicine and overcome many obstacles preventing the adoption of AI in clinical practices. To this end, there are a significant number of opportunities as well as challenges that researchers, technologists and clinicians must work together to address.

FIG. 1 is a block diagram illustrating generation of a patient model 120, also referred to as a Human Digital Twin (HDT), in one embodiment. The patient model 120 may be generated from a base model 110, as well as health attributes 106 about a human patient 105. The health attributes 106 may be collected through one or more interactions with the patient 105, such as a survey, a medical examination, and other tests and investigations. Example health attributes 106 include genetic traits 108a (e.g., obtained by a genetic test of the patient 105), a blood lipid profile 108b, medical imaging results 108c (e.g., an X-ray image, a magnetic resonance imaging (MM) representation, a computed tomography (CT) scan representation), medical records 108d (e.g., a history of the patient's health, including lifestyle habits such as diet and smoking habits), and information on the patient's environment (e.g., health factors that are particular to the location of the patient's home or workplace).

The base model 110 may be a mathematical model incorporating rules that govern a response by the human being to one or more diseases, as well as a relation between health metrics and the diseases. The base model 110 may be constructed according to the process described below with reference to FIG. 6, and so may incorporate definitions of both static and dynamic complexity. Further, the base model 110 may be structured as a dependency graph, described in further detail below, representing rules 112, 114. The disease response rules 112 may govern a response by the human being to one or more diseases. Such diseases, as defined herein, may encompass one or more of a range of human-afflicting pathologies, including cancers, viral infections, bacterial infections, disorders (including mental disorders, physical disorders, metabolic disorders, genetic disorders, emotional and behavioral disorders, and functional disorders), syndromes, injuries, and medical conditions. For example, the disease response rules 112 may incorporates rules that govern a response by the human being to immune reactivations, autoimmunity, preexisting conditions and environmental influences.

Further, health metrics rules 114 may provide rules that govern a relation between health metrics and the diseases. Health metrics may include one more metrics that indicate respective levels of health of a patient. For example, a resistance metric may indicate a measure of the patient's resistance to one or more diseases, and human health dependability (HHD) may be a health metric that provides a measure of an integrity of the patient's immune system to counteract the one or more diseases. Such health metrics may correspond to a single disease, or may give a more general estimation of the patient's health, fitness or capability of resisting a range of given diseases. The health metrics rules 114 may govern how the patient's health attributes, a change in those health attributes, and potential affliction of diseases affect the health metrics. For example, the health metrics rules 114 may include a set of rules that govern a resistance metric indicating a patient's resistance to arteriosclerosis. The set of rules may determine this resistance metric as a function of a blood lipid profile (e.g., profile 108b). Thus, certain aspects of the blood lipid profile, such as C reactive protein, may raise or lower the resistance metric depending on their value (e.g., absolute value, relative value, or position above or below a threshold), indicating an increase or decrease in the patient's ability to resist (e.g., avoid diagnosis of) arteriosclerosis.

The patient model 120 may incorporate some or all of the base model 110 and a representation of the health attributes 106 into a health dependency graph 130, examples of which are described in further detail below. The patient model 120 may be configured to represent the patient 105 at a given point in time (e.g., when the health attributes 106 are collected), and may be updated as newer health attributes are collected from the patient 105.

Figure 2:
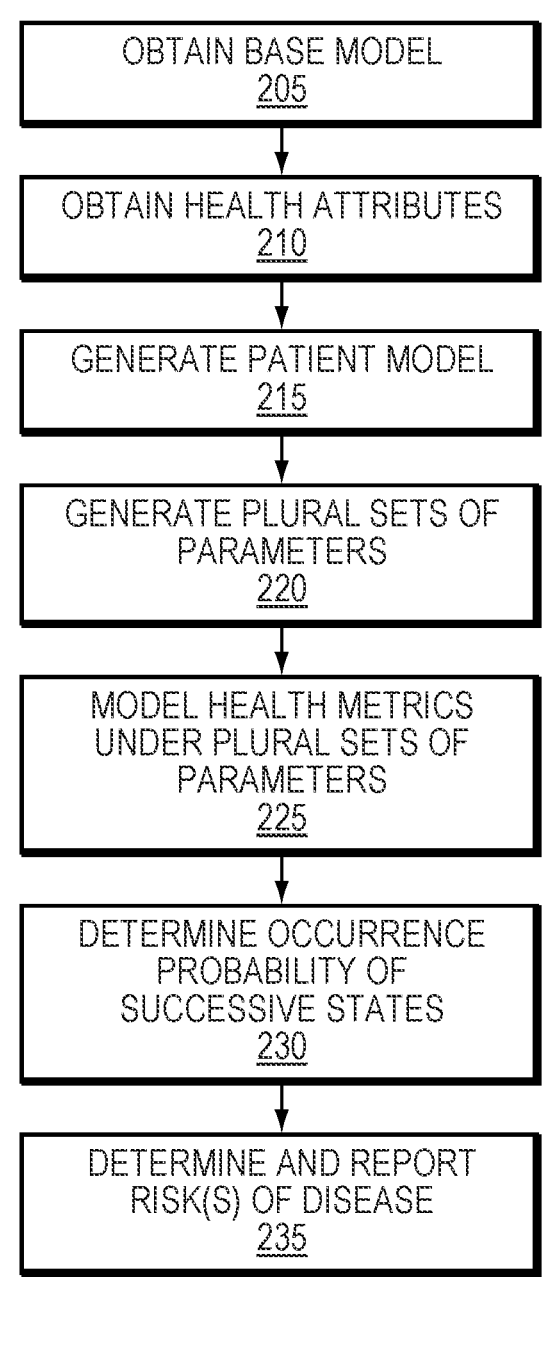
FIG. 2 is a flow diagram of a process of configuring and operating a patient model in one embodiment.

FIG. 2 is a flow diagram of a computer-implemented process 200 of configuring and operating a patient model in one embodiment. The process 200 may incorporate features of the processes for emulating a patient and identifying adverse outcomes as described below with reference to FIGS. 6-10. Further, the process 200 may be incorporated into the process described below with reference to FIG. 6, and in particular expands upon the features of driving an emulator and identifying root causes and defining improvements.

With reference to FIG. 1, initially, a base model is obtained (205). The base model 110 may be a mathematical model incorporating rules that govern a response by the human being to one or more diseases, as well as a relation between health metrics and the diseases. The health metrics may include one or more health metrics as described herein, including a resistance metric that indicates a measure of the patient's resistance to one or more diseases. A further health metric described below is human health dependability (HHD), which is a measure of an integrity of the patient's immune system to counteract the disease. The base model 110 may be constructed according to the process described below with reference to FIG. 6, and so may incorporate definitions of both static and dynamic complexity. Further, the base model 110 may be structured as a dependency graph, described in further detail below, representing the rules 112, 114.

Health attributes 106 of the patient 105 may then be obtained (210). The health attributes may include a range of data, test results, evaluation and analysis of the patient 105, including genetic traits 108*a*, a blood lipid profile 108*b*, medical imaging reports 108*c*, medical records 108*d* detailing the patient's medical history, and the patient's environment 108*e* (e.g., climate, location, and related external factors that may affect the patient's health). From the base model 110 and the health attributes 106, a patient model 120 (also referred to as a "digital twin") may be generated (215). The patient model 120 may incorporate some or all of the base model 110 and a representation of the health attributes 106 into the health dependency graph 130.

Once the patient model 120 is complete, it may be modeled (simulated) under plural sets of parameters. The plural sets of parameters may be previously generated as detailed with reference to the example embodiments described below (220), and each of the plural sets of parameters may indicate respective variables having a causal relation to the health metrics. For example, one set of parameters may represent exposure of the patient to a disease, a change in the patient's health attributes based on known trends within the population of the patient's environment, an injury suffered by the patient, and other changes relating to the patient or the patient's environment that may affect the patient's health. Further sets of parameters may represent a control scenario (i.e., a continuation of the patient's experience without introduction of health-affecting variables), as well as one or more interventions (e.g., scenarios in which a patient makes positive changes to his/her health attributes, such as quitting smoking, changing a diet or exercise routine, engaging in physical therapy, or taking a medication). The health metrics of the patient model 120 are then modeled under the plural sets of parameters to generate respective health metrics (e.g., resistance metric, HDD) (225).

From an analysis of the plural sets of parameters and the resulting health metrics, occurrence probabilities for each of the sets of parameters can be determined (230). The occurrence probabilities may indicate predicted probabilities of the patient model transitioning from an initial state to each of a plurality of successive states, each of the successive states corresponding to a respective one of the plural sets of parameters. Some of those successive states may be identified to relate to an adverse outcome, such as a diseased state representing the patient being afflicted by a disease, or an outcome wherein the patient's health metrics decrease below a given threshold. Accordingly, one or more risks may also be identified, wherein the risks indicate a likelihood of the patient 105 (represented by the model 120) transitioning from the initial state (corresponding to the initial health attributes 106) to an adverse outcome such as a diseased state. Based on those findings, a report may be generated for the patient 105 (235). The report may indicate the identified risks, and may also provide a diagnosis of the patient 105 and one or more remedies/interventions that are predicted, based on the plural sets of parameters and resulting health metrics, to avoid or prevent an adverse outcome. Example processes for determine such diagnoses and remedies are described in further detail below.

Example embodiments, as described herein, provide emulating a patient model 120 through a number of differing scenarios, where the results of such emulations can be analyzed to identify health-related concerns (e.g., susceptibility to a disease) and potential remedies for the patient. One aspect of this emulation, as described above, is to generate plural sets of parameters (220). In order to generate those sets of parameters, a set of input parameters may be permutated, by altering one or more values, to generate one or more additional scenarios for emulation. Such selection of differing parameters is described herein, and in particular with reference to FIG. 7. When selecting input parameters to detect an adverse outcome resulting from a patient model's dynamic complexity, a number of variables can be selected for permutation. For example, input parameters can be permutated to simulate the patient catching a given disease, a change in one or more of the patient's health attributes (e.g., a change in the patient's blood lipid profile, a change in the patient's lifestyle or environment), an acute adverse outcome such as an injury, and/or one or more interventions, such as treatment of physical therapy, a medication, or a positive lifestyle change (e.g., quitting smoking, beginning an exercise routing or diet). Further, the length of time over which the model patient is emulated may be varied, and this variation may be managed by an AI process based on the outcomes to be investigated. Such variation in time may be employed, with or without other permutations, to determine whether the input parameters result in an adverse outcome over a different (e.g., longer) length of time.

In an example embodiment, a first of the sets of parameters may correspond to an initial state of a patient (e.g., corresponding to measured health attributes at an initial point in time), or may correspond to a hypothetical or predicted state of the patient. Further, additional instances of the sets of parameters may correspond to a range of permutations of the first set of parameters, which may correspond to deviations from the initial state of the patient. Such deviations can include the permutations described above.

With the sets of parameters defined, the model may then be simulated under each of the sets of parameters to generate corresponding sets of health metrics (225). The sets of health metrics may also include a dimension of time (referred to, for example, as time "T1"), indicating that the results correspond to the first set of input parameters upon simulation for a given length of (simulated) time. Following obtaining resulting health metrics, those metrics may be analyzed, as described above with reference to FIGS. 7-9, to identify one or more adverse outcomes. The health metrics can be analyzed further, as described below with reference to FIG. 9, to identify the cause or causes of the modeled results. The steps of simulation and analysis (220-230) may be repeated, with further permutations, to determine performance (e.g., a new set of health metrics and risk estimation) and identify adverse outcomes under a range of scenarios corresponding to different input parameters.

Given the identified adverse outcome(s), a map can be generated to relate the adverse outcome(s) to corresponding instances of the plural sets of parameters. An example map is described below with reference to FIG. 3. Based on this map, one or more risks can be determined and reported, where the risk(s) define a probability of an outcome including an adverse outcome. In particular, the risk may be calculated based on the occurrence probability of each of the instances of the plural sets of parameters that are related to the identified adverse outcomes. The risks may then be reported to a user in a manner comparable to the reporting as described above (235), and may be provided for further analysis as described in further detail below with reference to FIGS. 4 and 10. Reports can include a metric representing risk (e.g., risk index).

Figure 3:
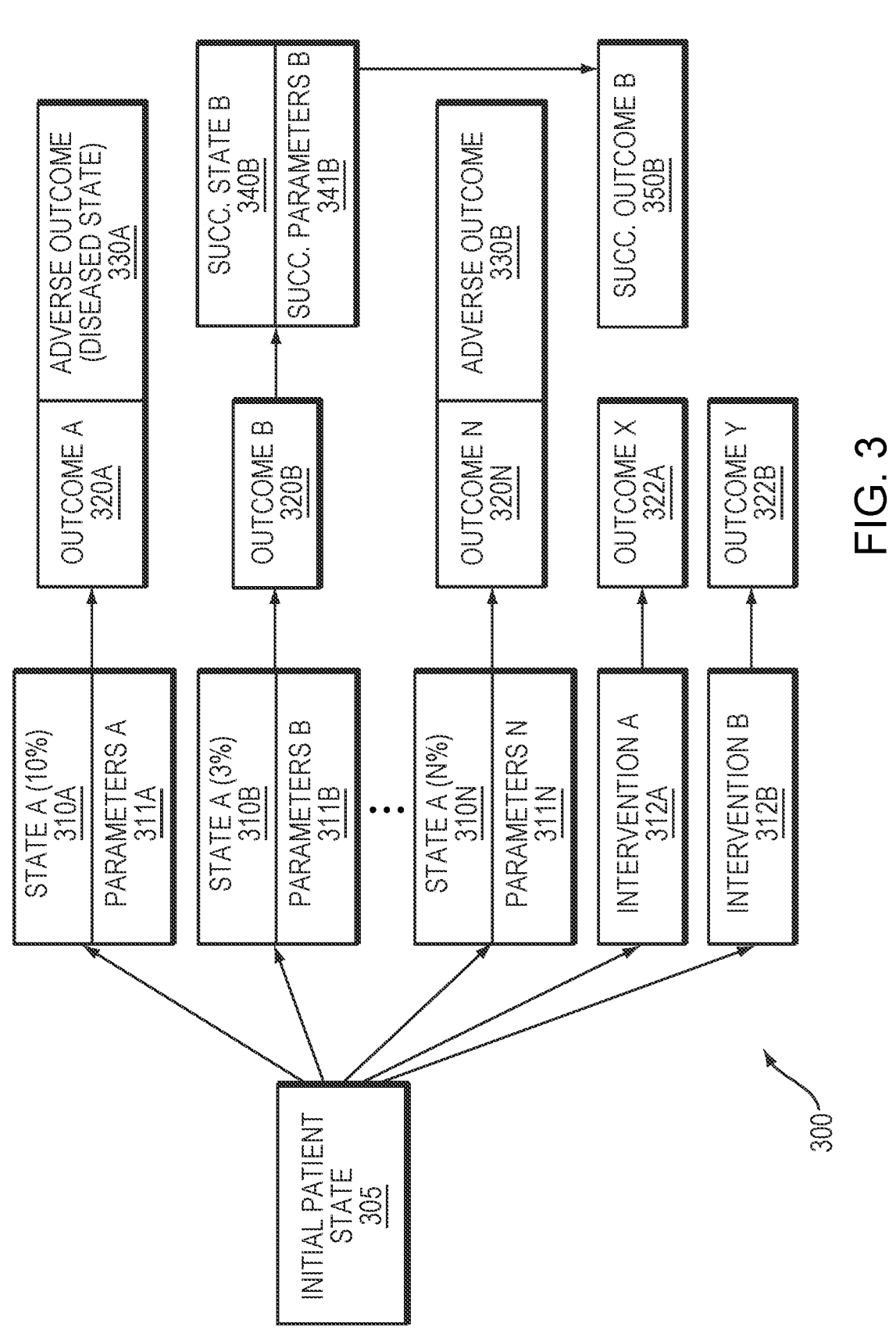
FIG. 3 is a diagram of a map relating parameters and outcomes in one embodiment.

FIG. 3 is a diagram of a map 300 relating parameters and outcomes in one embodiment. The map 300 may be generated as a result of the process 200 described above with reference to FIG. 2, and connects an initial patient model state 305 to a range of successive patient states 310A-N each having a respective set of parameters 311A-N, which in turn are related to corresponding outcomes 320A-N and, where applicable, corresponding adverse outcomes 110A-B. The adverse outcomes 110A-B can include a diseased state (e.g., 110A) indicating that the patient model exhibits a given disease, and other negative or potentially harmful results, such as health metrics that exceed a given threshold or updated health attributes that indicate a decline in health. In addition to the successive states 310A-N, the map 300 may also account for interventions 312A-B. The interventions 312A-B may be comparable to the state/parameter pairs in that they represent a respective set of parameters and a resulting state representing the patient model. However, the interventions 312A-B, along with their respective outcomes 322A-B, are shown separately to highlight the range of scenarios that may be simulated in example embodiments. The interventions 312A-B, in particular, may indicate parameters that represent scenarios in which one or more positive changes are made to the health attributes, such as quitting smoking, changing a diet or exercise routine, engaging in physical therapy, or taking a medication. In one example, an intervention 312A may represent a specific medication or lifestyle change prescribed by a medical professional with the purpose of treating or preventing a given disease. The intervention 312A may be proposed and simulated after one or more prior simulations (e.g., under parameters 311A-N) are found to indicate a risk of the patient becoming afflicted with the given disease.

The parameters 311A-N may correspond to each of the scenarios modeled as described above, and the outcomes 320A-N may include corresponding health metrics resulting from the modeling. Further, if an adverse outcome (e.g., diseased state 110A) is identified from modeling the patient model under a given set of parameters, the adverse outcome is associated with the outcome (e.g., outcome 320A), thereby "flagging" the outcome. Over a range of different (e.g., permutated) parameters 310A-N, some of the corresponding outcomes 320A-N may be associated with adverse outcomes 110A-B, while others may not. In an alternative embodiment, a map may be generated to include only outcomes that are associated with adverse outcomes.

From the map 300, one or more risks to the patient model can be determined. A risk, as described above, may indicate a probability that the patient model will encounter an outcome that includes an adverse outcome such as a diseased state. Such risks can be calculated through a number of means and may be expressed in a number of different ways, and examples of such analysis and presentation are provided in further detail below. In one example, an occurrence probability may be assigned to each of the successive states 310A-310N, where the occurrence probability indicates a likelihood that the patient model will move from the initial state 305 to a state having the given parameters. For example, the state 310A is assigned an occurrence probability of 10%, indicating that the patient model has a 10% chance of transitioning to the state 310A, under which the patient model is simulated under the corresponding parameters 311A. Such an occurrence probability may be determined based on historical data about the patient model, epidemiological data (e.g., data derived from a given population that relates health attributes and incidences of various changes exhibited by the population), historical simulation data, data about comparable patient models, the patient's health attributes, and/or other sources. Based on the occurrence probability of each of the states 310A-N, one or more risks (e.g., the probability of an outcome including one or more of the adverse outcomes 110A-B) can be determined. The risks may be reported to a user, including details of the predicted adverse outcomes and the likelihood of each. The risks may also be further processed, for example, to generate a lookup table, an example of which is described below with reference to FIG. 5.

As shown, the map 300 may depict two points in time: the initial patient state 305 representing the patient at an initial point in time (T1), and the successive patient states 310A-N (and interventions 312A-B) representing the potential outcomes for a patient at a later point in time (T2). Although the successive states 310A-N may represent different potential outcomes at a common point in time, they may instead represent different points in time. For example, state 310A may represent at an earlier simulated point in time than state 310B because the simulation reveals that the state 310A results in the adverse outcome 110A, and as such, the modeling of the state 310A may be terminated earlier, while state 310B may be simulated for longer to ensure that the outcome 320B does not include an adverse outcome.

Further, any of the simulated scenarios involving the successive states 310A-N (and/or interventions 312A-B) may be extended beyond those successive states to predict a state and outcome of the patient model at a still later point in time (T3). For example, as shown in FIG. 3, state 310B results in the health metrics of outcome 320B at time T2. Those health metrics, in turn, may be applied to the patient model, and the patient model may then be modeled under successive state 340B with successive parameters 341B, which may be the same or different from parameters 311B. As a result, a successive outcome 350B, indicating a predicted state of the patient model at time T3 in response to imposing the successive parameters 341B, may be determined. Alternatively, for successive simulations, any of the successive states 310A-N (or interventions 312A-N) may be implemented in place of the initial patient state 305, meaning that the patient model may be configured with health attributes based on the health metrics indicated by the outcome associated with the successive state. For example, state 310B may be configured as a new initial state with health attributes in accordance with outcome 320, and the patient model may be simulated under transitions to the plurality of successive states 310A-N, producing corresponding outcomes and indications of risk of adverse outcomes. Thus, the patient model can be simulated under one or more series of successive scenarios, which can provide 1) a predicted outcome that is responsive to multiple changes to the patient model (e.g., health attributes, health metrics, interventions) over time, and/or 2) a branching series of scenarios, originating from a single initial patient state, that accounts for several sets of parameters and predicts a range of potential outcomes for each scenario following multiple changes to the patient model.

Figure 4:
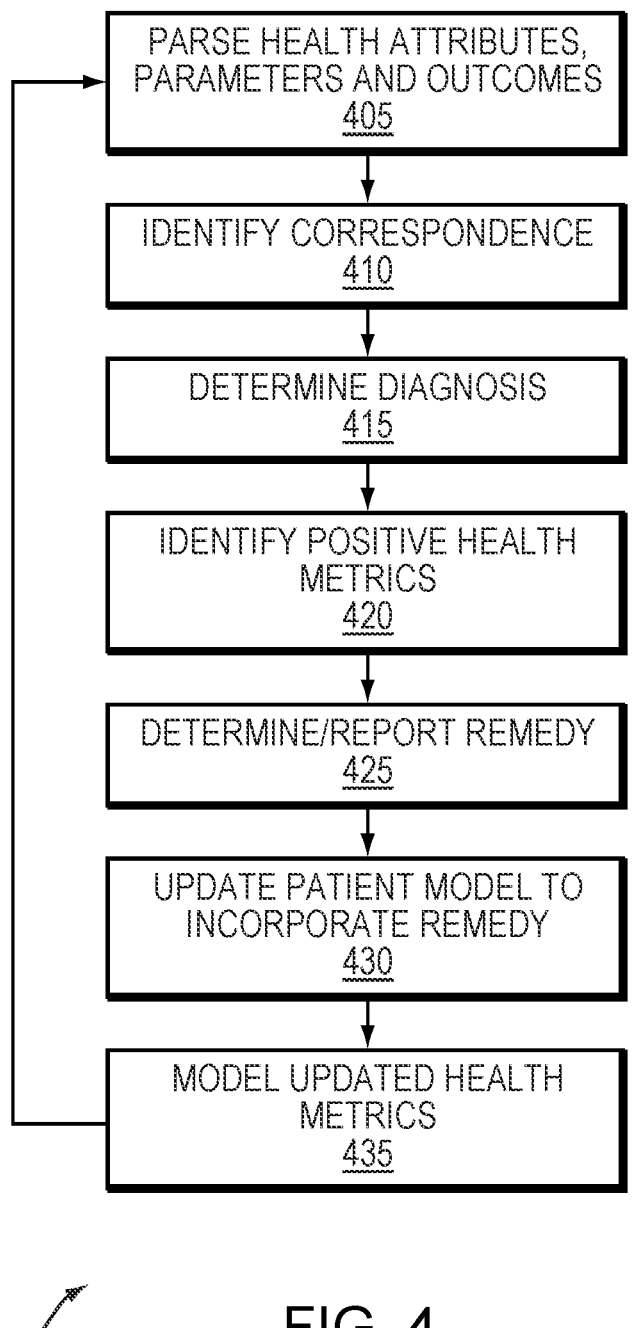
FIG. 4 is a flow diagram of a process of determining a diagnosis and remedy in one embodiment.

FIG. 4 is a flow diagram of a process 400 of determining a diagnosis and remedy in one embodiment. The process 400 may be operated in conjunction with the process 200 described above to further investigate the causes of negative outcomes, such as a decline in health metrics, altered health attributes, or an increased risk of an adverse outcome such as a diseased state. The process 400 may also identify effective remedies/interventions by identifying a causal relation between those remedies/interventions and an improvement to the outcome of the patient model under the modeled scenarios.

As described above, the operating the patient model through plural sets of parameters may yield a set of results, including health metrics, positive and negative outcomes, risks of adverse outcomes, and, potentially, changes to the health attributes of the patient model in subsequent scenarios. Those results may be used to generate a map 300 as shown in FIG. 3, which relates an initial patient state, subsequent states (by occurrence probability of a range of parameters), outcomes, and risks of adverse outcomes. Utilizing the map 300 or another data format, those results may be parsed (405) to identify correspondence between a subset of the health attributes, the plural resistance metric results, and the risk (410). This action may implement some or all of the process 900 described below with reference to FIG. 9. Based on this correspondence, a patient diagnosis can be determined, wherein the patient diagnosis may indicate the subset of health attributes that exceed a threshold correspondence with the risk (415).

Following diagnosis or as a separate process, one or more remedies can be determined. The remedies may correspond to one or more modifications to the patient model (e.g., health attributes) that have a causal relation to one or more positive changes to the patient model, such as changes that reduce or avoid a risk of an adverse outcome (e.g., a diseased state), or a positive change in the patient model's health metrics or health attributes in subsequent modeling. The process of identifying such remedies may implement features of the process 900 described below, except that the targets to be identified are health attributes and/or sets of parameters (e.g., positive interventions) that are responsible for a positive change in the patient model and/or health metrics (420). For example, a modeled scenario under a given set of parameters (e.g., an intervention) may result in positive health metrics for the patient model. Through multiple simulations and analysis, one or more parameters of the set of parameters may be identified as having a causal relation with the positive health metrics. Accordingly, a remedy can be determined as a change to the patient model in accordance with the one or more parameters, and that remedy may then be reported to a user (e.g., the patient or a health care professional) (425). In a further example, a subset of the health metrics that are negatively correlated with an adverse outcome (e.g., diseased state) is identified, and a remedy can be identified as one or more of the respective variables (e.g., of a set of parameters) that are associated with the subset of health metrics. In a still further example, determining the remedy may include 1) generating an additional set of parameters, the additional set of parameters indicating a health intervention, the health intervention including at least one of a medication, a therapy, and a diet; 2) modeling the health metrics of the patient model under the additional set of parameters to generate a resistance metric result; and 3) identifying the remedy based on the health metrics associated with the health intervention.

Optionally, the remedy may be incorporated into a reference table such as the table 500 described below with reference to FIG. 5. The patient may then be treated in accordance with the remedy, by directing the patient via a report (e.g., prescribed lifestyle changes or medication), or supervision or treatment by a health care professional. Optionally, the patient model may be updated to incorporate the remedy, by either updating the health attributes or configuring additional sets of parameters in accordance with the remedy (430). The patient model may then be simulated under the same or the additional sets of parameters to determine updated health metrics, thereby testing and/or validating the efficacy of the remedy (435).

Figure 5:
FIG. 5 is a diagram illustrating a lookup table cross-referencing patient states, risks, and corresponding remedies in one embodiment.

FIG. 5 is a diagram illustrating a lookup table 500 cross-referencing patient model states 510, risks 520, and corresponding remedies 530 in one embodiment. The table 500 may be generated based on the information resulting from the process 200 of identifying risks as described above with reference to FIG. 2. In particular, the patient model states 510 may be populated from a number of different iterations of the patient model, each of which may have been modeled under a range of permutated parameters. Likewise, the risk metrics 520 indicate, for each of the patient model states 510, the risks associated with the given state. The remedies 530 may be populated by actions and/or modifications to the patient model and/or external resources that are effective in preventing or avoiding adverse outcomes associated with a given risk. Such remedies 530 may be determined by the methods described herein. For example, the patient model may be modeled under parameters that include a prospective remedy, and, if the prospective remedy is determined to mitigate or avoid a predicted adverse outcome, then the prospective remedy may be included in the table 500 as a solution to a corresponding risk.

The lookup table 500 may be accessed using information on a given state of the information patient model. For example, for diagnostic applications, the state of the patient model may be analyzed and then compared to entries in the lookup table to determine the risk inherent in the patient model. The remedies 530, including remedies and/or suggested actions (e.g., modifications to the patient model) to avoid the risk(s), can also be reported, such that they may be implemented by the patient model itself.

Figure 6:
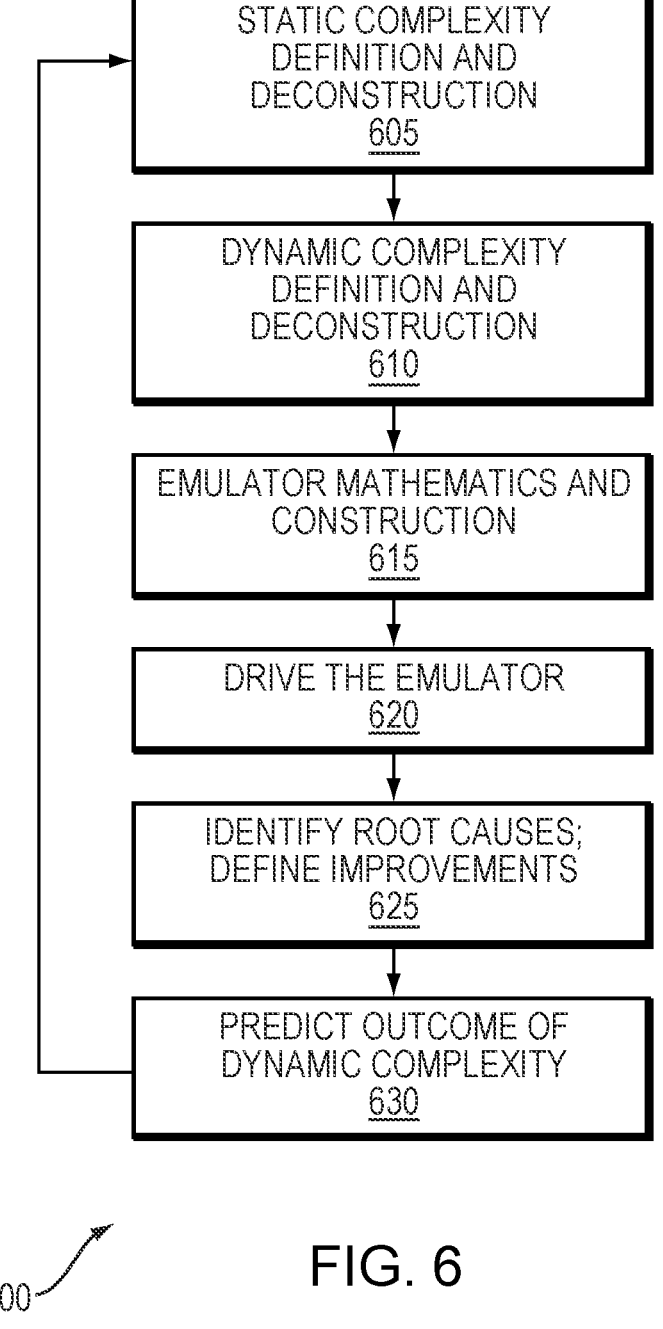
FIG. 6 is a flow diagram illustrating a process of deconstruction, emulation and analysis of a patient's health accounting for dynamic complexity.

FIG. 6 is a flow diagram illustrating a process of deconstruction, emulation and analysis of a patient's health accounting for dynamic complexity. The process includes stages that are described above, in particular with reference to FIGS. 1-5, where a subject patient model or environment is defined in terms of static complexity (i.e., the layering architecture and characteristics of each component in the patient model), the patient model is modeled and emulated under varying conditions, and the results of the emulation are analyzed and quantified, providing for solutions for improving the patient model. The process further includes defining the subject patient model in terms of dynamic complexity, and those definitions are incorporated into the stages of modeling, emulation and analysis.

The stages, as shown in FIG. 6, include: 1) Definition of the static complexity base and its deconstruction (605), 2) Definition of the dynamic complexity base and its deconstruction (610), 3) Construction of the emulator based upon defined Mathematics and Deconstruction (615), 4) Drive the emulator (620), 5) Identify root causes of unexpected behavior/adverse outcomes and define improvements (625), and 6) Predict the new behavior patterns with the dynamic complexity (as newly defined at 610) using the emulator (630). Each stage follows the previous stage such that the outputs of one stage become the inputs of the next stage. Each stage is described in further detail below.

Stage 1: Definition of the Static Complexity Base and its Deconstruction (605)

As an initial stage of preparing a mathematical model of a subject patient model and environment, information is collected regarding each of the components of the subject patient model, as well as the operational connections between those components. The information to be collected is sufficient for drawing an accurate mathematical model as described above with reference to FIGS. 1-5, and an example process of such information collection can be found in U.S. Pat. No. 6,311,144 (herein incorporated by reference). Inputs of this stage (605) include information regarding the patient (e.g., health attributes) and construct of the environment and patient model that are its static definition, including functional definitions (how each component of the patient model operates and interacts with other components) and physical definitions (layered architecture). The output of this stage (605) is a definition of the static complexity base of the subject environment or patient model.

In order to achieve an accurate static deconstruction of the subject patient model, the following actions may be taken:

1. Discover and identify the units or parts that make-up the environment or patient model. The granularity of this identification will vary with degree of precision that is needed to make the predictions at a later stage.
2. Discover and identify how these units are interconnected.
3. Discover and identify what flows along these connections.

Stage 2: Definition of the Dynamic Complexity Base and its Deconstruction (610)

In order to characterize a model of the patient model beyond its static description, additional information about the subject patient model and its components is collected and incorporated into the model as a definition of the dynamic complexity of the patient model. Inputs of this stage include the static complexity definition produced in stage (605), as well as information regarding how the static complexity changes over time. This information can be obtained through analysis of historical data about the patient model, epidemiological data (e.g., data derived from a given population that relates health attributes and incidences of various changes exhibited by the population), historical simulation data, data about comparable patient models, the patient's health attributes, and/or other sources. The output of this stage (610) is a definition of the dynamic complexity base model of the subject environment or patient model. In order to achieve an accurate dynamic deconstruction of a patient model, the following actions may be taken:

1. Discover and identify how each part or unit might change within the static complexity definition, which in turn indicates dynamic complexity.
2. Discover and identify how the connections within the static complexity base model have changed.

Stage 3: Construction of an Emulator Based Upon Defined Mathematics Deconstruction (615)

Given the static and dynamic definitions of the subject patient model (605, 610), a mathematical model of the subject patient model is then constructed for emulation (615). The mathematical model may be constructed as described above with reference to FIGS. 1-5, and may follow approaches as described in U.S. Pat. No. 6,311,144 (incorporated herein by reference). Inputs of this stage include the dynamic complexity definition produced in stage (610), defined mathematical techniques for emulation of the model, and computer programming techniques for production of the model. Outputs of this stage (615) include the emulator that can be used to establish the dynamic complexity and the resulting behavior patterns of the defined environment or patient model.

The mathematics of the emulator may include the following definitions:

U.S. Pat. No. 7,389,211 establishes the basis for a mathematical predictive solution that analytically predict system performance (in general terms). According to one embodiment such solution can be conceptually expressed in the form:

$$X = X_0 + \sum_M^{(d)} X_M + \sum_N^{(s)} X_N \tag{1}$$

Where $X_0$ is the initial value of a metric domain (e.g. complexity impact on performance, cost, capacity etc.)
$X_N$ is calculated direct impact due to N causes of static complexity (number of connections, number of interfaces, number of links, number of sites, distances, etc.)
$X_M$ is calculated direct impact due to M causes of dynamic complexity (interaction that impact components effectiveness, feedback that require higher throughput, interferences that impact liquidity, pandemic that impact health, aging that impact longevity etc.)

Convolution theorem allows a solution of a combined mathematical expression of two function-domains:

$$X = \frac{\delta X}{\delta \sigma} \text{ and } \sigma' = \frac{d\sigma}{dt}$$

with the combined solution using Laplace Transform $\mathcal{L}$:

Complexity Function $h(\sigma) = \mathcal{L}(h) = \int X(\tau) \cdot \sigma(t-\tau) d\tau \tag{2}$ Let us denote the vector $\sigma = \sigma(k)$ that represent the set of metrics that define a domain
The system of equations that represents the variations is:

$$\frac{d\sigma}{dt} = X^{(d)}\left(\sigma^{(d)}\right) + X^{(s)}\left(\sigma^{(s)}\right) \tag{3}$$

From (1) and (2) the impact of complexity on the domain metrics and using Laplace transform, is:

$$\frac{d\sigma}{dt} = \sum_k^{(d)} \frac{dX_d}{d\sigma_k}\left(\sigma'^{(d)}, \sigma^{n(d)}\right) + \sum_k^{(s)} \frac{dX_s}{d\sigma_k}\left(\sigma'^{(s)}, \sigma^{n(s)}\right) \tag{4}$$

d and s denote the 2 types of complexities and, $$\frac{dX_d}{d\sigma_k} \text{ and } \frac{dX_s}{d\sigma_k}$$

are computed by the method proposed in NA(3)
where $(\sigma'^{(d)}, \sigma^{n(d)})$ and $((\sigma'^{(s)}, \sigma^{n(s)})$ are representing a through different coordinates
and $\sigma^{i,s \text{ or } d}$ represent the complexity (i order) derivative, expressed in exponential form $$\sigma'^{(i)} = \sum_k^{(i)} \sum_n^{(i)} C_{njk} \exp^{zt} \tag{5}$$

where z is a complex variable that represent the two complexities
$z = \sigma^{(s)} + i\sigma^{(d)}$ where $i = \sqrt{-1}, \sigma^{(s)})$ and $\sigma^{(d)})$ the static and dynamic complexity respectively The set of equations 3, 4 and 5 allow the computation of all domain metrics as a function of varying the two portions of complexity representation.

We propose an aggregative concept, let us call it Complexial that represents the aggregated impact produced in each domain $X_0$ of the vector $X_0$ where $X_0(1)$ is performance, $X_0(2)$ denotes cost, $X_0(3)$ means quality of service and $X_0(4)$ represents availability etc.

From the above:

complexial=$\xi$=$\Pi_n(X_0(n)+X'(n)+X''(n)+\dots)$ where X are the complexity contribution of higher order perturbations (direct and indirect) of domain metrics n.

Stage 4 Drive the Emulator (620)

Once the mathematical model of the subject patient model or environment has been defined, the model is then emulated. The mathematical model may be constructed as described above, and may implement approaches as described in U.S. Pat. No. 6,311,144 (herein incorporated by reference). Inputs of this stage (620) include the mathematical model (emulator) from the previous stage (615), as well as one or more sets of operational scenarios that will be the actions that drive the emulation of the subject environment or patient model. Outputs of this stage (620) include a set of reactions of the emulated patient model that shows its behavior under a set of varying scenarios and how its complexity changes, as well as conditions and points in time when the behavior of the environment or patient model becomes singular or encounters another adverse or unacceptable outcome.

The outputs of this stage (620) allow for discovery and identity of when the behavior of the emulated environment or patient model becomes 'unexpected' due to a sudden change. This may comprise running a number of starting positions and controlling the emulator to run for a number of different time lines under different initial conditions.

In short, to establish a "patient model limit" due to complexity, two results in particular are identified. First, the patient model limit due to static complexity (the "ceiling") is what may be deemed to be the predictable limit that we understand from simple extrapolations, statistical trending and actual experiences. The "ceiling" is what is normally understood as the operational limits of a patient model. Second, the patient model limit due to dynamic complexity (a singularity), which is unpredictable by conventional methods (e.g. statistical trending) is identified. A singularity may occur at any point in time, predictable and governable through the mathematical methods that emulate interactions, feedback and interferences provided in example embodiments.

Stage 5: Identify Root Causes of Unexpected Behavior/ Adverse Outcomes and Define Improvements (625)

Once the mathematical model has been emulated through one or more test scenarios as described above, the results of the emulation can be analyzed to identify the root causes of the various detected results, including adverse outcomes (e.g., a diseased state), and changes to the patient model (e.g., remedies) to avoid such adverse outcomes. Inputs at this stage (625) include the calculated results of emulation from the previous stage (620), as well as measurements and observations of the actual patient model to condition and verify the outputs of the previous stage (620). Outputs of this stage (625) include remedies, which are suggested changes to the patient model.

Operations at this stage (625) include various methods of analyzing the emulation results, including discovering changes to health metrics, discovering risks of adverse outcomes, and building and computing further scenarios for emulation. Further, the results of the previous stage (620) may be quantified and qualified in a number of ways, including assessing the result for each scenario; combining scenarios to determine interventions. A method of determining whether an adverse outcome has occurred is described below with reference to FIG. 8. Further, one method of diagnosing an emulated patient model to determine the cause of adverse effects is described below with reference to FIG. 9.

Stage 6 Predict the New Behavior Patterns with the New Dynamic Complexity Using the Emulator (630)

In response to recommended changes to the patient model provided in the previous stage (625), those changes are incorporated into a revised model of the patient model, and the revised model may be emulated to determine the specific benefits incurred by those changes. Inputs of this stage (630) include the outputs of the previous stage (625), as well as defined improvement scenarios. Such improvement scenarios may include changes to the patient model intended improve health attributes, lower the occurrence probability of adverse or higher-risk patient states, improve health metrics and/or lower the risk of one or more adverse outcomes, such as affliction with a disease. Such improvements may be suggested as a result of a process as described above with reference to FIGS. 6 and 8-12. In particular, the outputs of this stage (630), following emulation of the patient model incorporating the suggested revisions, may include an improvement plan specifying remedies or interventions, such as lifestyle changes or medications.

Operations at this stage (630) include use of the reference predictive emulator to compute the improvement scenarios and define the plan. Further, the emulator may driven to provide ongoing monitoring of complexity (e.g., over long-term simulated scenarios) to identify degradation due to increase in complexity, determining the impact of such degradation, define actions to address the degradation, and determine the frequency of complexity monitoring and analysis (e.g., continuous, daily, weekly).

Stage 7 Dynamic Complexity Under Control

As a result of the previous stages, once implemented to identify and take preventive action against adverse outcomes resulting from dynamic complexity within an emulated patient model, the dynamic complexity of the patient model can be deemed to be controlled and predictable within an acceptable tolerance. An adverse outcome may be identified based on a rate of change in health metrics or other characteristics, where one or more of those metrics exceed a threshold rate of change. A singularity may be an example of such an adverse outcome, as well as other rapid changes to the performance or characteristics of a patient model. Thus, the results, and particularly the proposed changes to the patient model, can be exported from the model as recommendations to modify and improve the real-world patient model corresponding to the model.

Inputs of this stage include the outputs, knowledge and experiences of all previous stages, a change management plan, and information on the identified problems and challenges underlying the patient model. The outputs and ongoing states of this stage include a proposal regarding reporting structure, destination, frequencies, and content; the operations of a control function to implement the plan; and ongoing maturity improvements.

Figure 7:
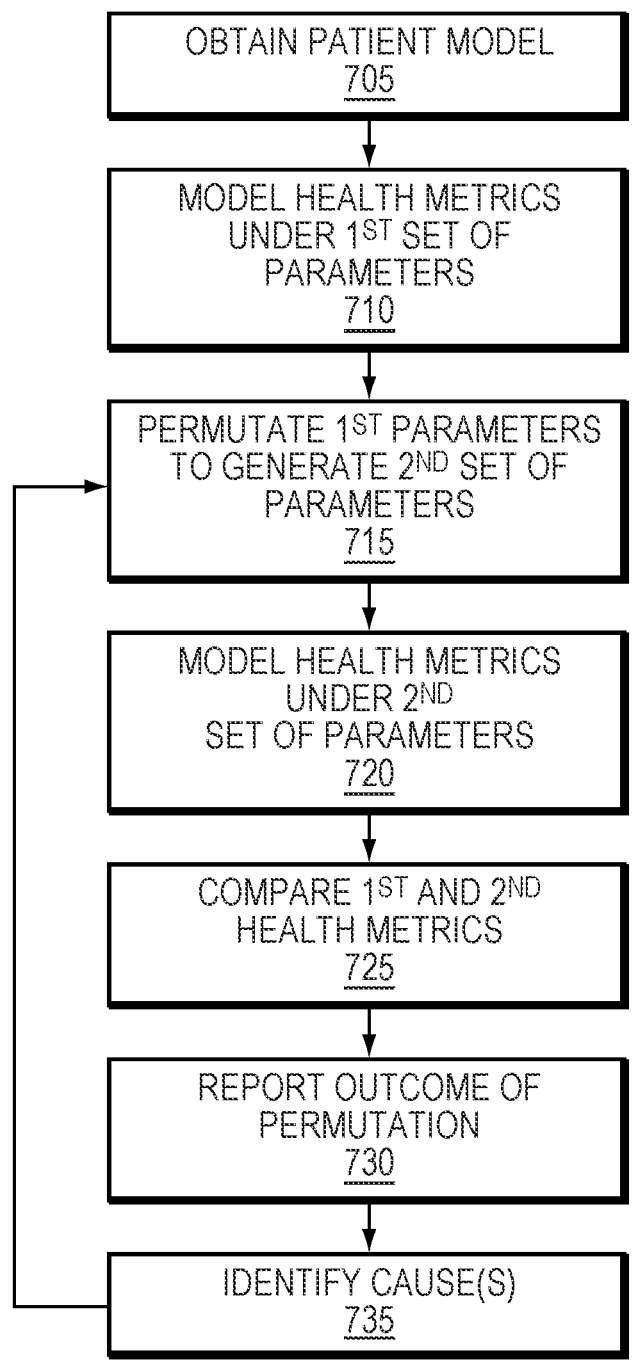
FIG. 7 is a flow diagram illustrating a process of emulating a patient's health under varying parameters accounting for dynamic complexity.

FIG. 7 is a flow diagram illustrating a process of emulating a patient's health under varying parameters accounting for dynamic complexity. This process may be incorporated into the process described above with reference to FIG. 6, and in particular expands upon the aforementioned steps of driving an emulator (620) and identifying root causes and defining improvements (625).

Initially, a mathematical model is obtained for emulation (705). The mathematical model may be constructed according to the process described above with reference to FIG. 6 (i.e., steps 605-615), and so may incorporate definitions of both static and dynamic complexity. In order to drive emulation of the model, a first set of parameters (operating conditions) are defined. The first set of parameters may be defined, as described above, to simulate the model as it operates through a given workload (or other set of inputs) over time. With the first set of parameters defined, the model is then simulated under the first set of parameters to generate a corresponding first set of health metrics (710). The first set of health metrics may be quantified in a manner as described above. The first set of health metrics may also include a dimension of time (referred to, for example, as time "T1"), indicating that the results correspond to the first set of input parameters upon simulation for a given length of (simulated) time.

Embodiments of the invention, as described above, provide for emulating a model patient model through a number of differing scenarios, where the results of such emulations can be analyzed to identify problems and potential solutions for the patient model. One method of this emulation is to permutate a set of input parameters, by altering one or more values, to generate one or more additional scenarios for emulation. Such selection of differing parameters is described herein with reference to FIGS. 2, 6 and 10. When selecting input parameters to detect an adverse effect resulting from a patient model's dynamic complexity, a number of variables can be selected for permutation. For example, input parameters can be permutated to simulate a change to the patient's health attributes, affliction of a disease, or an injury. Further, the length of time over which the model patient model is emulated may be varied. Such variation in time may be employed, with or without other permutations, to determine whether the input parameters result in an adverse outcome (e.g., a singularity) over a different (e.g., longer) length of time. With one or more variables selected, the first parameters are permutated to generate a second set of parameters (715), and the model is again simulated to generate a corresponding second set of health metrics (720).

Following obtaining the results of the first and second health metrics, those metrics may be compared (730) and reported to a user (730) to determine the effect of the different input parameters on the performance of the patient model. The health metrics can be analyzed further, as described below with reference to 9, to identify the cause or causes of the modeled results (735). The steps of permutation, simulation and analysis (715-735) may be repeated to determine performance and identify adverse outcomes under a range of scenarios corresponding to different input parameters.

Figure 8:
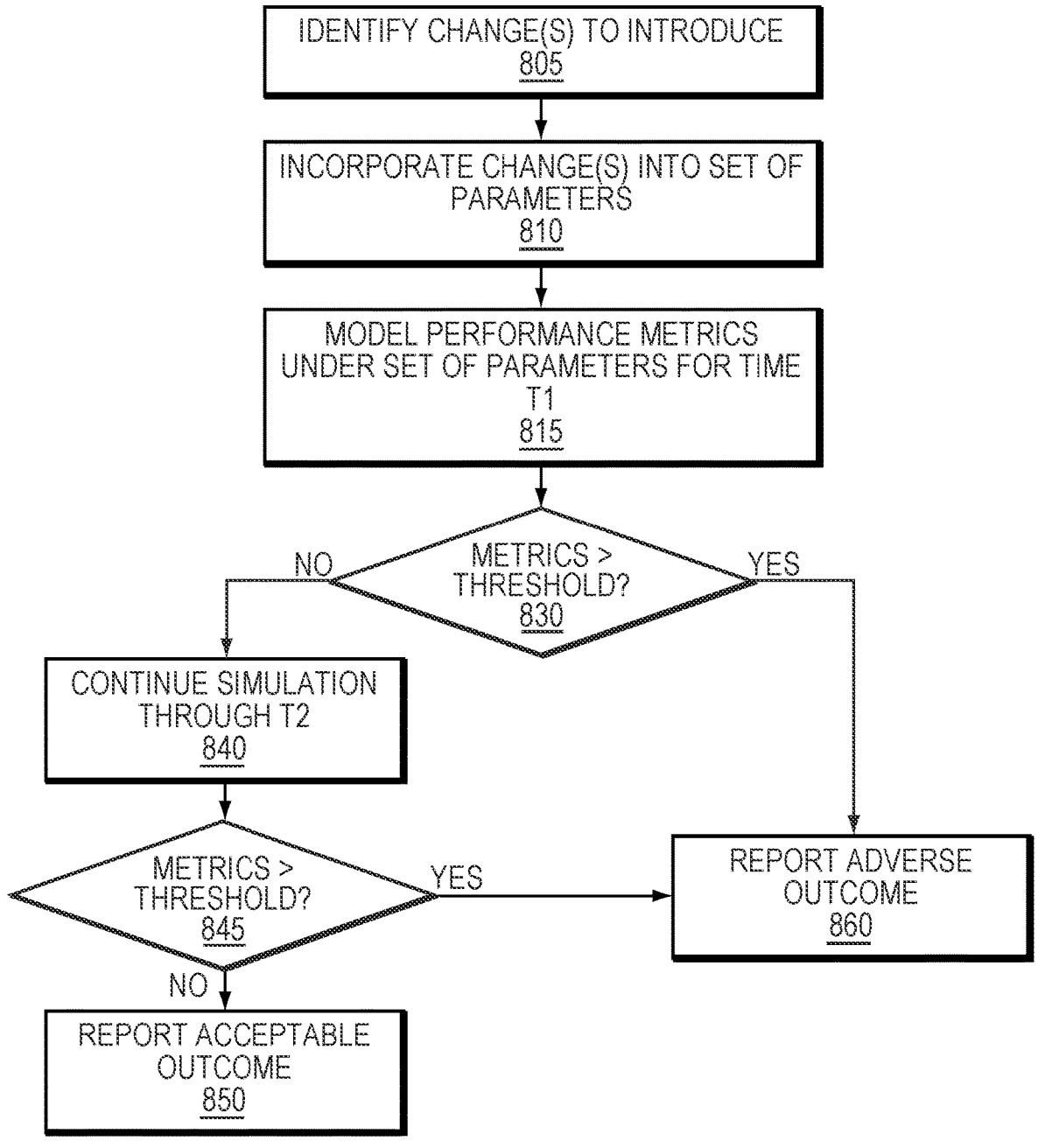
FIG. 8 is a flow diagram illustrating a process for determining whether an adverse outcome has occurred.

FIG. 8 is a flow diagram illustrating a process for determining whether an adverse outcome has occurred. The process may augment the process of emulating a model patient model under different parameters as described above with reference to FIG. 7, whereby health metrics are generated and compared against performance thresholds as the model patient model is emulated over varying lengths of time.

At an initial stage, changes to a set of input parameters are identified (805) and incorporated into a new set of parameters (810) for emulation. These steps may correspond to step 715 described above with reference to FIG. 7. Further, a time dimension T1 is selected as a simulated time over which to emulate the model patient model. The model patient model is then emulated under the new set of parameters over time T1 to obtain health metrics for time T1 (815). The resulting health metrics may then be quantified and compared against one or more thresholds (830). For example, health metrics may be quantified in terms of resistance to one or more diseases (resistance metrics), integrity of the patient's immune system to counteract the one or more diseases (HHD), and/or a risk of becoming afflicted with one or more diseases (risk index), and then plotted on a chart as shown for example in FIG. 5. The plotted metrics may then be compared against one or more thresholds corresponding to the relative change in the patient model's health metrics to determine whether the change in the patient model or health metrics has exceeded an acceptable threshold. If so, then an adverse outcome (e.g., diseased state) is reported (860). If not, then the simulation may be continued through to a further time T2 (840).

Due to the dynamic complexity of a patient model, an adverse outcome may only develop after an extended length of operating time, and may develop despite the failure to predict such an adverse outcome over a shorter length of simulated time. Thus, by extending the simulation through time T2, a model patient model can be tested more thoroughly to determine whether adverse outcomes result over greater lengths of time. If the resulting health metrics after time T2 exceed an acceptable threshold (845), then an adverse outcome is reported (860). Otherwise, an acceptable outcome can be reported (850), indicating that the model patient model exhibits positive health metrics under the given set of input parameters.

Figure 9:
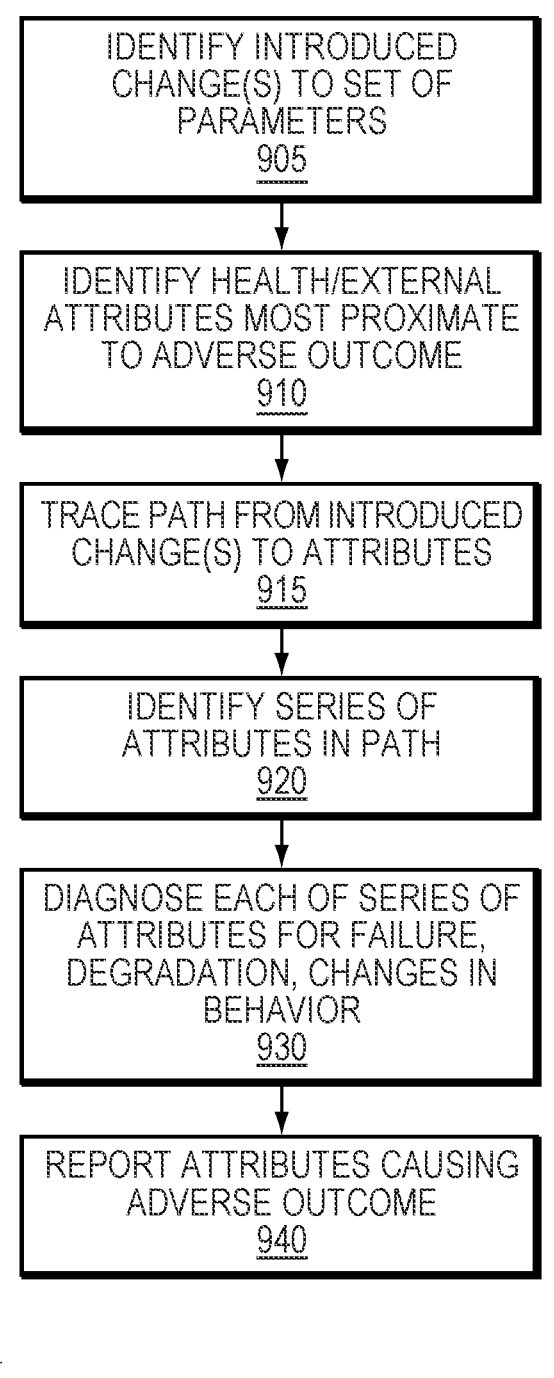
FIG. 9 is a flow diagram illustrating a process for diagnosing a patient following detection of an adverse outcome.

FIG. 9 is a flow diagram illustrating a process 900 for diagnosing a patient following detection of an adverse outcome. The process may be implemented to analyze the results obtained from the processes described above with reference to FIGS. 6-8. Given at least two different sets of health metrics generated by corresponding sets of input parameters, the differences between the input parameter sets are identified as the "changes" introduced into the model patient model (905). Those changes may be viewed as the initial (but not necessarily proximate) cause of an adverse outcome in the health metrics. For example, those changes may include simulating a change in the patient's health attributes, a positive intervention, an injury, or affliction of a disease.

Next, a component is identified that is most proximate to the adverse outcome (910). For example, a patient model may become afflicted with a first disease, which in turn lowers a health metric (e.g., resistance) below an acceptable threshold and raises the risk (via comorbidity) of becoming afflicted with a second disease. Once the initial and proximate causes are identified, a path may then be traced between them (915), where the path encompasses all operations and factors connecting the initial causes to the proximate causes. From this path, a series of nodes and dependencies can be identified in the path, each of which can be considered to have contributed to the causal chain leading to the adverse outcome (920). Each of these components can then be evaluated individually for failures, degradation, and other changes in the patient model that may have contributed to the adverse outcome (930). With reference to the example above, it may be determined that a lifestyle change by the patient, such as a change in diet or experience of a high-stress event, lowered the patient's resistance metric, thereby increasing susceptibility to the first disease, which in turn lowered the resistance metric further and increased the risk of susceptibility to the second disease. In addition, recognizing that other causally-linked factors (outside of this path) may also contribute to an adverse outcome, those other causes may be evaluated in the same manner. With the causes contributing to the adverse outcome identified, those components, as well as the specific problems inherent in each, may be reported for further analysis and remedies (940).

Further description of deconstruction of dynamic complexity and prediction of adverse outcomes, including example applications, is provided in U.S. Pub. No. 2012/0197686, the entirety of which is incorporated herein by reference.

Applying the modeling techniques described above, a range of patient models can be simulated as a multi-layer mathematical model having layers corresponding to health attributes, disease response rules, health metrics rules, and other aspects of the base model. In some embodiments, one or more such layers may be partially or wholly merged, or otherwise reconfigured to accommodate the particular patient model being modeled. For example, in a relatively simple patient model, where processes can be described easily with direct relation to the physical components, the process and implementation layers may be implemented in a common layer. Similarly, the implementation and physical layers may be implemented in a common layer.

Predictive Risk Assessment

The possibility of an adverse outcome, as described above, presents an apparent risk to the operation of a patient model, or even to the integrity of the patient model itself. An adverse outcome may be identified based on a rate of change in health metrics or other characteristics, where one or more of those metrics exceed a threshold rate of change. A singularity, as described above, may be an example of such an adverse outcome, as well as other rapid changes to the performance or characteristics of a patient model. By identifying outcomes including adverse outcomes and their causes, as described above, embodiments of the invention can enable a patient model to be reconfigured to avoid such adverse outcomes.

Further, embodiments of the invention can be applied, in a more comprehensive manner, to the identification and avoidance of a range of adverse outcomes. By modeling health metrics of a patient model under a range of parameters, the risk of an outcome including an adverse outcome can be ascertained as a probability. The risk can be qualified by a particular adverse outcome, as well as a predefined period of time. Several such risks can be reported simultaneously when warranted.

In an example embodiment of identifying and reporting one or more risks, a multi-layer mathematical model of a patient model bay be provided as described above. Health metrics of the multi-layer model may be modeled under plural sets of parameters, where the health metrics may include a resistance metric, a HHD metric, and/or a risk index. From these health metrics, one or more adverse outcomes may be identified based on a change or a rate of change in the health metrics exceeding at least one predetermined threshold. Given the identified adverse outcome(s), a map can be generated to relate the adverse outcome(s) to corresponding instances of the plural sets of parameters. Based on this map, one or more risks can be determined and reported, where the risk(s) define a probability of an outcome including the at least one adverse outcome. Example embodiments providing predictive risk assessment and management are described in further detail below.

FIG. 10 is a state diagram illustrating a process 1000 for patient risk management in one embodiment. The process

1000 may incorporate a process of modeling a patient model, determining risks, and deriving solutions to those risks as described above with reference to FIGS. 21-27. The process 1000 may be understood as a cycle that is repeated to improve the perception and management of risk within a patient model.

Prior to implementing embodiments for determining risk as described above, initial risk perception 2805 (phase one) may be incomplete. Accordingly, in phase two (risk modeling) 2810, information is collected as necessary to perform the deconstruction and causal analysis based on gathered information from experience and benchmarks of similar situations. From this data, the investigation and provocative scenarios that will reveal the risk and singularities may be built. Using the mathematical formulation and the deconstructed characteristics, dependencies and content behavior, a mathematical emulator that represents the patient model dynamics and the dynamic complexity is delivered. Using this emulator, scenarios can be deployed under different patterns of initial conditions and dynamic constraints to identify the risk and the conditions under which the risk will occur, as well as the possible mitigation strategies. The emulator can be continuously updated to replicate any changes that may happen over time with impacts on the problem definition, due to the evolution of dynamic complexity, environmental changes or content dynamics. Success is enhanced by the ability to keep the emulator representative, accurate, and able to capture all risks with sound projection of predictions.

After building the emulator in phase two 2810, in phase three 2815 (risk discovery), modified scenarios are run to identify possible risks. By modifying the parameters of each scenario within the emulator, one by one, by group or by domain, to represent possible changes, one may extrapolate each time the point at which the patient model will hit a singularity and use the corresponding information to diagnose the case. The emulator supports risk categorization based on the severity of impact, the class of mitigation, and many other characteristics that support decision making such as urgency, and the complexity and/or cost of implementation of mitigating actions.

For each of scenario, the ripple effect is particularly important to results interpretation. By using perturbation theory as the analytical vehicle to represent patient model dynamics involving direct and indirect effect on components, as well as trajectories representing sequence of components, the ripple effect is exerted on tightly or loosely coupled interactions.

Other scenarios may be created during this phase 2815 to explore viable and proactive remedial options that secure an acceptable risk mitigation strategy and allow the patient model to be fixed prior to realizing negative outcomes caused by an eventual risk. This last dimension may be considered crucial in risk management, which supposes that most of the risk is discovered during this phase—including risks generated by dynamic complexity.

Mitigation is the identification, assessment, and prioritization of risks as the effect of uncertainty on objectives followed by coordinated and economical application of resources to minimize, monitor, and control the impact of unfortunate events or to maximize the realization of opportunities. Risk management's objective is to assure uncertainty does not deviate the endeavor from the patient's health. Thus, in phase four 2820, the information derived in the previous phases is implemented to mitigate risk to the patient model. The risk is identified and diagnosed, and then remediation plans may be built ahead of time to eliminate, eventually reduce or at minimum counterbalance the impact of the risk. It is the application of the knowledge gained in the earlier phases that allows us to be ready with awareness of what may happen and plans of how to remediate the risk. Example embodiments may utilize the knowledge database to continuously monitor patient models to cover the risk of both the knowns as well as the unknowns (e.g., risks) that are caused by the evolutionary nature of dynamic complexity.

In phase five, risk monitoring 2825, the monitoring process is implemented. Using the database that contains all risk cases generated in phase three 2815 and enhanced with remedial plans in phase four 2820, the patient model may be put under surveillance using automation technologies. Similar in functionality to what is used for planes, cars, and nuclear plants, the auto piloting capabilities may observe the patient model in operations to identify eventual dynamic characteristics that may lead to a pre-identified risk situation. If a matching case is found, an alert will be generated and the pre-approved remedial actions will become active.

Each stored case may contain an identifier, a diagnosis, and one or more options for remediation. If the auto piloting patient model does not find a matching case, but has identified critical symptoms that may cause a risk, the monitoring controller sends back the characteristics to the predictive modeling phase two 2810. The corresponding scenario may be run to estimate the risk, diagnose the case, and propose remedial options, which may then be sent back to the database, enriching the knowledge base with the new case. Using this approach, the auto piloting, monitoring and control patient model may gradually become more intelligent and exhaustive, which, over time, may serve to considerably reduce the occurrence of risks of adverse outcomes.

Figure 11:
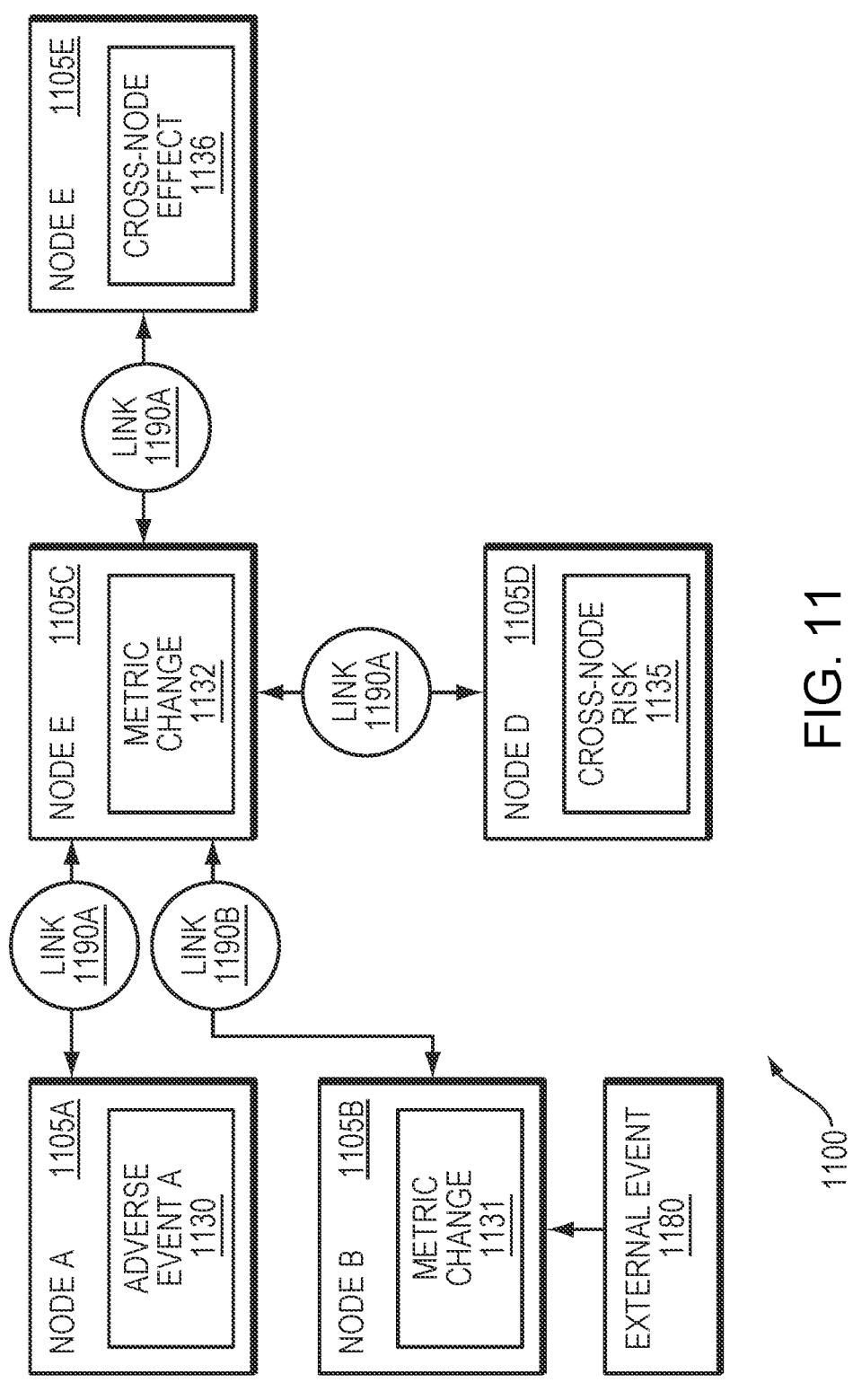
FIG. 11 is a diagram of a portion of a dependency graph of a patient model, illustrating propagation of a risk, in one embodiment.

FIG. 11 is a diagram of a portion of a dependency graph 1100 of a patient model, illustrating propagation of a risk, in one embodiment. The dependency graph 1100 may be implemented in the base model 110 and/or the dependency graph 130 described above with reference to FIG. 1, and may be generated from a process of generating a patient model as described above. The portion of the dependency graph 1100 shown here may be a subset of a larger dependency graph, wherein the elements of the dependency graph 1100 (nodes and links) are configured based on the causal relation between elements of the base model and health attributes that they represent. For example, each of the nodes 1105A-E may represent a respective health attribute (e.g., a genetic trait or a subset of a blood lipid profile) or a disease, wherein some or all of the nodes may have one or more properties (e.g., a variable or static value of the health attribute), and some or all of those properties may be affected by other nodes via links 1190A-D. The links 1190A-D may represent a causal (e.g., functional or mathematical) relation between the properties of one node and the properties of another. The health metrics described above may be represented by respective nodes, or may be calculated based on the properties of one or more other nodes. Further examples of dependency graphs as patient models are described below as exemplifications. For example, nodes 1105A and 1105B may represent different properties of a blood lipid profile (e.g., lipoprotein (A) and C reactive protein), and the values of each node 1105A-B are causally linked to node 1105C via links 1190A-B, wherein node 1105C represents a state of the patient's risk of arteriosclerosis. The node 1105C, in turn, may be causally linked to nodes 1105D, 1105E, which may represent conditions, properties or outcomes that have a causal relation to arteriosclerosis, such as cardiac arrest or arrhythmia.

In the example shown in FIG. 11, the dependency graph 1100 relates a cross-node effect 1135, occurring at node D 1105D, to the nodes, events and health metrics that substantially contribute to the cross-node effect 1135. Such elements may be selected for inclusion based on a number of factors, such as "but for" causality, proximate causality (e.g., contribution to the risk above a predetermined threshold), or occurrence of an event/health metrics that are correlated with occurrence of the cross-node effect above a predetermined threshold. Optionally, the dependency graph 1100 may include additional cross-node effects (e.g., cross-node effect 1136 at node E 1105E) that are partially or fully correlated to occurrence of the cross-node effect 1135.

Though emulation of the multi-node complex through permutations of parameters (as described above with reference to FIGS. 31-32), it may be determined that the cross-node effect 1135 is primarily caused by two influencers: 1) an adverse outcome 1130 occurring at node A 2205A, and 2) an external event 1180 exerting a change in health metrics 1131 at node B 1105B. It may be determined that both influencers are required to cause the cross-node effect 1135, or that one influencer (absent the other) is sufficient. The adverse outcome 1130 exhibits as a change in health metrics at node A 1105A, which propagates via link 1190A to node C 1105C. Likewise, the external event 1180 exhibits as a change in health metrics at node B 1105B, which propagates via link 1190B to node C 1105C. This propagation causes a change in health metrics 1132 at node C 1105C, which, in turn, propagates via link 1190C to node C 1105D, causing the cross-node effect 1135 to occur. The change in health metrics 1132 may also propagate via link 1190D to node E, causing the additional cross-node effect 1136. Thus, the dependency graph 1100 relates a cross-node effect to its causes as well as other effects of those causes. The dependency graph 1100 can be presented to a user to aid in preventing or mitigating the cross-node effect 1135, or may be utilized to identify modifications to the complex (e.g., remedial actions) to prevent or mitigate the cross-node effect 1135.

Example indicators or risk exhibited by a patient model may be referred to as a Dynamic Complexity Indicator (Dycom) and a Risk Index (RI). Dycom and RI may be implemented in the embodiments described above with reference to FIGS. 1-11, and are described in further detail with reference to US Published Application No. 2020/0175439, the entirety of which is incorporated herein by reference.

Risk Control Approach

The starting point of risk management, in example embodiments, is the analysis following the causal deconstruction of a patient model:

A) Discover the environment, its dynamics, the influencers that may provok a change, the key performance indicators and the goals in terms of health attributes, health metrics and/or risk of adverse outcomes.

B) Collect the detailed (static) complexity elements: process flows, structures, configurations, technologies and geography. Understand the dynamic complexity: dependencies, interactions, combinatorial, operating models.

C) Build the Mathematical Predictive dynamic complexity emulator through a top/down hierarchical constructs that will show: organizational, logic and physical views of the system (static complexity) and dependencies, feedback, combinatorial parameters patterns (dynamic complexity).

D) Computing the mathematical model will produce the key performance indicators derived from the computation of health metrics and risk of adverse outcomes.

E) After a proper validation of accuracy and precision, the emulator will be used to test scenarios and build the knowledge base:

a) By changing the initial conditions (e.g., health metrics via sets of parameters), dependencies and/or infrastructure, environment, and parameters, other adverse events and singularity points may appear and a chaos point may start forming.

b) By building and compute situational scenarios that may result from the feedback process.

c) By benchmarking solutions (remedies and interventions) and providing comparisons for decisions.

d) By providing the necessary knowledge for remedies and real-time intervention.

e) All along an important number of knowledge items will be derived and populating the knowledge base: come of these items may be known; but most interesting lot of these items may reveal unknown knowledge that have not been observed yet.

f) Prescribe remedies/interventions based upon an informed decision. By using the knowledge items collected during the previous phases, the patient model can be controlled to match an eventual situation with one of such knowledge items.

g) Therefore, the approach covers the situation now (curative) and the future (proactively): Now, by continuously monitoring and improving the patient model via remedies/interventions, and in the future by continuously creating new scenarios and identifying the limits, then eventually discover new risks of adverse outcomes and finding the way to bypass those risks.

Such an approach may provide health professionals a platform to control, plan and identify ideal outcomes for a patient. In short, both goals of reducing uncertainty, and proactively estimating and fixing problems. Long-term machine learning process will start by modest coverage of process proactive fixing to become over time an intelligent platform that will be able to deliver fast and comprehensive recommendations for right time fixing.

Figure 12:
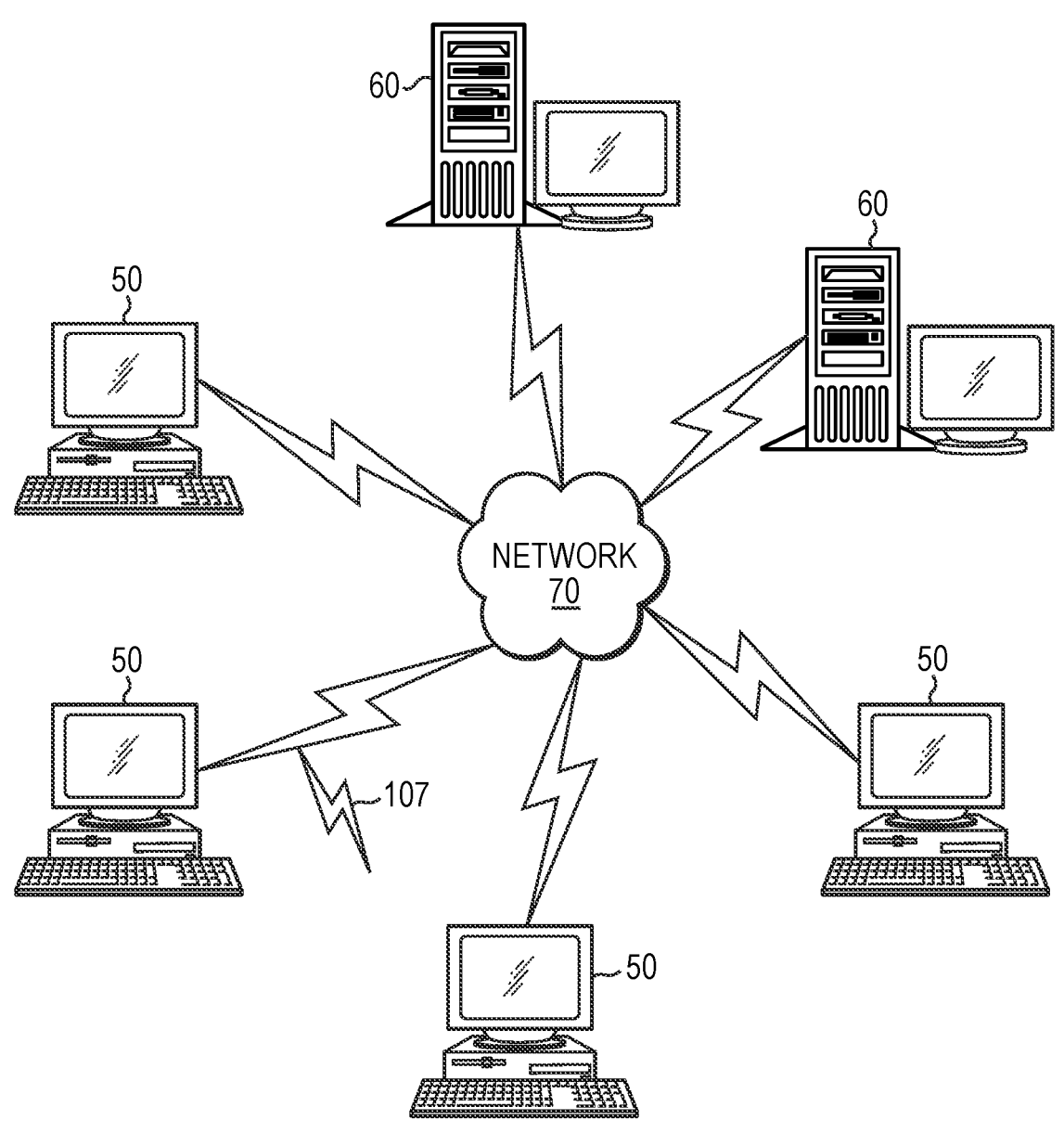
FIG. 12 illustrates a computer network or similar digital processing environment in which embodiments of the present invention may be implemented.

FIG. 12 illustrates a computer network or similar digital processing environment in which embodiments of the present invention may be implemented. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 13:
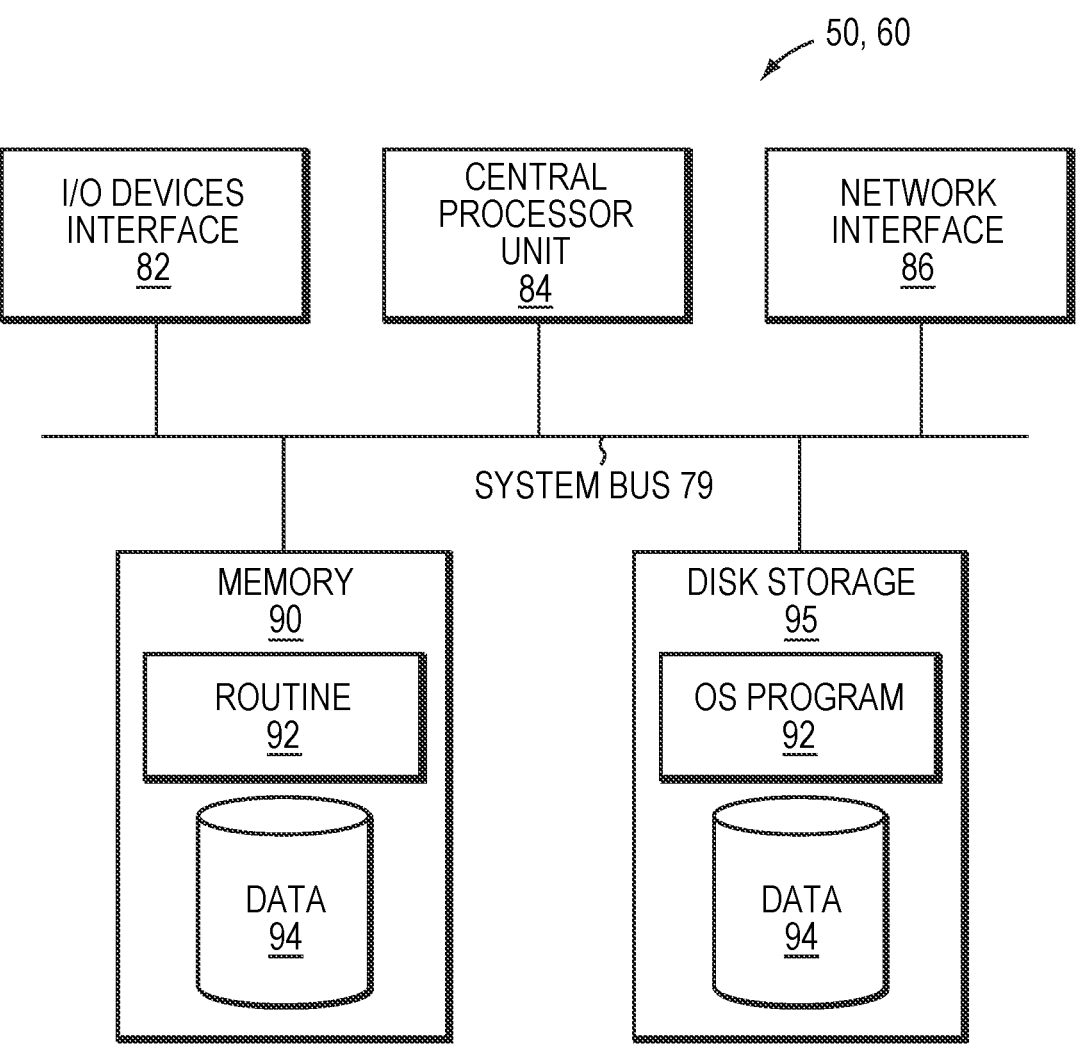
FIG. 13 is a diagram of an example internal structure of a computer (e.g., client processor/device or server computers) in the computer system of FIG. 12.

FIG. 13 is a diagram of an example internal structure of a computer (e.g., client processor/device 50 or server computers 60) in the computer system of FIG. 8. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network. Memory 90 provides volatile storage for computer software instructions 92 and data 94 used to implement an embodiment of the present invention (e.g., the processes and data structures described above with reference to FIGS. 1-11). Disk storage 95 provides non-volatile storage for computer software instructions 92 and data 94 used to implement an embodiment of the present invention. A central processor unit 84 is also attached to the system bus 79 and provides for the execution of computer instructions.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection.

Exemplification 1: Mechanistic Analysis of Cancer Nonlinear Dynamics and Causality Oncology research exposes cancer as a dynamic disease that results from complex interactions between multiple scales of genetic, environmental and constitutional characteristics that are unique to an individual. Currently, the full scope of determinants that cause numerous point mutations to accumulate and/or structural alterations to occur in the process of tumor progression are not fully understood. Shifting from a component to a system-level perspective can help add the context and understanding necessary to make sense of current oncology research.

In example embodiments described herein, a systems-based framework and perturbed graph analytics can be used to add the missing context of complex cancer processes and promote further understanding of how dynamic interactions between a large number of determinants, such as DNA, pathogens, autoimmune responses, metabolism, environment and aging influence the progression of cancer. The presented method demonstrates that a hierarchical, mechanistic modeling solution can be usefully applied to identify complex cause-and-effect relationships both horizontally and vertically across multiple scales and at any point in time. Further, an iterative process that creates a symbiotic relationship between physical and in silico research can deepen the understanding of cancer progression, identify promising new areas for scientific research and improve the certainty of predictive diagnosis and treatment outcomes for a specific patient.

Mounting evidence shows that a large number of determinants at multiple levels directly and indirectly influence the risk of developing cancer.

a) Genetic Causes: Genes can mutate over time and become cancerous due to a variety of causes, including diet and lifestyle choices as well as exposure to certain environmental factors. It has been observed that over 90% of cancers to have some type of genetic alteration. Some of these alterations are inherited, while others are sporadic meaning that they occur by chance or from environmental exposures over the course of many years. When genomic instability occurs, numerous point mutations can accumulate, and structural alterations can occur in the process of tumor progression. Researchers are investigating whether genomic variations could give rise to tumor antigens, which could be recognized by the immune system as non-self and elicit cellular immune responses. Further, scientists and clinicians are using and developing new tests to search for biomarkers to help identify cancer risks and appropriate treatment options based on an individual patient's genetic profile. However, it is important to note that not all cancers are due to a genetic disorder. For instance, of three ependymoma brain tumors, one subtype may lack tumor-driving mutations but has aberrant epigenetic modifications, while another shows neither gene mutations nor epigenetic aberrations.

b) Behavioral Causes: There are a number of behavioral factors that can lead to genetic mutations and the subsequent development of cancer including smoking (tobacco),ix tanning (excessive exposure to ultraviolet light), diet (red, processed meats), alcohol consumption, unsafe sex (leading to viral infection) xiii and inflammatory conditions, such as ulcerative colitis or obesity.

c) Environmental Causes: Exposure to certain carcinogens in the environment can damage DNA and trigger cancer. Examples include excessive sun exposure (ultraviolet light), chemicals like asbestos and benzene, hormonal or immune-suppressing drugs, radioactive materials like radon, and various sources of radiation (including excessive X-rays).

d) Viral and Bacterial Causes: A person's behavior and surroundings can expose them to bacteria and viruses known to cause cancer, such as Human papillomavirus (HPV), Hepatitis B (HBV) and hepatitis C (HCV) viruses, Epstein-Barr virus (EBV), Human T-lymphotropic virus, Kaposi's sarcoma-associated herpesvirus (KSHV), Merkel cell polyomavirus and *Helicobacter pylori.*

Cancer is a nonlinear, dynamic disease and there is no one single cause for cancer. Rather, it is the combined interaction of many factors that change over time and space that produce cancer and influence the prognosis of a cancer patient and/or the efficacy of various treatments. These factors include genetic, environmental or constitutional characteristics of the individual. Because the dynamics of cancer are coupled in complex, nonlinear ways to cell phenotype, molecular properties, and external phenomena, a small change anywhere in the hierarchy of cancer determinants can have a large (and often unexpected) effect on the health of a patient.

Further, cancer must be understood from an evolutionary perspective. Many complex and time sensitive processes are involved in the transformation of normal cells into malignant derivatives. Critical pathological and molecular carcinogenesis and somatic evolution events include the loss of proliferative control, failure to undergo programmed cell death (apoptosis), onset of angiogenesis, tissue remodeling, invasion of tumor cells into surrounding tissue and in final stages, metastatic dissemination of tumor cells to distant organs. These events are often defined as a linear process, because the dynamics are not fully understood. However, it has been argued that dynamic environmental and genetic factors contribute to cancer evolution through a distinctive sequence of events that influence the survival, proliferation and death of cancer cells. These events may be determined by Darwinian interactions between a cell's phenotype and critical properties of their local environment.

Where data driven and reductionist models are unable to integrate all the causal mechanisms of cancer, mechanistic models can be used to gain new insights into the dynamic complexity of tumor development and the molecular mechanisms that underlie the progressive transformation of normal cells into highly malignant derivatives. Adding context and understanding of how interactions between system components impact the evolution of cancer should lead to the development of more targeted prevention, diagnosis, and treatment strategies for specific populations as well as individual patients. The goals of the proposed systems-based approach are to (1) improve the domain knowledge and (2) make better use of the knowledge gained from reductionist methods.

Figure 14:
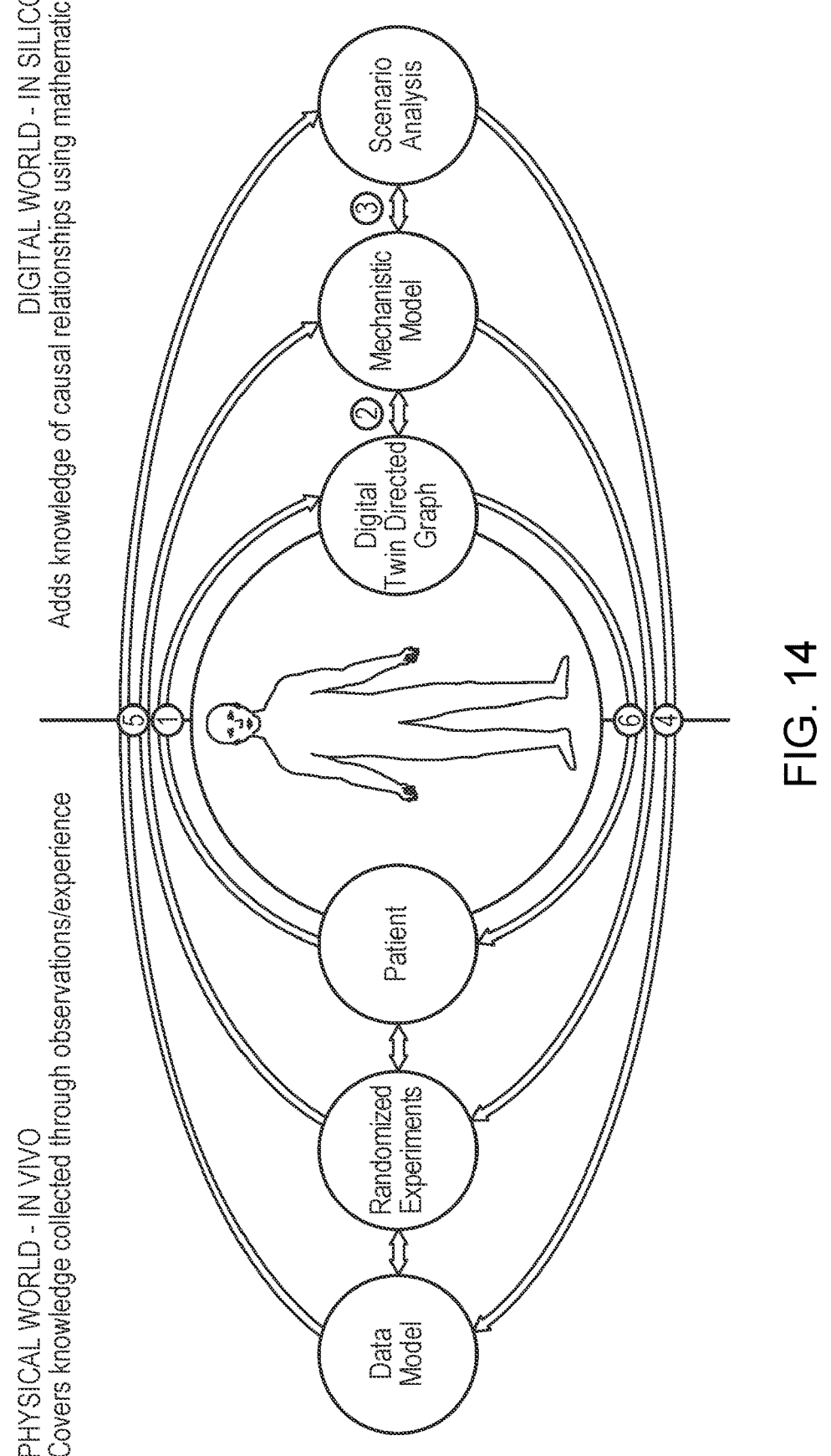
FIG. 14 is a diagram illustrating operations used to digitally transform the mechanisms of health into a mathematical model.

FIG. 14 is a diagram illustrating operations used to digitally transform the mechanisms of health into a mathematical model that covers the full hierarchy of graphs necessary to gain accuracy and certainty in behavior predictions. In turn these predictions can be used for the purpose of discovery as well as guide targeted physical experimentation. The outcome of each cycle supports an improvement process whereby the mechanistic model reveals the missing cognitive data, which can be vetted through in vivo experimentation and traditional data analysis. Once the algorithmic cognition is confirmed, machine learning can be used to more exhaustively cover individual patient scenarios in broader research and clinical applications.

Step 1: Deconstruct Epidemiology of Cancer

Key Tasks: Conduct preliminary interviews and perform audit of oncology research to develop a high-level understanding of known mechanistic cancer processes. Translate findings into a directed graph that captures the components and dependencies of cancer progression based on current patient experience/observations.

The goal of step 1 is to build a directed graph that maps the interdependencies, topology of structures, justification of choices, operational constraints, modes of operations, and data necessary to discover the hidden structures that form over time. In this first step, it is important to remember that the knowledge of cancer is incomplete, but also the incompleteness does not deter the construction of a useful model.

As an iterative process, a relatively simplistic directed graph built from limited data can provide a good starting point. This knowledge can be collected through interviews, research findings and data feeds. For this case, modelers conducted preliminary interviews with medical researchers to understand a few specific patient cases—including cancer diagnoses and treatment proceedings. Information was collected to populate three hierarchical graphs that would be encoded into software in 3 different views: Patient View, Disease View and Implementation View. The Patient View shows the top-down organization of health to disease trajectory, which could be any form of disease, but in this case was cancer.

The Disease View shows the disease trajectory and the hierarchy of disease characteristics. The characteristics include things like blood pressure, blood sugar, etc. This view connects to the lowest logical level which includes interdependencies like preexisting conditions, genetics and alteration, mutation and accidental determinants. The implementation view is composed of two levels: (1) the patient data, and (2) knowledge gained from experience and lab results.

The dynamic complexity of cancer supports the definition of an immune contexture, which represents the pre-existing immune parameters associated with patient survival. Further, the role of distinct immune cell types in modulating cancer progression is being recognized. Therefore, the goal was to build a model that was able to replicate the combination of multiple immune parameters, rather than individual ones, to verify if this would increase prognostic and/or predictive power of the model. Table 1 provides a broad overview of the immune parameters that were used to construct the directed graphs for the implementation view of the cancer disease model.

The list below provides a high-level example of the of cancer assumptions and mechanisms that were considered as important in this preliminary Step 1 graphing exercise:

a) Cells are integrated into an architectural and signaling framework which allows each cell to know which commands to execute at any given time. Success leads to homeostasis, while failures result in dysfunctions, including cancer.

b) Over a cell's lifetime, individual cells can experience multiple harmful genetic lesions or mutations. This mutation slowly spreads until eventually all cells have the same mutation.

c) If cancer was caused exclusively by the mutations, it would be expected that all cells would eventually become cancerous. Also, hereditary cancers only appear in one tissue type even though all cells contain the genetic mutation. Therefore, other factors, such as microenvironment conditions, must keep the development of cancer from occurring.

d) A wound or inflammation can disrupt the microenvironment and subsequently allow mutated cells to develop into cancer by removing or reducing signaling functionality within the microenvironment.

Further, a limited number of behavior factors (smoking, tanning and alcohol consumption) as well as environmental factors (chemical carcinogens and radioactive materials) were included to demonstrate the ability to capture external influences in the model.

Clearly the information gained during this first step is not exhaustive, but it is the beginning of an iterative process. After the completion of the 6-step methodology, a new cycle begins and supports a continuous enrichment of the model supported by expanded data and algorithmically derived knowledge. Any new research or change processes can be added to the base dynamics' definition as the research and related understanding of cancer evolves.

Step 2: Build the Mechanistic Model

Key Tasks: Turn the history of individual patient cases collected in Step 1 into a generic mechanistic model with validated diagnosis, risks and treatment details that represent patient health interdependencies at a known point in time. Conduct feedback interviews to fine tune and improve the representativeness of the generic model.

In step 2, the specific patient cases captured in the previous step are turned into a generic model that covers validated diagnoses, remediation and mitigation actions. At this stage, the graph represents the interdependencies of disease at a specific point in time.

Figure 15:
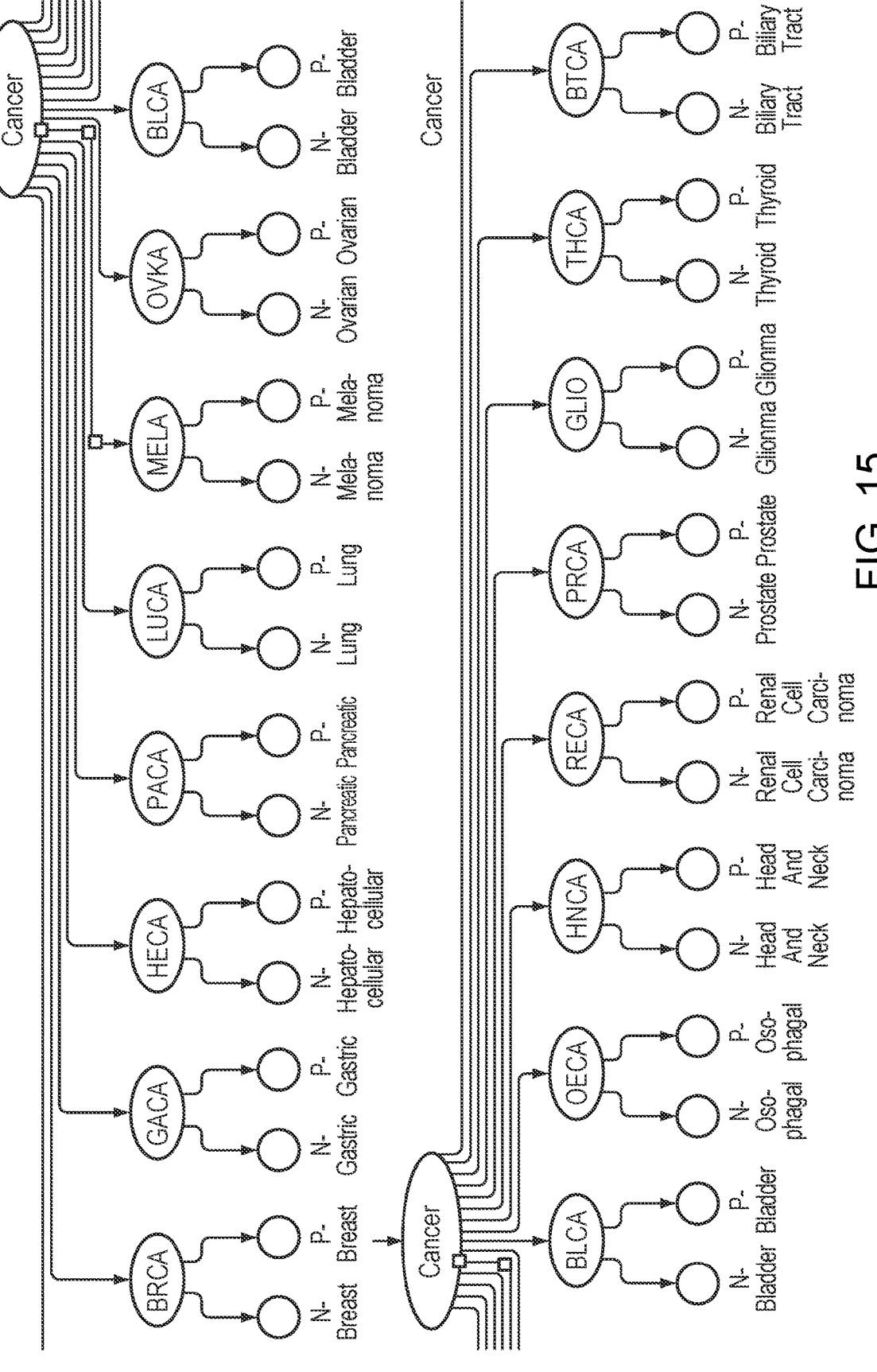
FIG. 15 illustrates a portion of a mechanistic model.
Figure 16:
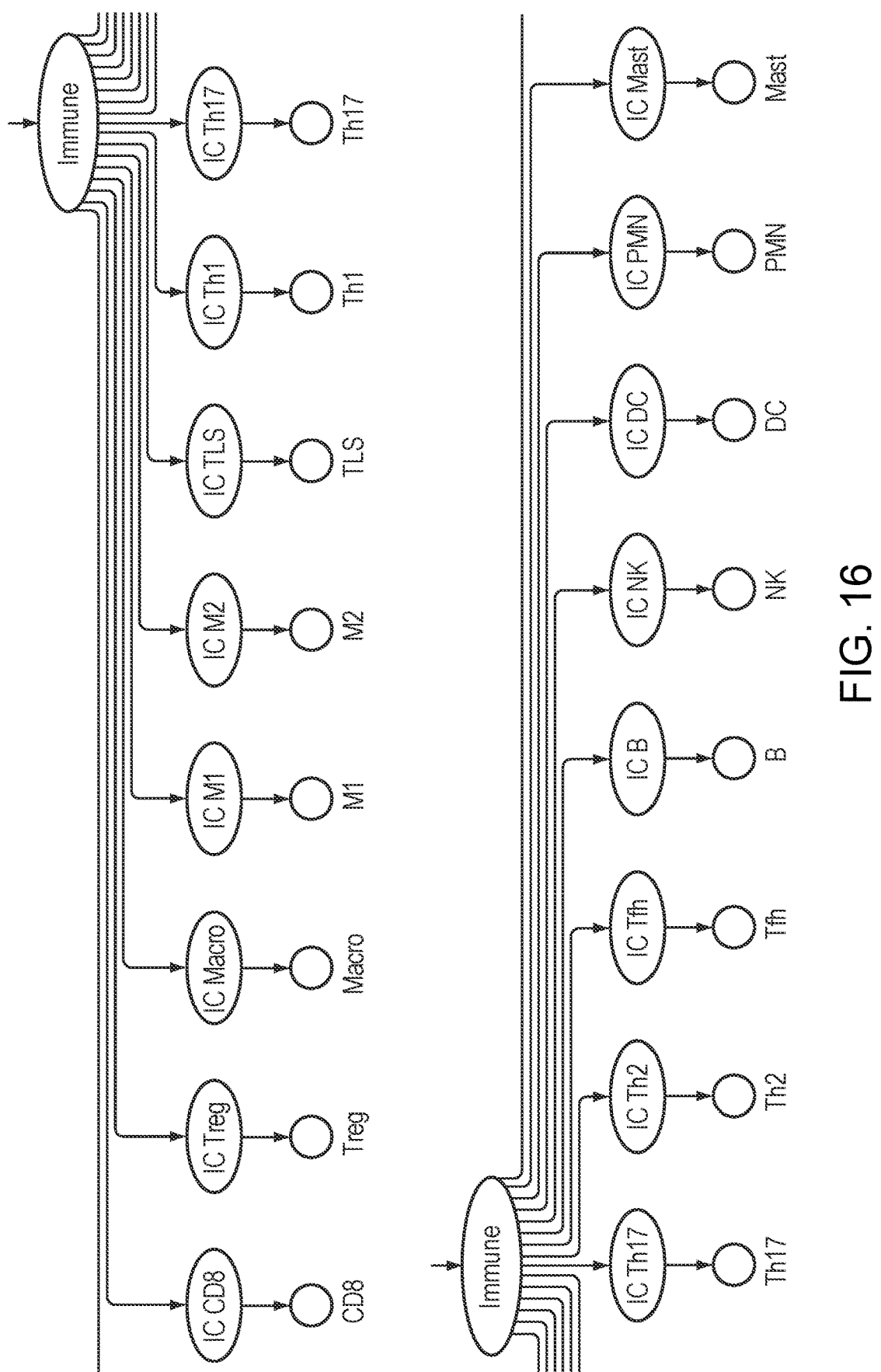
FIG. 16 is an example of parameter selection based on patient history.

FIG. 15 illustrates a portion of a mechanistic model, and shows the translation of the causal directed graph for all types of cancer into a software representation. This provides the hierarchical framework necessary to encode rules, system behaviors and hybrid decision making capabilities into software in subsequent steps. At this level of representation, each type of cancer is divided into precancerous versus cancerous scenarios to adequately capture the dynamics which define the evolution of normal cells into highly malignant and propagating derivatives. FIG. 16 illustrates the mapping of immune parameters that have been found to influence cancer patient outcomes.

Figure 17:
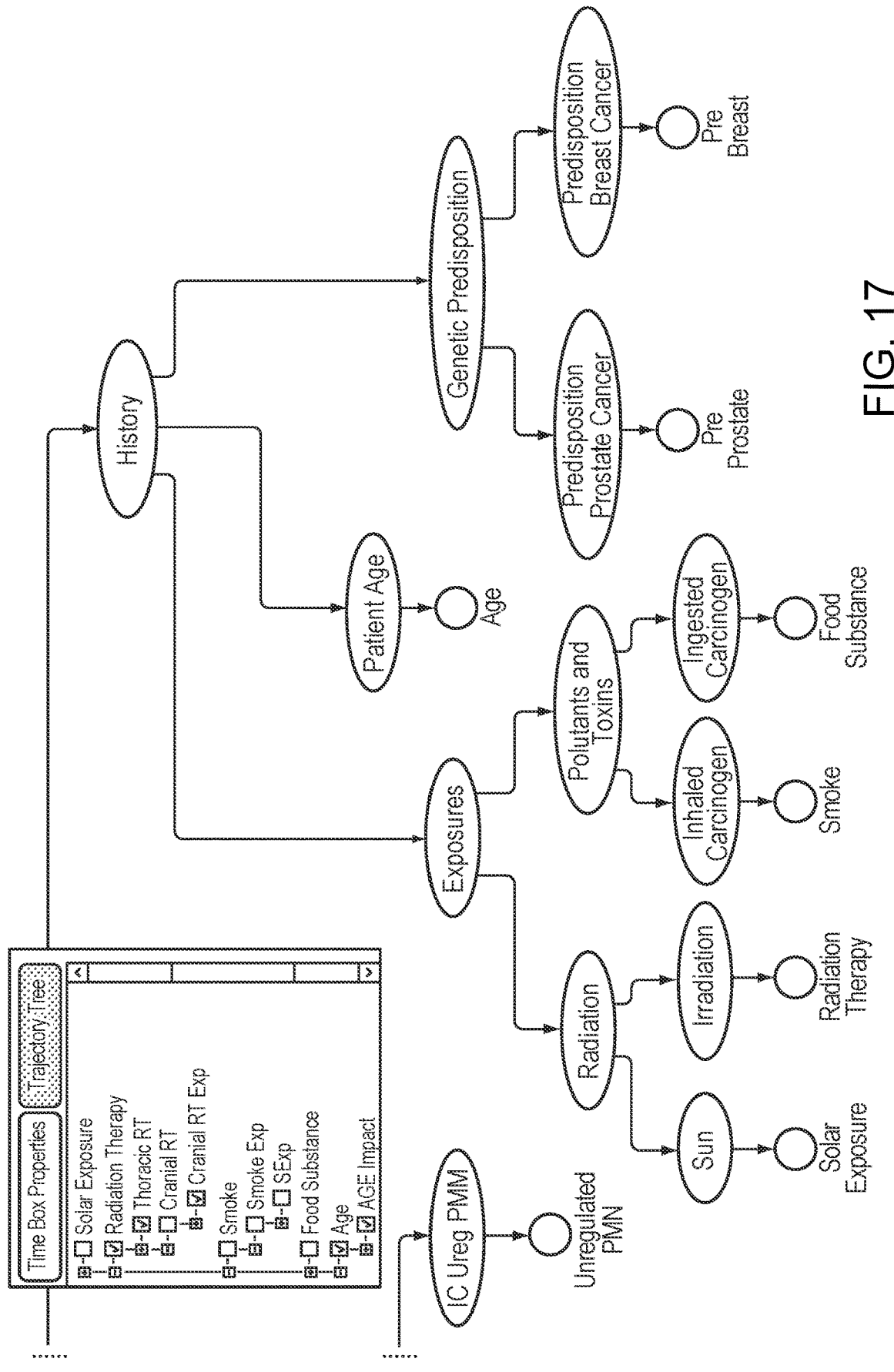
FIG. 17 is an example of parameter selection and computations based on immune cells and cancer types.
Figure 19:
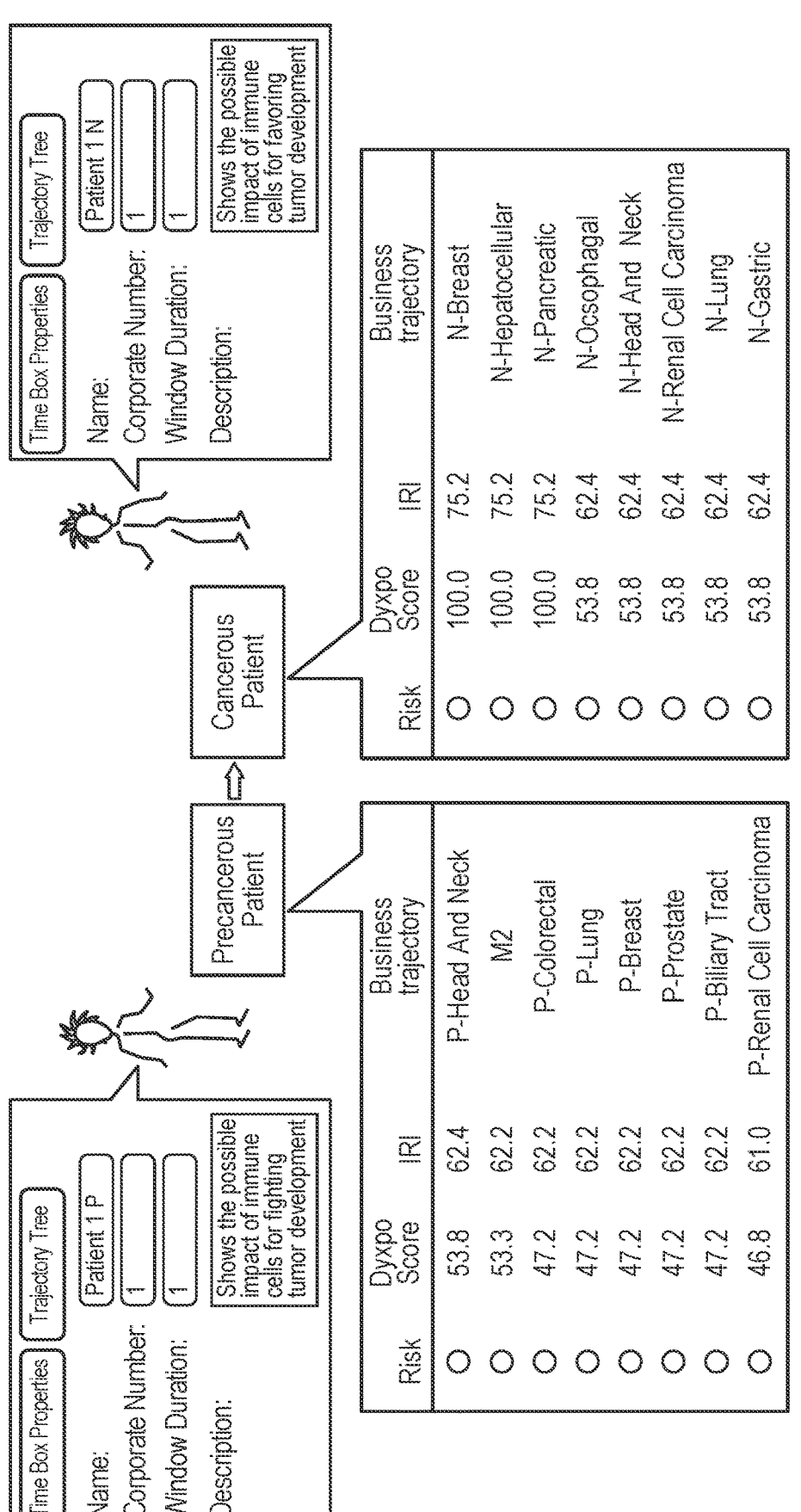
FIG. 19 illustrates a model of immune impact on a precancerous versus a cancerous patient.

In this step, the modeler also defined the parameters for sensitivity computation and predictive results. This enables the model to compute with the selection of variables that fit the environment. FIG. 17 is an example of parameter selection based on patient history and FIG. 18 as an example of parameter selection and computations based on immune cells and cancer types.

Step 3: Perform Scenario Analysis

Key Tasks: Submit scenarios, then interpret results to expose the unknown influences that may increase the risk of cancer.

Once the model is fully constructed, sensitivity analysis and what-if analysis are performed to see how different values of an independent variable impact a dependent variable under a given set of assumptions. The goal in this case is to expose the unknown influences that increase the risk of cancer in order to derive algorithmic knowledge that can be tested on a specified patient population through controlled experimentation.

As a starting point for the scenario analysis shown here, the modeler chose to investigate which cancer types are negatively impacted by the Mast immune cell for a hypothetical patient. To differentiate between Mast cells that are behaving as expected versus cells that are acting in an unregulated manner, the Mast parameter in the model was broken down into regulated and unregulated Mast. In FIG. 14, the left-hand side shows the metrics (as defined in the table below) of a precancerous patient versus a cancerous patient. This shows how the model can capture the effects of various immune system impacts that may involve regular or irregular immune responses caused by incidental effects and counterproductive mechanisms.

| Dyxpo Score | Measures the speed of exposure and is therefore, a critical metric to expose the propagation rate of disease |
| IRI | Indicates the degree of morbidity risk with values closer to 100% representing a critical risk |
| Dependencies | Degree of dependencies that indicates an increase in complexity that makes the case of morbidity more challenging to resolve |

Figure 20:
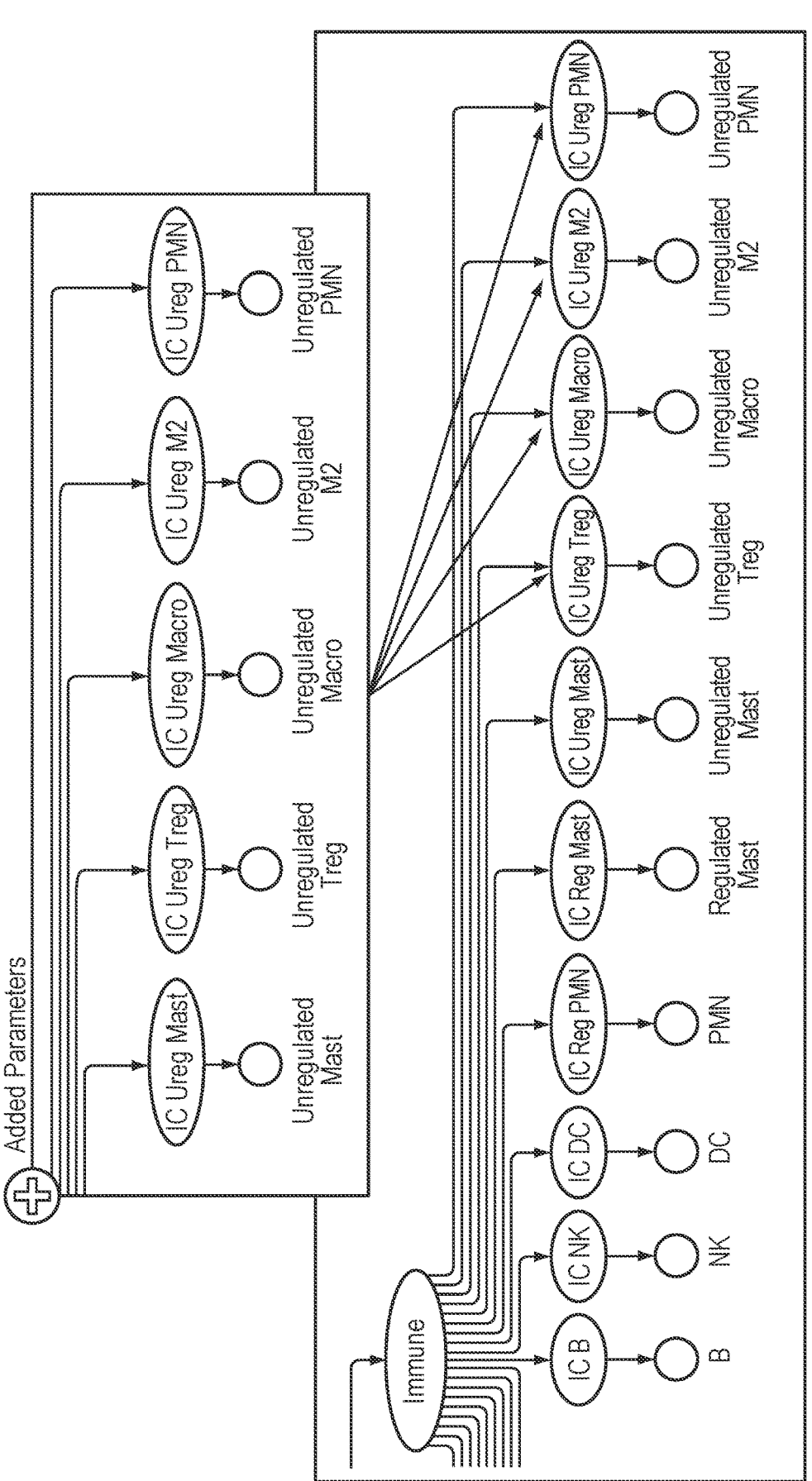
FIG. 20 illustrates a selection of model parameters added to an implementation view.

Referencing known cancer data, Gastric (GACA) and Bladder (BLCA) were identified as the only two cancers that might eventually be impacted by Mast for this hypothetical patient case based on the referenced research findings. The modeler then examined other immune parameters that are expected to negatively impact these two cancers. This added Treg, Macro, M2 and PMN as key immune cells for the chosen scenario analysis. Each were added in the model as unregulated parameters, which updated the patient view of the immune graph (FIG. 20).

After adding an unregulated (Ureg) component for each immune cell class in the appropriate partition, the emulator was computed to verify proper functioning of the model. With these changes, the focus was on Gastric and Bladder cancer, but the same type of customization is possible to study the causal relationships between any immune cells and various forms of cancer.

Two scenarios were created for hypothetical Patient '372873:' The first scenario '01-18-20 Patient 372873' represents an office visit, when the exam revealed no major health issues. In this scenario, 'regulated' is enabled for all parameters, but 'unregulated' is not enabled in the model. Once intensity values are set for each parameter, the emulator was computed. In this case all metrics associated with Bladder and Gastric cancer showed green indicators (see FIG. 21), meaning the risk of developing cancer is low as defined by the metrics outlined in the table above.

Figure 22:
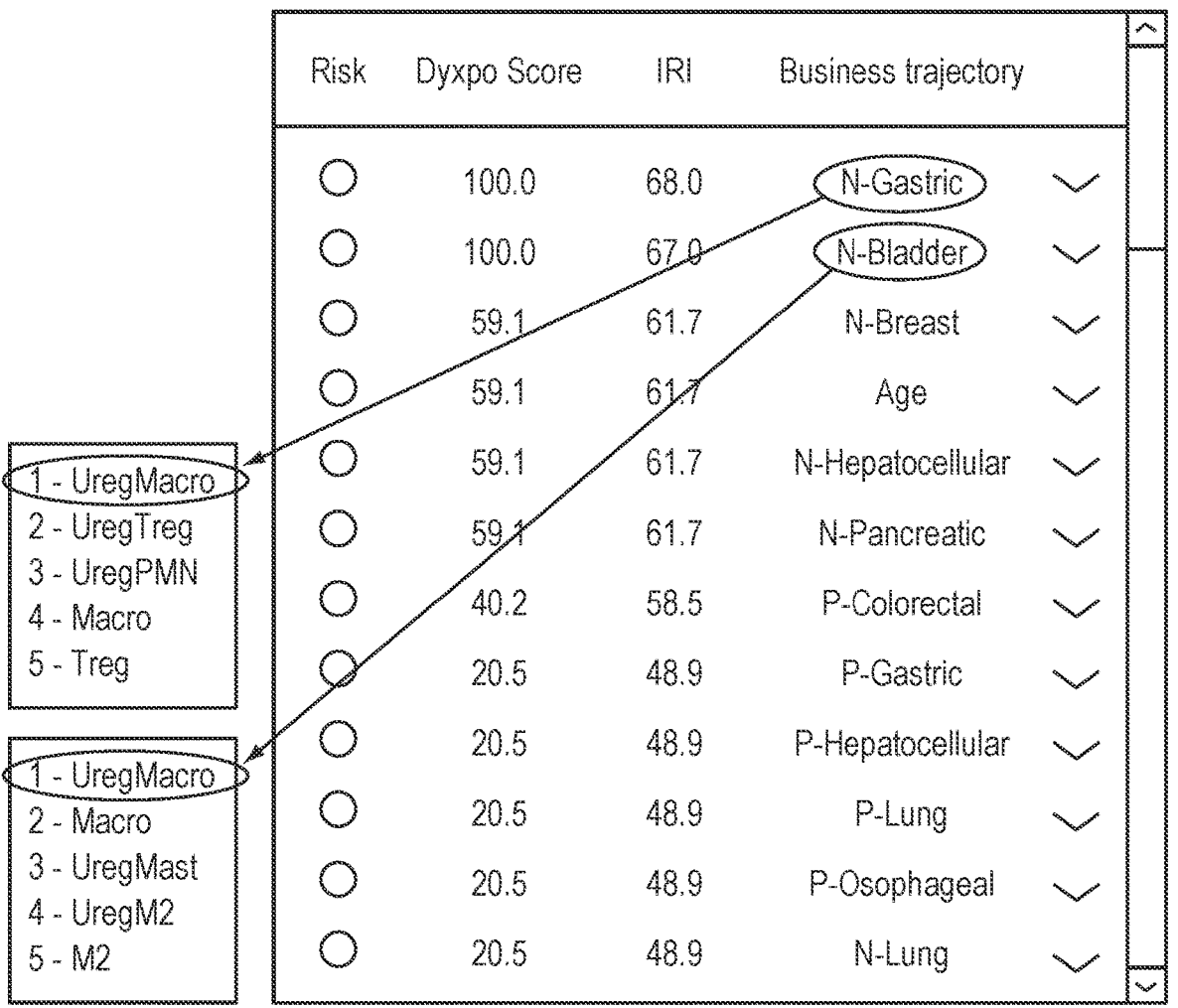
FIG. 22 illustrates a further example model computation result.

In the second scenario, '02-05-21 Patient 372873,' the hypothetical patient returns for a second visit and reports an injury, insect bite, internal mutation or other unspecified problem. To account for this change in health, intensity values are assigned to the Unregulated parameters and they have been checked in all cases with at least one or two sources of unregulated immune cells. Now when the scenario is computed, as shown in FIG. 22, the metrics expose a risk of developing cancer with the highest value for Gastric followed by Bladder cancer. The predicted risk of cancer is based on the specified immune cells in order of importance.

By analyzing predictive outcomes produced by this model versus known patient cases under various conditions, the modeler would be able to confirm the representativeness, acceptable accuracy and robust predictability of the model. If done correctly, the model should match known scenarios within 2-3% of reality. If this is not the case, the modeler adjusts the parameters until the desired model representativeness, accuracy and predictability is achieved.

This provides an opportunity to reverse engineer the cause of the discrepancy and ultimately leads to the discovery of new insights or the identification of unknowns by finding missing definitions or introducing new parameters at various levels of the graphs. Such efforts are particularly important once the modeling process has been established, since changes in health can occur at any time and necessitates the ability to quickly identify and apply a new diagnosis and therapeutic actions.

Step 4: Validate Findings

Key Tasks: Test on specified patient populations through controlled experimentation any new risk patterns that are algorithmically identified in Step 3 to confirm representativeness, acceptable accuracy and robust predictability of the models.

Key insights gained in Step 3 should guide the construction of in vivo experiments that are designed to confirm in silico findings and further enhance subject matter expertise.

Figure 23:
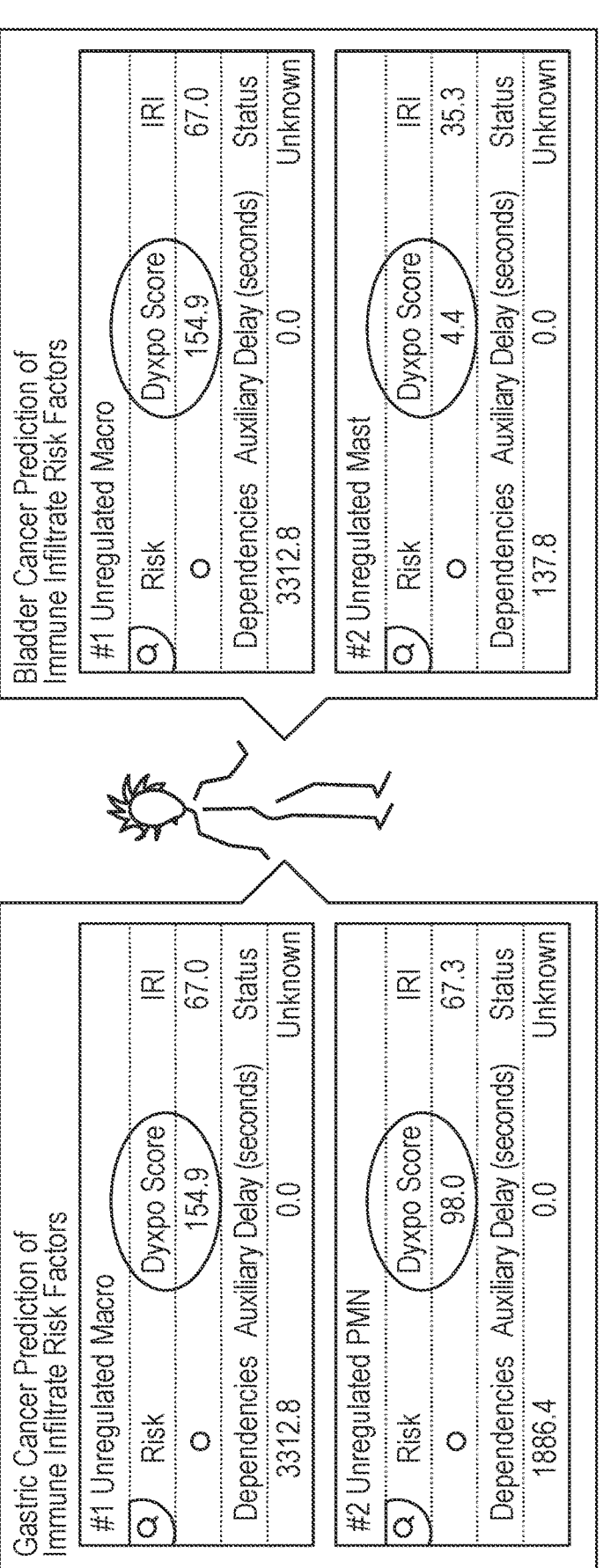
FIG. 23 illustrates a portion of an example risk report.

The risk for Gastric and Bladder cancers based on immune infiltrate determinants are lower in the precancerous patient scenario, but sensitivity and what if analysis shows that the risk can evolve at a point in time as the results of perturbations between regulated and unregulated immune cells. Further, Gastric and Bladder cancer scenarios share common immune infiltrate parameters. FIG. 23 shows UregMacro is the biggest contributor to risk for both Gastric and Bladder cancer.

If a review panel found the cognitive results to be significant, the predictive findings could be used to inform the design of randomized experiments or basket studies. The goal in this hyptothetical case would be to validate whether unregulated Macro cells would be a useful predictor of Gastric and Bladder cancers and further the understanding of the dynamic processes that lead to second cancers.

Step 5: Certify Models

Key Tasks: Create a library of certified dynamic patterns that encapsulate behaviors, dependencies and surrounding rules so that they can be used as artificial intelligence rules for machine learning and to perform predictive analysis.

After validating findings in step 4 through in vivo research studies, dynamic patterns that encapsulate behaviors, dependencies and surrounding rules for cancer behaviors would be stored in an Advanced Human Healthcare database so they could be used in artificial intelligence applications and to perform predictive analysis in clinical settings. Each model would include preventative guidelines and effective treatment protocols based on best practice guidelines cross vetted by a multidisciplinary team of clinicians, oncologists, biologists, treatment team, patient, etc.

Through continuous IAM cycles, the causes and effects of various cancer processes—both horizontally and vertically between system levels and at any point in time—may be rigorously validated to support the timely exposure of critical cancer risks applied through ML process that overtime will become more sophisticated and form the foundation for robust oncology intelligence.

Step 6: Use in Clinical Applications

Key Tasks: Create and enrich an Advanced Human Healthcare database that covers the known and predicted disease cases that may cause undesirable cancer outcomes. Included in each case is a diagnosis definition and remediation that allows for the rapid identification of a potential cancer risk with immediate analysis of root causes and proposed curative actions.

Using the situational data revealed from the iterative analysis methodology, the ultimate objective is to improve cancer detection and treatment outcomes for individual patients (FIG. 21). The goal of such efforts is to identify when a patient's cancer risks may be increasing—even before the patient begins to experience severe symptoms. This would be accomplished by combining the Advanced Human Healthcare database created in step 5 with AI and ML technologies to predictively analyze how changing patient parameters may result in a health risk or support more optimal health outcome. Such capabilities would enable the rapid identification of a potential problem with immediate analysis of root causes and proposed corrective actions. The active monitoring of IAM process outcomes would thereby provide a fully vetted platform to support individualized and proactive patient risk avoidance and suggest personalized treatment protocols when necessary.

In both clinical and research cases, these types of AI-enabled models have been able to compliment, increase accuracy and/or accelerate the work being conducted by humans. Diagnostic approaches in fields like dermatology, radiology, or pathology are examples of healthcare subsectors that are being transformed by AI.

Ultimately, the value of human digital twin, AI, deep learning and neural computation technologies in medicine will only be realized if they can quickly deliver to users something complementary and more complete than the current knowledge domain. To identify, anticipate and cure the causes of cancer, it will be necessary to continuously compute the human digital twin at any point. This requirement necessitates moving to a robotic cognitive approach that can be applied quasi instantaneously to identify and eventually heal any health imbalances that may lead to an undesirable outcome.

Foundationally, the nonlinearity of human health makes the pursuit of oncology research and precision medicine particularly problematic. Current oncology analysis methods are based on analogy, statistics and tumor centric approaches that ignore the complex topology of cancer. This introduces a high level of uncertainty, which translates into potential errors and insufficient control over cancer risks at the patient level.

The need to make sense of current oncology research which exposes complex genetic, environmental and lifestyle interactions justifies the shift from a component-level to system-level perspective. Where data driven and reductionist models are unable to integrate all the causal mechanisms of disease, mechanistic models can be used to gain new insights. Systems-based approaches allow for explicit recognition of feedback, interference, adaptation over time and nonlinearities. Adding context and understanding of how interactions between system components impact the evolution of cancer should lead to the development of more targeted prevention, diagnosis and treatment strategies for specific populations as well as individual patients.

Pairing the abilities of machine learning to process a large number of inputs and outputs with the deductive capability of mechanistic mathematical models and the nonlinear, multi-scale problem-solving capabilities of perturbation theory can provide the faculties needed to extrapolate predictions about behaviors that are not present in conventional data-based deductions and improve the certainty of these predictions through a scalable and repeatable modeling solution.

Perhaps most importantly, the mechanistic model provides the unifying framework necessary to expose how interdependencies within and between multiple scales can at any point in time amplify the risks or hide the solution. The advancement of this cognitive knowledge will accelerate the discovery process by supporting collaboration across disciplines and inform the design of highly targeted in vivo studies. Through continuous cycles of discovery, validation and certification of machine learning rules, AI applications will be able to translate cause into effect at the patient level and support the critical decisioning necessary to leverage precision medicine as an evolutionary force that improves the longevity and promotes a better quality of life for a patient based on his or her unique characteristics.

Exemplification 2: Reduce Diagnostic Uncertainties in Clinical Practice

To create representations of real-world events, like morbidity and therapeutic efficacy, computers are often used to create models using math, data and computer instructions. The model can then be used to predict what's happening with a patient—or what could happen—in complex situations like multimorbidity. Accurate predictive information provided through automated AI-enabled software would allow clinicians to make decisions without taking unacceptable risks in real life situations or waiting years to see how a patient's symptoms or morbidity evolves.

Scientists who build computer models start with important features of whatever events they hope to represent. Features that can change are called variables. To model multimorbidity for an individual patient in software, a computer modeler first needs to identify rules, which are expressed through mathematical equations, that control the features of multimorbidity and the dynamic relationships that lead to a certain patient outcome.

Therefore, the ultimate goal of building a model is to define the set of equations that can be solved to understand the behavior of the system being studied. Once the governing equations are known, it is then possible to create a computer program that will make accurate predictions of how the system will behave under various scenarios from given initial and boundary conditions measured at a few selected points. In essence if the correct mathematical formational can be identified, an AI-enabled computer program can use known information to understand and predict patient outcomes even with limited historical knowledge and patient data.

When creating a HDT for patient morbidity diagnosis and treatment evaluation, it is clear that the modeler will be missing some empirical data that would explain key phenomena through which independent variables interact to produce complex and synergetic nonlinear effects that may amplify health risks. Therefore, the chosen modeling method must address this lack of a priori knowledge in order to correctly establish relationships between influencing variables.

Probabilistic modeling methods attempt to develop a fundamental understanding of the most crucial root factors that impact morbidity using statistical treatment of research data or experimental results. Therefore, people who favor taking a statistical approach to precision medicine often argue that data fidelity issues of multimorbidity can be solved by assigning more resources to the collection of big data, improving the sophistication of Bayesian models and applying machine learning to determine correlations across datasets. However, this ignores the fundamental problem of uncertainty. In order to trust predictions from AI, it is necessary to confirm that both the model's equations and the entire database that it was built from are without errors.

A complex dataset that is sufficient to cover a problem as vast as multimorbidity is unlikely to contain no imperfections. In such cases, dataset issues can range from huge amounts of missing data (that are not missing at random), or unmeasured confounding, to systematic errors in the dataset (e.g., incorrect coding of drug treatments), to data collection issues that cause the distribution of data to be different than originally thought.

Even without data errors, statistical methods are difficult to analyze and are not able to efficiently cover new and complex situations when the relationships of different variables are not known. To satisfy flexibility and scalability requirements, statistical methods attempt to replicate the apparent randomness of morbidity using existing research data and observations. Such approaches often use population averages, which forcefully ignore outliers.

Figure 24:
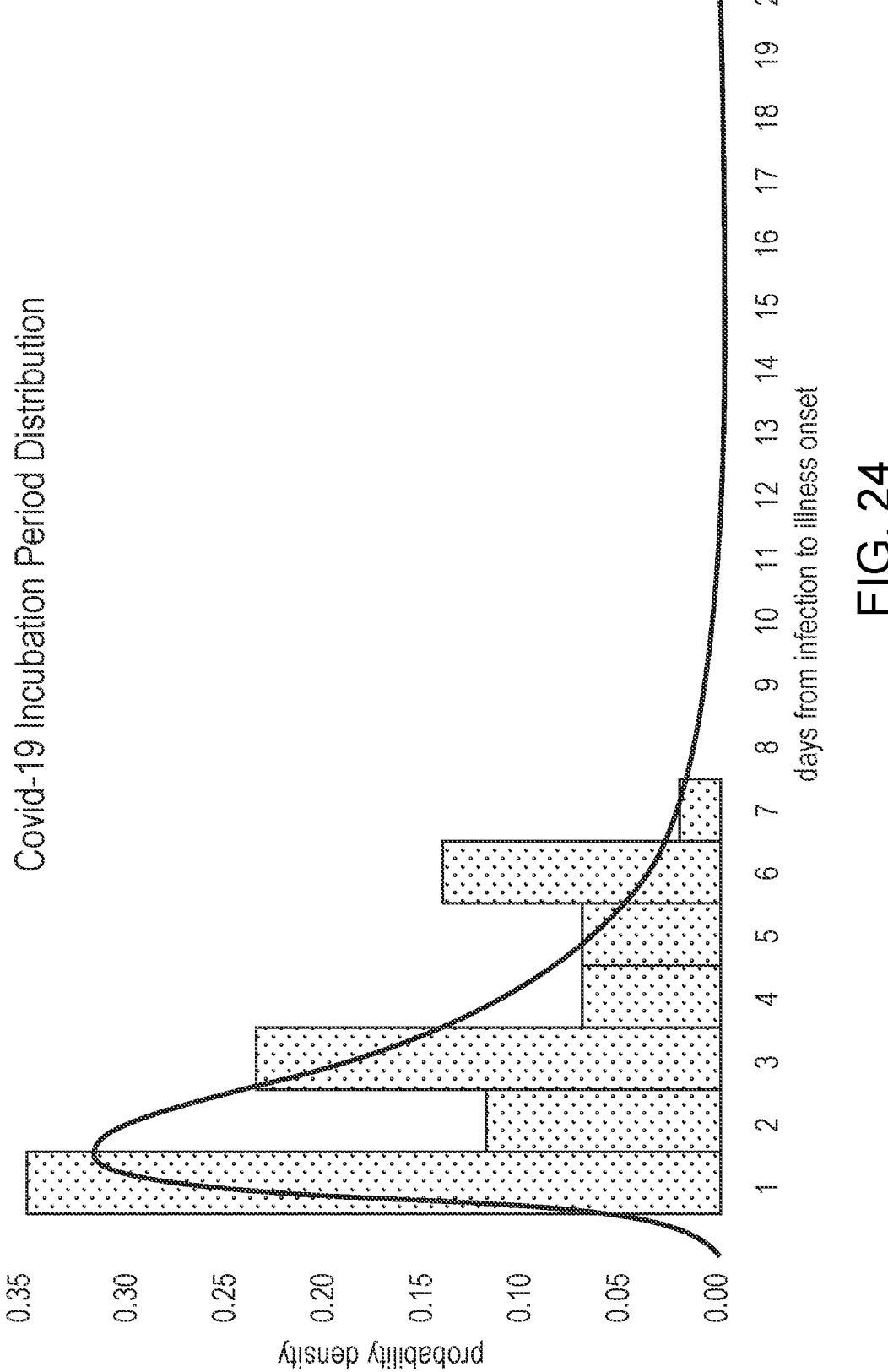
FIG. 24 illustrates a typical probability-based incubation model.
Figure 25:
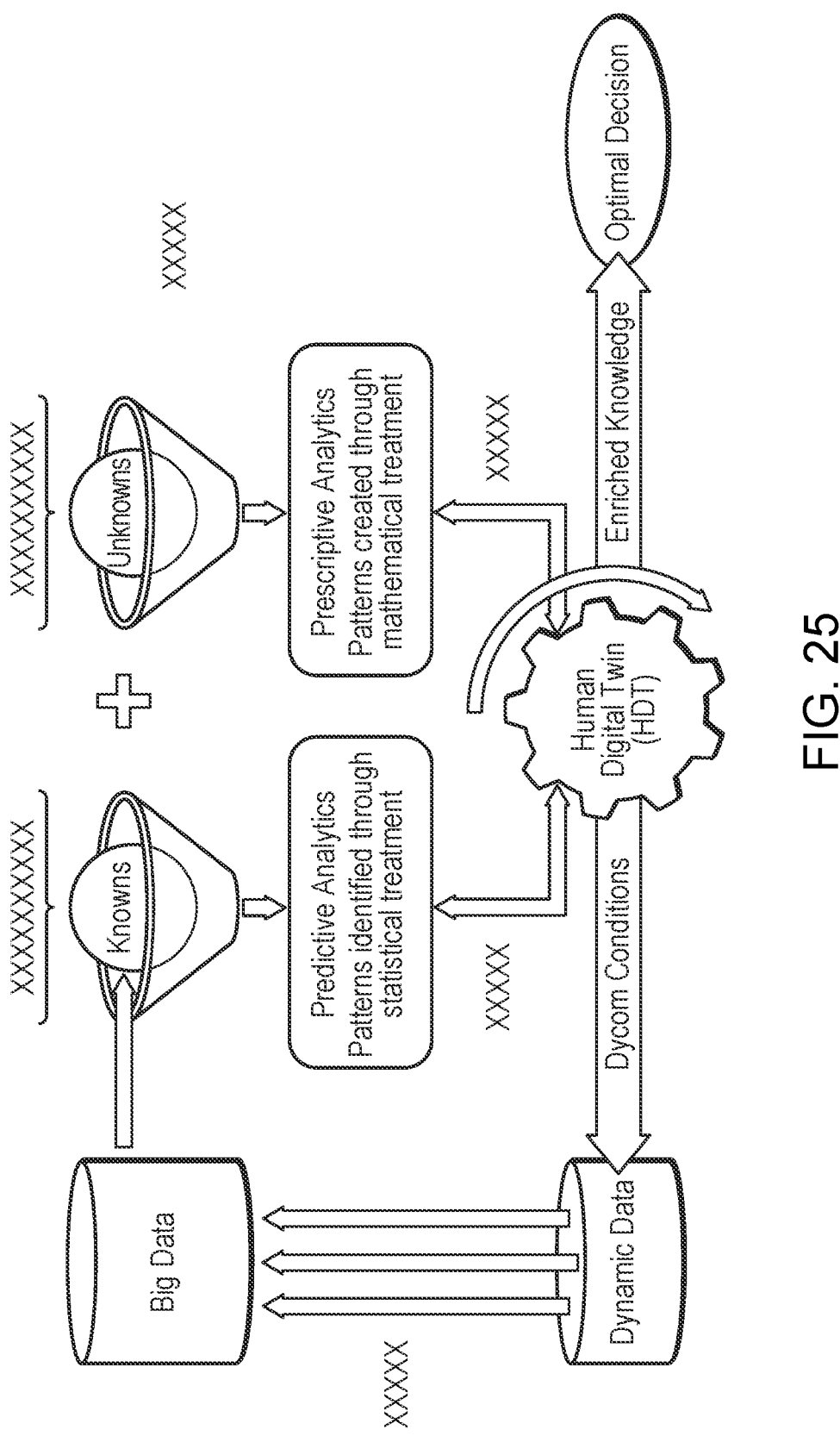
FIG. 25 illustrates an overview of a process in an example embodiment.

As example, FIG. 24 illustrates a typical probability-based incubation model that shows the period between infection and illness onset was 1-7 days for Covid-19 patients in South Korea.1 From this, researchers determined the median incubation period was three days (95% Confidence Interval, 0.6-8.2). This is helpful information if the goal is to vet public policy decisions such as the appropriateness of a 14-day quarantine requirement after an exposure to an infectious person, but the research does reveal that a longer incubation period is possible or the circumstances under which the days between infection and illness onset may be longer.

As more data is collected, the results of a probabilistic model may change. For example, an August 2020 retrospective study of the Covid-19 incubation period estimated a median incubation period of 7.76 days (95% CI: 7.02 to 8.53), mean of 8.29 days (95% CI: 7.67 to 8.9), the 90th percentile of 14.28 days (95% CI: 13.64 to 14.90), and the 99th percentile of 20.31 days (95% CI: 19.15 to 21.47).5 Overall, the researchers determined the probability of an incubation period longer than 2 weeks at between 5% and 10%. However, the researchers rightly concluded that it is difficult to estimate the proportion of incubation beyond 14 days in general when the sample size is small.

Since statistical models are static in nature, a new model must be built to capture any change in time. This divides time and space into two independent steps. Often, this simplification is sufficient to gain insights about a population at a specific point in time, but the method greatly truncates the understanding of morbidity causes and evolution for an individual patient.

While the dynamic behavior of human health can at times appear to be counterintuitive, unpredictable or even chaotic, and may therefore resemble random behavior, such behaviors are in fact deterministic. The perceived randomness and enormous scale of morbidity often leads to stochastic treatment, but in many retrospective cases morbidity can be mathematically defined with sufficient accuracy and reproducibility. This indicates that it should be possible to define the right system of equations to model the deterministic behavior of multimorbidity in prospective cases.

Most approaches that attempt to deal with the spatio-temporal modeling of human biological systems rely on some combination of numerical and analytical methods as a way to include quantitative and dynamic information. These models use nonlinear equations and methods, such as the perturbation method, that allow modelers to find an approximate analytical solution within a certain range. Partial differential equations (PDE) are an important part of these semi-analytical solutions because they provide a mathematical equation for two or more independent variables, an unknown function (dependent on those variables), and partial derivatives of the unknown function with respect to the independent variables.

Based on current research, it seems an analytical mathematical formulation that uses nonlinear dynamical equations may be the best way to deal with the high degree of complexity arising from the presence of multiple diseases, their biological and non-biological determinants and consequences, and multiple internal and external interactions in time and space. Specifically, a perturbed graph solution might be the best way to fill the knowledge gap of multimorbidity. In this case, nonlinear dynamical equations could be used to model the dynamic complexity of the system being studied, improve the coverage of missing values and deliver better certainty to support critical decisions in advanced digital applications.

When creating multimorbidity intelligence, it is clear that some of the data will be available using historical information or big data. But some data will be missing because the event has not yet happened and can only be revealed under certain conditions, e.g., a novel virus spreads from an animal to human. To expose the unknown data, it is important to identify all influencing forces including the small influences which may have a big effect due to the nonlinearity of human health.

A perturbed graph approach could help users escape the limits of theoretical models and statistical mechanics by computing each prediction based on the parameters involved in the expression regardless of past experience or the collection of big data. Testing in retrospective cases shows that using a perturbed graph solution to include the dynamics of multimorbidity in the HDT may improve diagnosis certainty in many cases from ~40% to ~60%. Further research is needed to confirm these results, but at a minimum the approach shows promise for its ability to provide the level of understanding needed to build a serious and robust relational HDT that relates the cause to the effect for human health.

Using the situational data revealed by HDT, the ultimate objective is to automate health surveillance in order to identify when patient health risks may be increasing—even before the patient begins to experience severe symptoms. This would be accomplished by creating an Advanced Human Healthcare database that stores together a diagnosis definition and therapeutic actions that cover both the experience-based knowns and those that were previously unknown for the rapid identification of a potential health risk with immediate analysis of root causes and proposed curative actions (see FIG. 25).

Example embodiments for right-time health surveillance would use a database populated by the mathematical predictive platform. The goal is to alleviate the pains created by the traditional long cycle of healthcare, which starts with problem-analysis-diagnosis and ends with an eventual cure well beyond the optimal point of action.

Enriching the database with the dynamic characteristics that continuously evolve during a patient's lifetime, should allow the knowledge contained within the database to become more advanced. By continuously recording foundational or circumstantial health changes, the predictive platform should be able to identify any new risk, determine the diagnosis and define the remedial actions, and finally enhance the database with this new knowledge. Any change in initial conditions, such as the appearance of a novel disease, would restart the cycle to support a continuous enhancement of knowledge.

Figure 26:
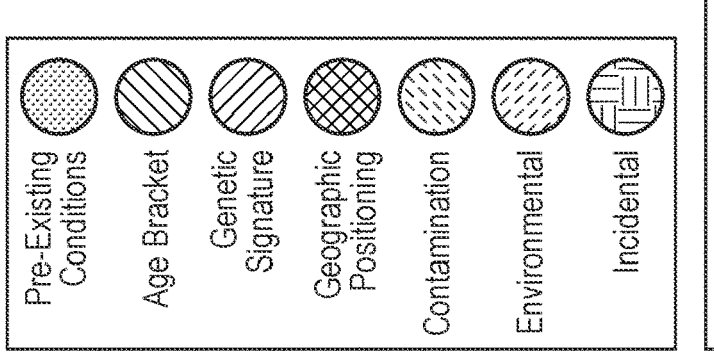
FIG. 26 illustrates an example dependency graph that may be implemented in a base model or patient model.

To begin the multimorbidity discovery process, it is first necessary to deconstruct human health to understand its constituent components and dependencies among them. The goal of deconstruction is to map the interdependencies, topology of structures, justification of choices, operational constraints, modes of operations, and data available to discover the hidden structures that form over time. FIG. 26 illustrates the complex web of interdependencies carried by an individual parameter as possible perturbations of multiple interacting networks that must be represented in order to account for the dynamic complexity of multimorbidity.

From this knowledge, a generic model can be built in software. The model should cover previously validated morbidity diagnoses, remediation and mitigation actions, as well as any influencing biological, public policy, healthcare, habits or social and environmental factors that improve the model's ability to reliably predict morbidity and prescribe effective treatments.

Once the model is fully constructed, sensitivity analysis and what-if analysis can be performed to determine how different values of an independent variable impact a dependent variable under a given set of assumptions. This analysis exposes the unknown influences of multimorbidity and delivers the algorithmic derived knowledge needed for the rapid identification of a potential health risk with immediate analysis of root causes and proposed curative actions.

FIG. 27 is a table providing an example of a sensitivity analysis performed for Covid-19 patients. The goal of the sensitivity analysis in this case was to identify the determinant variables that cause a patient to become critically ill. Here, the model confirmed the importance of including preexisting conditions as a predictor of patient criticality.

By analyzing predictive outcomes produced by the HDT versus known cases under various conditions, the modeler is able to confirm the representativeness, acceptable accuracy and robust predictability of the model. If done correctly, the HDT should match known scenarios within 2-3% of reality. If this is not the case, the modeler adjusts the parameters of the HDT until the desired representativeness, accuracy and predictability is achieved.

Once a generic HDT has been verified accurate and representative, it can be customized in clinical care settings with patient specific data from electronic health records and medical evaluations. After completing this customization, care providers or AI automated technologies can use the HDT to evaluate scenarios under different patterns of initial conditions and dynamic constraints to identify the circumstances under which health risks increase and use the corresponding information to evaluate the case.

Figure 28:
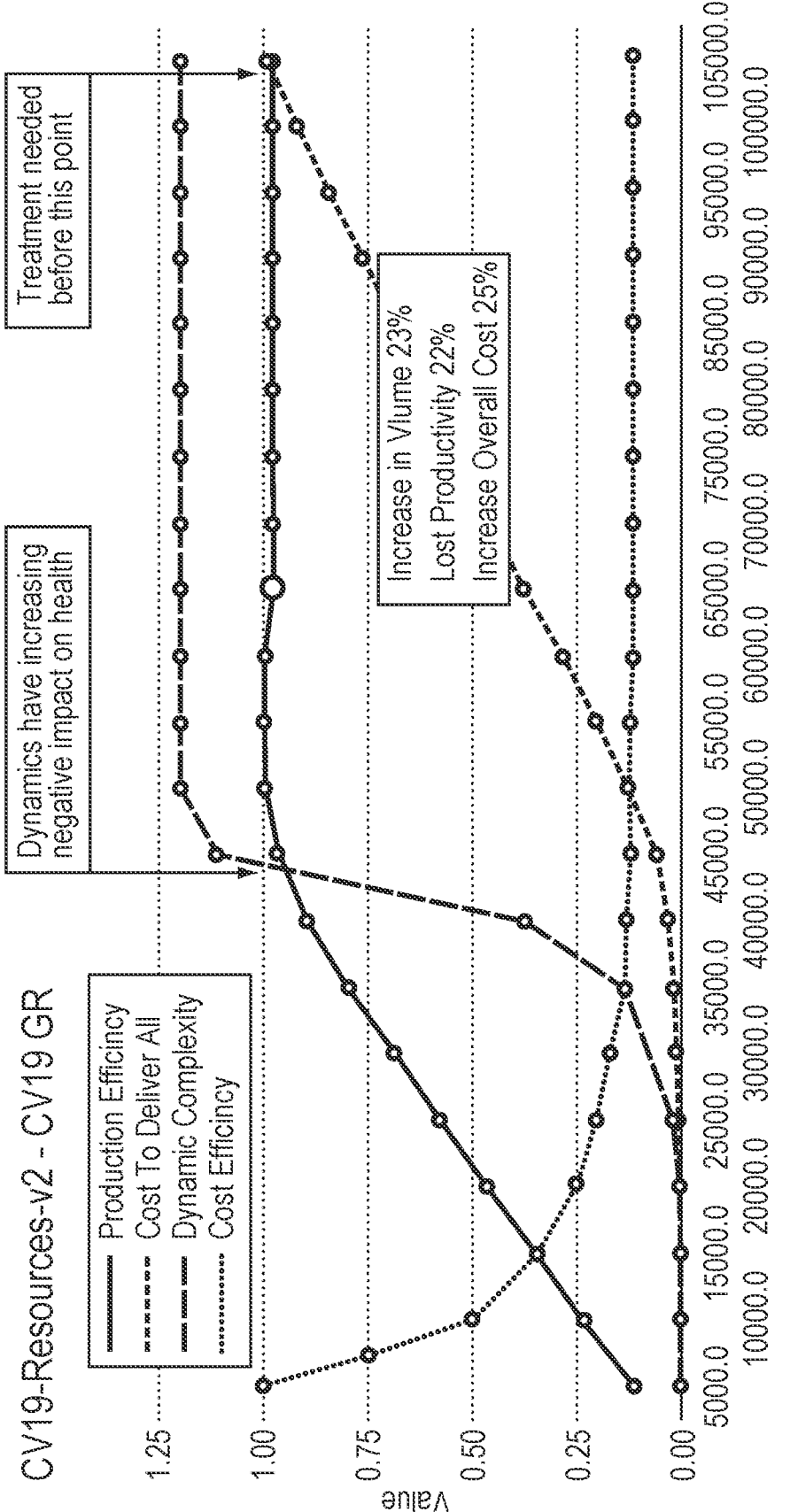
FIGS. 28 and 29 are graphs illustrating scenario analysis.
Figure 29:
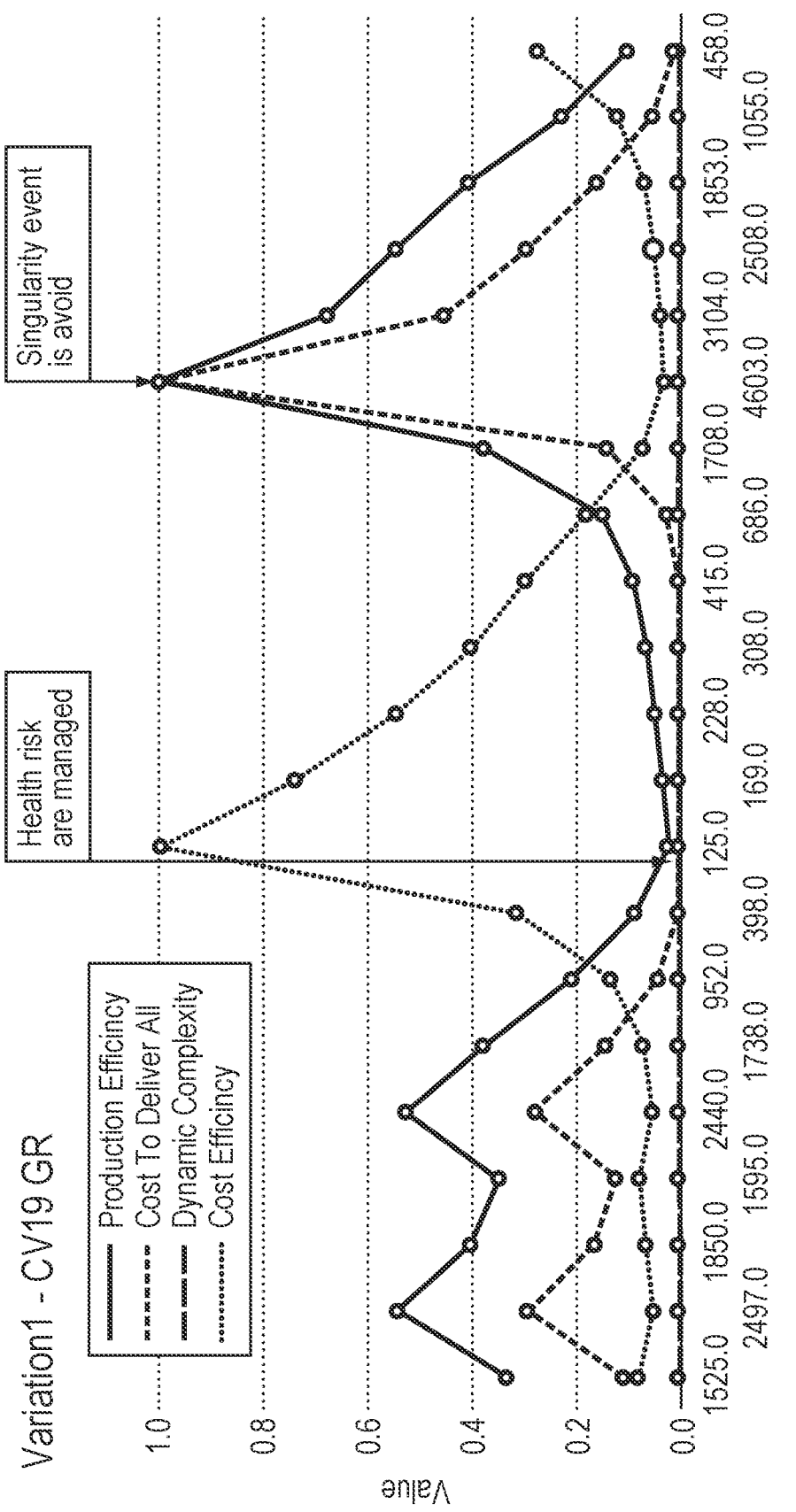

The use of metrics can help clinicians quantify morbidity risk and evaluate various treatment options. For example, FIG. 28 shows a HDT graph created using the perturbation method, which visually illustrates how the dynamics of multimorbidity may negatively impact a patient's health in a particular scenario and provides an indication of how much time is available to find an effective treatment. FIG. 29 shows an example of how same HDT model could be used to explore which actions might best manage the patient's health risks and avoid a singularity event (e.g., death or irreversible organ damage).

Ultimately, the value of HDT, AI, deep learning and neural computation technologies in medicine will only be realized if they can quickly deliver to users something complementary and more complete than the current knowledge domain. To identify, anticipate and cure health issues, it will be necessary to continuously compute the HDT at any point. This requirement necessitates moving to a robotic cognitive approach that can be applied quasi instantaneously to identify and eventually heal any health imbalances that may lead to an undesirable outcome. Therefore, the ultimate goal should be to create an HDT robot that can execute the following sequence of individual tasks for each patient and provide the results to the attending doctor:

a) Select the appropriate HDT model
b) Create a scenario by selecting from the following options:
   i. Diagnosis
   ii. Clinical Practice Therapeutics
   iii. Experimental Therapeutics (e.g. Stem Cell)
c) Select or deselect patient parameters in real-time from a list of choices that cover preexisting conditions, genetics, analysis, geography, age, etc.
d) Compute the case (see FIG. 30 as an example of scenario computations) and deliver color coded results to the attending doctor so that she/he can review the factors limiting the health of the patient and disease criticality
e) Use the rule engine to prescribe the best course of treatment or identify the need for additional diagnostic tests Using already available AI, deep learning and neural computation technologies, the robot should be able to provide the doctor and patient a robust diagnosis and recommend a treatment plan in 20 minutes or less using the proposed process. The limiting factor here is the time the computer takes to process more than 3,000 components in the graph. As computer processing technologies advance, the time to deliver results will become even faster. In any case, the ability of the computer to calculate the influence of thousands of influencing health factors in a relatively short period of time far exceeds the capabilities of any current statistical method or doctor who may at best be capable of processing a few influencing factors within the same amount of time.

Figure 31:
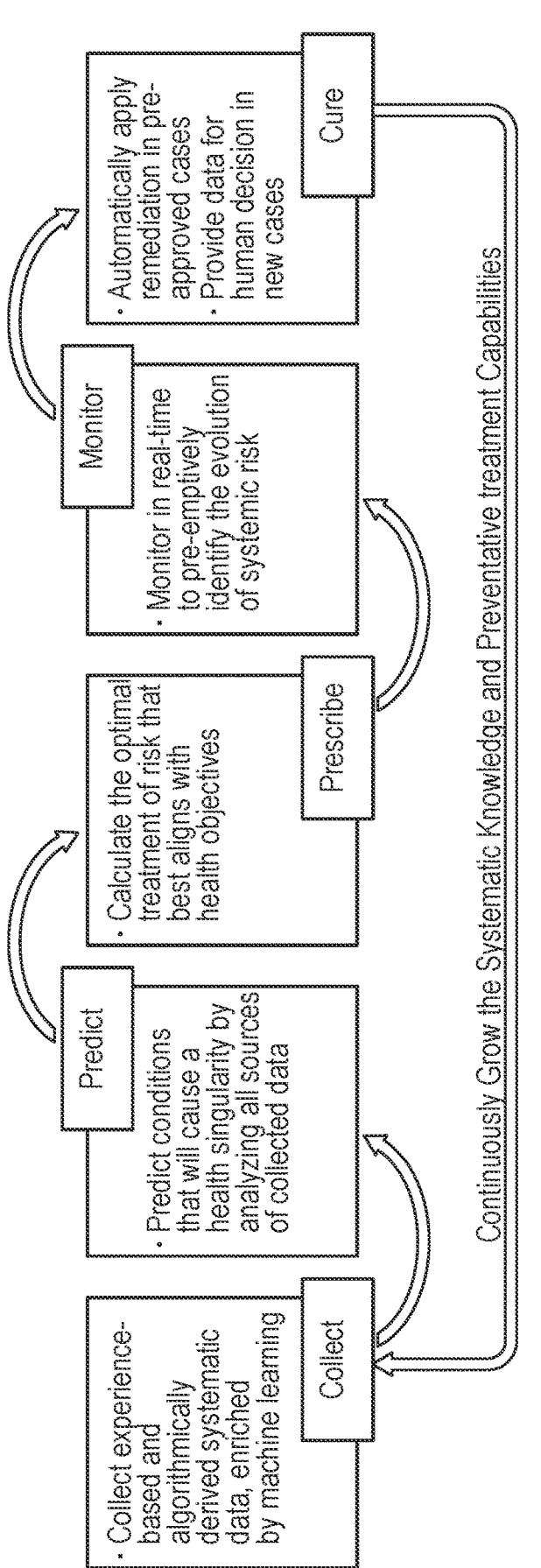
FIG. 31 illustrates an overview of a process in an example embodiment.

The pairing human perception and decision-making capabilities of supervised machine learning with the modeling methods presented herein provides an optimal synthesis for the intelligent treatment of disease (see FIG. 31). Once the full dynamics of morbidity is understood and its origins identified, healthcare will be better prepared to move to a more preventive stance. As new risks begin to form, automated algorithms can help medical practitioners intervene and proactively take actions at the right time to avoid any unwanted outcomes or unintended consequences.

The promise of improved patient outcomes and lower healthcare costs make precision medicine an attractive pursuit, but disruptive innovations in data science and analytics are needed to make full use of the current genetic sequencing, electronic medical records, and digital health technology breakthroughs. Modeling the spatio-temporal evolution of nonlinear systems with sufficient accuracy and reproducibility to support critical decisions in clinical practices will always be a challenge as long as data fidelity issues and missing values persist. However, advances in artificial intelligence and machine learning paired with deterministic, perturbed graph solutions show great promise in their ability to deal with the direct and indirect, convergent or degenerative solutions necessary to model multimorbidity.

A key advantage of a perturbed graph solution is that prior knowledge of what may cause morbidity is not needed. Only the variables and present conditions of a patient's health need to be known in order to test how any future changes may impact morbidity. In essence, the goal is to identify chaotic processes because they basically work as amplifiers by turning small causes into large effects. Once the causes are known, any health changes which may indicate a risk is building can be closely monitored using artificial intelligence and machine learning.

The development of modeling methodologies and technologies that leverage the approach presented in this paper seem to be a worthwhile pursuit. The encapsulation of these methods within software paired with robotics and AI capabilities should be further explored as an effective way to allow clinicians to autonomously predict patient outcomes without needing the assistance of modeling experts. To this end, additional collaboration with scientists, researchers and practitioners is needed to prove the robustness of the solution in prospective research cases and build the interfaces needed to support the use of HDT in critical clinical decision use cases.

The medical field is facing a diagnosis crisis that has not improved despite many technological and biological breakthroughs of the twenty-first century. Given the prevalence of diagnosis errors and the potential to do harm to misdiagnosed patients, the urgency of finding a solution should not be ignored. No one should be willing to accept a clinical diagnosis uncertainty rate of 37-92%. While some people may push for the collection of more health record data, more rigorous diagnosis training programs or better coordination between healthcare specialists as the solution, none of these actions will improve the standard of patient care or judiciously manage the associated costs if uncertainty persists.

Gaining confidence in any given analysis is the backbone of both human and artificial decision-making. The uncertainty inherent in probability-based diagnoses must be solved or else any attempts to meet the goals of precision medicine will remain prone to error, especially in multimorbidity cases, because complex and ambiguous presentations cannot be covered by experience and research data alone. No matter how much data is collected or how well-trained a doctor may be, the dynamics of human health cannot always be inferred from knowledge, experience or intuition.

On the surface, the call to upend hundreds of years of medical diagnostic practices built upon analogies and statistics may seem radical, but the disruption is necessary. Research has proven that health is affected by complex interactions between genetics, biochemistry, physiology, microbiology, biomechanics, and indirectly impacted by less obvious factors, like extrinsic factors such as public policy, environment, or social interactions with others. To improve diagnostic certainty in clinical settings, new methods are needed to quickly and reliably relate these complex causes into effects for an individual patient.

The persistence of uncertainty in patient diagnostics and treatment plans shows the limits of traditional reliance on probabilistic and Bayesian analysis methods. Shifting from a probabilistic to a deterministic approach for medical diagnosis using HDT shows significant promise for its ability to support the goals of precision medicine and overcome many obstacles preventing the adoption of AI in clinical practices. Other industries and scientific disciplines are already making this shift to increase certainty in decisions and ready AI applications for more serious and autonomous deployments in alignment with the goals of the fourth industrial revolution.1 The ability to use human genome discoveries, electronic health records, pharmaceutical advancements, stem cell research, robotics and other modern medicine innovations in clinical practices depends on the adoption of more robust modeling solutions.

Using a perturbed graph solution to build an HDT that represents the full spatio-temporal evolution of multimorbidity should be vetted as the preferred way to provide clinicians with the capabilities they need to develop a more accurate understanding of how morbidity risk factors and the efficacy of therapeutics will impact individual patients. The goal of such efforts should be to improve the accuracy of clinical diagnosis cases, increase the efficacy of therapeutic treatments and reduce healthcare costs by minimizing unnecessary surgeries, hospitalizations, referrals and overuse of high-technology medicine.

Now is the time to advance patient diagnosis and treatment decisions from an artform to a scientific discipline that takes advantage of the deterministic modeling methods used in other branches of science. Pairing deterministic, perturbed graph modeling software with robotics and AI capabilities can allow clinicians to autonomously predict patient outcomes without needing the assistance of modeling experts. To this end, the authors call upon the collaboration of scientists, researchers and practitioners to prove the robustness of the solution in prospective research cases and build the interfaces necessary to support the use of HDT in critical clinical decision use cases.

The teachings of all patents, published applications and references cited herein are incorporated by reference in their entirety. While example embodiments have been particularly shown and described, it will be understood by those skilled in the art that various changes in form and details may be made therein without departing from the scope of the embodiments encompassed by the appended claims.

What is claimed is:

1. A computer-implemented method of providing a digital computer simulation of health of a human patient, comprising:

obtaining in computer memory, a base model of a human being, the base model being a mathematical model incorporating rules that govern 1) a response by the human being to a disease, and 2) a relation between health metrics and the disease, the health metrics including a resistance metric indicating a measure of resistance to the disease, said obtaining being automatically performed by a processor;

obtaining in computer memory, by the processor, health attributes of the human patient, the health attributes including at least one of a genetic trait, a blood lipid profile, and a representation of a medical imaging report;

responsively generating in computer memory, by the processor, a patient model from the base model and the health attributes of the human patient, the patient model incorporating a patient-specific representation of the rules of the base model and a representation of the health attributes, the patient-specific representation of the rules of the base model including rules that govern response by the patient to a certain disease;

generating in computer memory, by the processor, plural sets of parameters, each of the plural sets of parameters indicating respective variables having a causal relation to the health metrics;

automatically generating a computer precision medicine evaluation of the patient by executing the patient model using a deterministic model, said executing being performed by the processor and producing: (a) respective simulations of the health metrics of the patient model under the plural sets of parameters over a given simulated time period, (b) plural resistance metric results based on the deterministic model, each of the plural resistance metric results indicating a change in the resistance metric under a respective set of parameters over the given simulated time period, and (c) an occurrence probability of the patient model transitioning from an initial state to each of a plurality of successive states during the given simulated time period, each of the successive states corresponding to a respective one of the plural sets of parameters, wherein the produced respective simulations, plural resistance metric results, and occurrence probability support the computer precision medicine evaluation of the patient with respect to at least the certain disease;

automatically determining a risk, by the processor, based on the produced simulations, the plural resistance metric results, and the occurrence probability of the generated precision medicine evaluation, the risk being of the patient model transitioning from the initial state to a diseased state, the diseased state representing the patient being afflicted by the certain disease;

automatically determining, by the processor, a diagnosis and a remedy, the remedy being determined by 1) identifying a subset of the health metrics that are negatively correlated with the diseased state, and 2) identifying the remedy as one of the respective variables associated with the identified subset of health metrics, the remedy identifying a modification to the patient model that reduces the determined risk;

generating as clinically-actionable output, by the processor, a map indicating 1) the processor determined diagnosis of the patient based on the determined risk, and 2) the determined remedy, said generating output being in a manner controlling computer diagnosis of patent-specific outcomes; and responsive to the clinically-actionable output, treating the patient in accordance with the remedy by administering to the patient one or more of: a medication, physical therapy, and other therapy.

2. The method of claim 1, wherein the base model incorporates rules that govern a response by the human being to at least one of immune reactivations, irregular immune response, autoimmunity, preexisting conditions and environmental parameters.

3. The method of claim 1, wherein the health metrics of the base model in computer memory include indications of human health dependability (HHD), the HHD being a measure of an integrity of an immune system to counteract the disease.

4. The method of claim 1, wherein the certain disease is a first disease; and wherein the plural sets of parameters in computer memory include at least one set of parameters indicating comorbidity of the first disease and a second disease.

5. The method of claim 1, wherein the certain disease is one of a cancer, a virus, and a bacterial infection.

6. The method of claim 1, further comprising:
identifying, by the processor, a correspondence between a subset of the health attributes, the produced plural resistance metric results, and the determined risk; and
determining, by the processor, the diagnosis based on the identified correspondence, the diagnosis indicating the subset of health attributes that exceed a threshold correspondence with the determined risk.

7. The method of claim 1, further comprising:
updating the patient model in computer memory to incorporate the modification; and
determining an expected improvement to a measure of an integrity of the patient's immune system to counteract the certain disease, the updating and determining being automatically performed by the processor.

8. The method of claim 7, further comprising reporting the remedy to a user.

9. The method of claim 7, wherein determining the remedy includes the processor:
generating an additional set of parameters in computer memory, the additional set of parameters indicating a health intervention, the health intervention including at least one of a medication, a therapy, and a diet;
responsively modeling the health metrics of the patient model in computer memory under the additional set of parameters to generate a resistance metric result; and
automatically identifying the remedy based on the health metrics associated with the health intervention.

10. The method of claim 1, wherein:
the map relates the diseased state to 1) corresponding instances of the plural sets of parameters and 2) the occurrence probability of the patient model transitioning from the initial state to the plurality of successive states; and
further comprising the processor determining, based on the map, at least one risk for at least one of the successive states of the patient model in computer memory, the at least one risk defining a probability of an outcome of the patient model including the diseased state.

11. The method of claim 1, further comprising the processor generating in computer memory a lookup table cross-referencing states of the patient model to corresponding ones of the risk.

12. The method of claim 11, wherein determining the risk includes the processor accessing the lookup table in computer memory using information on a given state of the patient or patient model.

13. The method of claim 11, further comprising the processor:
responsively analyzing a state of the patient; and
wherein determining the risk includes accessing the lookup table in computer memory using information on the state of the patient.

14. The method of claim 11, wherein the lookup table cross-references the states of the patient model to the corresponding ones of the risk and at least one remedy.

15. The method of claim 1, wherein the generating a patient model in computer memory includes the processor:
generating a dependency graph having a plurality of nodes representing the health attributes; and configuring dependencies between the plurality of nodes based on the rules.

16. A non-transitory computer-readable medium comprising instructions that, when executed by a computer, provide a digital computer simulation of health of a human patient including causing the computer to:
obtain in computer memory, by a processor, a base model of a human being, the base model being a mathematical model incorporating rules that govern 1) a response by the human being to a disease, and 2) a relation between health metrics and the disease, the health metrics including a resistance metric indicating a measure of resistance to the disease;
obtain in computer memory, by the processor, health attributes of a human patient, the health attributes including at least one of a genetic trait, a blood lipid profile, and a representation of a medical imaging report;
responsively generate in computer memory, by the processor, a patient model from the base model and the health attributes of the human patient, the patient model incorporating a patient-specific representation of the rules of the base model and a representation of the health attributes, the patient-specific representation of the rules of the base model including rules that govern response by the patient to a certain disease;
generate in computer memory, by the processor, plural sets of parameters, each of the plural sets of parameters indicating respective variables having a causal relation to the health metrics;
automatically generate a computer precision medicine evaluation of the patient by executing the patient model using a deterministic model, said executing being performed by the processor, and producing: (a) respective computer simulations of the health metrics of the patient model under the plural sets of parameters over a given simulated time period,
(b) plural resistance metric results based on the deterministic model, each of the plural resistance metric results indicating a change in the resistance metric under a respective set of parameters over the given simulated time period, and
(c) an occurrence probability of the patient model transitioning from an initial state to each of a plurality of successive states during the given simulated time period, each of the successive states corresponding to a respective one of the plural sets of parameters, wherein the produced respective simulations, plural resistance metric results, and occurrence probability support the computer precision medicine evaluation of the patent with respect to at least the certain disease;
automatically determine a risk, by the processor, based on the produced simulations, the plural resistance metric results, and the occurrence probability of the generated precision medicine evaluation, the risk being of the patient model transitioning from the initial state to a diseased state, the diseased state representing the patient being afflicted by the certain disease;
automatically determine, by the processor, a diagnosis and a remedy, the remedy being determined by 1) identifying a subset of the health metrics that are negatively correlated with the diseased state, and 2) identifying the remedy as one of the respective variables associated with the identified subset of the health metrics, the remedy identifying a modification to the patient model that reduces the determined risk;

generate as clinically-actionable output, by the processor, a map indicating 1) the processor determined diagnosis of the patient based on the determined risk, and 2) the determined remedy, said generating output being in a manner controlling computer diagnosis of patient-specific outcomes; and responsive to the clinically-actionable output, provide treatment to the patient in accordance with the remedy by administering one or more of: a medication, physical therapy, and other therapy.

17. The computer-readable medium of claim 16, further comprising instructions causing the computer to:

identify a correspondence between a subset of the health attributes, the produced plural resistance metric results, and the determined risk; and determine the diagnosis based on the identified correspondence, the diagnosis indicating the subset of health attributes that exceed a threshold correspondence with the determined risk.

18. The computer-readable medium of claim 16, further comprising instructions causing the computer to:

automatically update in computer memory the patient model to incorporate the modification.

\* \* \* \* \*